(12) United States Patent
Wittek et al.

(10) Patent No.: US 9,862,887 B2
(45) Date of Patent: Jan. 9, 2018

(54) LIQUID CRYSTAL MEDIUM AND LIQUID CRYSTAL DISPLAY

(71) Applicant: Merck Patent GmbH, Darmstadt (DE)

(72) Inventors: Michael Wittek, Erzhausen (DE); Malgorzata Rillich, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/395,115

(22) PCT Filed: Apr. 3, 2013

(86) PCT No.: PCT/EP2013/000988
§ 371 (c)(1),
(2) Date: Oct. 17, 2014

(87) PCT Pub. No.: WO2013/156113
PCT Pub. Date: Oct. 24, 2013

(65) Prior Publication Data
US 2015/0129800 A1 May 14, 2015

(30) Foreign Application Priority Data
Apr. 20, 2012 (EP) .................... 12002801

(51) Int. Cl.
| C09K 19/02 | (2006.01) |
| C09K 19/54 | (2006.01) |
| C09K 19/34 | (2006.01) |
| C09K 19/46 | (2006.01) |
| C07D 319/06 | (2006.01) |
| C09K 19/04 | (2006.01) |
| C09K 19/12 | (2006.01) |
| C09K 19/20 | (2006.01) |

(52) U.S. Cl.
CPC ........... *C09K 19/54* (2013.01); *C07D 319/06* (2013.01); *C09K 19/0275* (2013.01); *C09K 19/3402* (2013.01); *C09K 19/46* (2013.01); *C09K 2019/0448* (2013.01); *C09K 2019/0466* (2013.01); *C09K 2019/124* (2013.01); *C09K 2019/2035* (2013.01); *C09K 2019/3422* (2013.01)

(58) Field of Classification Search
CPC .................................................. C07D 319/06
USPC ...................................................... 252/299.5
See application file for complete search history.

(56) References Cited

U.S. PATENT DOCUMENTS

| 6,231,785 B1 | 5/2001 | Kondo et al. |
| 7,105,210 B2 * | 9/2006 | Heckmeier et al. ........... 428/1.1 |
| 7,470,456 B2 | 12/2008 | Yanai et al. |
| 7,842,358 B2 | 11/2010 | Czanta et al. |
| 7,989,038 B2 | 8/2011 | Yamashita et al. |
| 8,211,513 B2 | 7/2012 | Jansen |
| 8,409,673 B2 | 4/2013 | Haseba et al. |
| 8,475,887 B2 | 7/2013 | Haseba et al. |
| 2004/0173776 A1 | 9/2004 | Heckmeier et al. |
| 2007/0278450 A1 | 12/2007 | Yanai et al. |
| 2009/0237610 A1 | 9/2009 | Saito et al. |
| 2009/0256114 A1 * | 10/2009 | Yamashita et al. ...... 252/299.63 |
| 2010/0276635 A1 * | 11/2010 | Wittek et al. ............ 252/299.61 |
| 2011/0069245 A1 | 3/2011 | Haseba et al. |
| 2011/0180756 A1 * | 7/2011 | Goto ................... C07D 319/06 252/299.61 |
| 2011/0180876 A1 | 7/2011 | Laine et al. |
| 2011/0233466 A1 * | 9/2011 | Jansen ............... C09K 19/0275 252/299.61 |
| 2011/0253935 A1 | 10/2011 | Jansen et al. |
| 2011/0261311 A1 * | 10/2011 | Jansen ............... C09K 19/0275 349/182 |
| 2012/0099039 A1 | 4/2012 | Haseba et al. |
| 2012/0298916 A1 * | 11/2012 | Jansen et al. ............. 252/299.5 |
| 2013/0057947 A1 * | 3/2013 | Wittek ............... C09K 19/0275 359/321 |
| 2013/0100369 A1 | 4/2013 | Sagou et al. |
| 2013/0278849 A1 | 10/2013 | Yamamoto et al. |

(Continued)

FOREIGN PATENT DOCUMENTS

| CN | 1183075 C | 1/2005 |
| CN | 102199139 A | 9/2011 |
| CN | 103160287 A | 6/2013 |

(Continued)

OTHER PUBLICATIONS

International Search Report dated May 21, 2013 issued in corresponding PCT/EP2013/000988 application (pp. 1-4).

(Continued)

*Primary Examiner* — Chanceity Robinson
(74) *Attorney, Agent, or Firm* — Millen White Zelano and Branigan, PC; Csaba Henter; John Sopp

(57) ABSTRACT

The instant invention relates to mesogenic media comprising one or more compounds of formula D

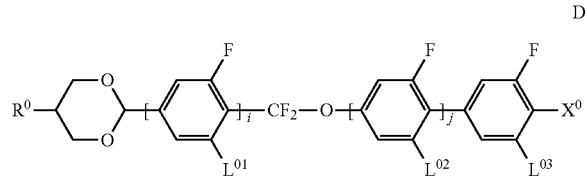

wherein the parameters are as specified in the text, preferably to mesogenic media showing a blue phase, preferably stabilised by a polymer, and their use in electro-optical light modulation elements and their respective use in displays, as well as to such devices.

16 Claims, No Drawings

(56) References Cited

U.S. PATENT DOCUMENTS

2013/0306908 A1* 11/2013 Jansen ............... C07D 307/06
                                                    252/299.61

FOREIGN PATENT DOCUMENTS

| | | |
|---|---|---|
| CN | 103328458 A | 9/2013 |
| DE | 19946228 A1 | 5/2000 |
| EP | 1454975 A2 | 9/2004 |
| EP | 1862526 A1 | 12/2007 |
| EP | 2302015 A1 | 3/2011 |
| JP | 2008-7752 A | 1/2008 |
| JP | 2011-195587 A | 10/2011 |
| JP | 2011-225566 A | 11/2011 |
| TW | 201139354 A | 11/2011 |
| WO | 2010/134430 A1 | 11/2010 |
| WO | 2011/162142 A1 | 12/2011 |
| WO | 2012/043145 A1 | 4/2012 |

OTHER PUBLICATIONS

English Translation Abstract of JP 2008-007752 published Jan. 17, 2008.
Chinese Office Action dated Sep. 1, 2015 issued in corresponding CN 201380020200.7 application (pp. 1-11).
English Abstract of CN 102199139 A published Sep. 28, 2011.
English Abstract of CN 103160287 A published Jun. 19, 2013.
English Abstract of CN 103328458 A published Sep. 25, 2013.
TW Office Action dated Sep. 12, 2016 issued in corresponding TW102114087.
1st Office Action corresponding to JP 2015-506109—Drafting Date: Nov. 30, 2016—Dispatching Date: Dec. 2, 2016.
Bibliographic data: English Abstract—JP2011195587(A)—Oct. 6, 2011.
Bibliographic data: English Abstract—JP 2011225566(A)—Nov. 10, 2011.

* cited by examiner

LIQUID CRYSTAL MEDIUM AND LIQUID CRYSTAL DISPLAY

FIELD OF THE INVENTION

The present invention relates to compounds, media comprising these compounds and to electro-optical displays comprising these media as light modulation media. Preferably, the compounds of the present invention are mesogenic compounds and they are preferably used in liquid crystalline media. In particular the electro-optical displays according to the present invention are displays, which are operated at a temperature, at which the mesogenic modulation media are in an optically isotropic phase, preferably in a blue phase.

PROBLEM TO BE SOLVED AND STATE OF THE ART

Electro-optical displays and mesogenic light modulation media, which are in the isotropic phase when being operated in the display are described in DE 102 17 273 A. Electro-optical displays, and mesogenic light modulation media, which are in the optically isotropic blue phase, when being operated in the display are described in WO 2004/046 805.

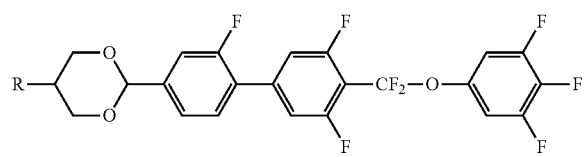

are mentioned as compounds for liquid crystalline compositions e.g. in US 2009/0256114 A1 and US/2011/0180756 A1.

The mesogenic media and displays described in these references provide several significant advantages compared to well-known and widely used displays using liquid crystals in the nematic phase, like for example liquid crystal displays (LCDs) operating in the twisted nematic (TN)-, the super twisted nematic (STN)-, the electrically controlled birefringence (ECB)-mode with its various modifications and the in-plane switching (IPS)-mode.

Amongst these advantages are most pronounced their much faster switching times, and significantly wider optical viewing angle.

Whereas, compared to displays using mesogenic media in another liquid crystalline phase, as e.g. in the smectic phase in surface stabilized ferroelectric liquid crystal displays (SSF LCDs), the displays of DE 102 17 273.0 and WO 2004/046 805 are much easier to manufacture. For example, they do not require a very thin cell gap and in addition the electro-optical effect is not very sensitive to small variations of the cell gap.

However, the liquid crystal media described in these patent applications still require operating voltages, which are not low enough for some applications. Further the operating voltages of these media vary with temperature, and it is generally observed, that at a certain temperature the voltage dramatically increases with increasing temperature. This limits the applicability of liquid crystal media in the blue phase for display applications. A further disadvantage of the liquid crystal media described in these patent applications is their moderate reliability which is insufficient for very demanding applications. This moderate reliability may be for example expressed in terms of the voltage holding ratio (VHR) parameter, which in liquid crystal media as described above may be below 90%.

Some compounds and compositions have been reported, which possess a blue phase between the cholesteric phase and the isotropic phase and can usually be observed by optical microscopy. These compounds or compositions, for which the blue phases are observed, are typically single mesogenic compounds or mixtures showing a high chirality. However, generally the blue phases observed only extend over a very small temperature range, which is typically less than 1 degree centigrade wide, and/or the blue phase is located at rather inconvenient temperatures.

In order to operate the novel fast switching display mode of WO 2004/046 805 the light modulation medium to be used has to be in the blue phase over a broad range of temperatures encompassing ambient temperature, however. Thus, a light modulation medium possessing a blue phase, which is as wide as possible and conveniently located, is required.

There has been ongoing development of improved liquid crystalline media for these applications. E.g. WO 2012/043145 A1 discloses media comprising, amongst others, compounds of formulae

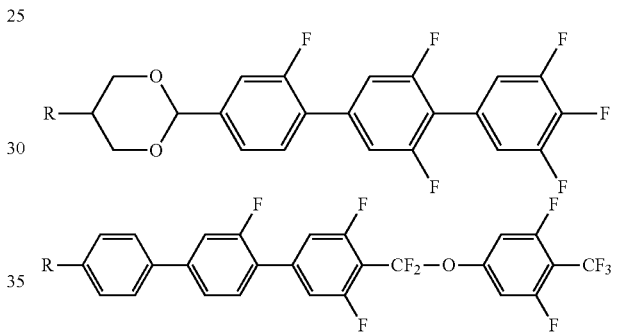

and also amongst various others mentions general formulae like

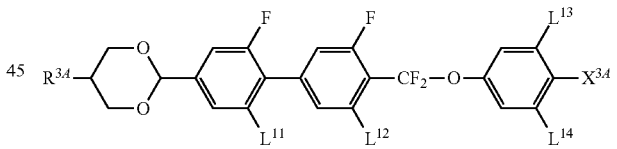

However, the respective liquid crystalline media are characterized by physical properties which do not fulfil the criteria for demanding applications in displays. In particular they feature unfavourably high values of the rotational viscosity leading to long response times, require high operation voltages and have no suitably wide phase ranges of the mesophases, in particular a limited stability at low temperatures.

Therefore, there is a strong need for a modulation medium with a blue phase with a wide phase range, which may be achieved either by an appropriate mixture of mesogenic compounds themselves or, preferably by mixing a host mixture with appropriate mesogenic properties with a single dopant or a mixture of dopants that stabilises the blue phase over a wide temperature range, which is not, or not so strongly impeded by the draw backs of the known media.

Summarizing, there is a need for liquid crystal media, which can be operated in liquid crystal displays, which are operated at temperatures where the media is in the blue phase, which provide the following technical improvements:
a reduced operating voltage,
a reduced temperature dependency of the operating voltage and
an improved reliability, e.g. VHR.

Present Invention

Surprisingly, it now has been found that mesogenic media exhibiting a blue phase and comprising one or more of formula D

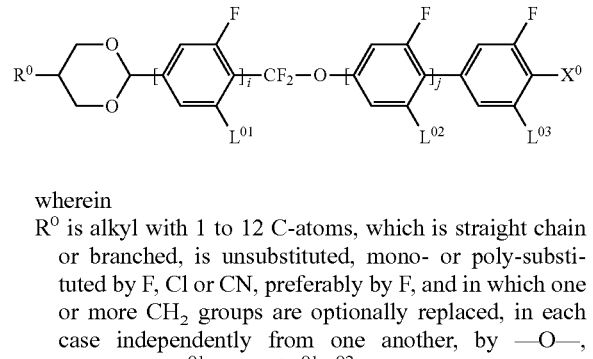

D wherein
R$^0$ is alkyl with 1 to 12 C-atoms, which is straight chain or branched, is unsubstituted, mono- or poly-substituted by F, Cl or CN, preferably by F, and in which one or more CH$_2$ groups are optionally replaced, in each case independently from one another, by —O—, —S—, —NR$^{01}$—, —SiR$^{01}$R$^{02}$—, —CO—, —COO—, —OCO—, —OCO—O—, —S—CO—, —CO—S—, —CY$^{01}$=CY$^{02}$— or —C≡C— in such a manner that O and/or S atoms are not linked directly to one another, preferably alkyl or alkenyl, most preferably alkyl with 1 to 7 C-atoms,
Y$^{01}$ and Y$^{02}$ are, independently of each other, F, Cl or CN, and alternatively one of them may be H,
R$^{01}$ and R$^{02}$ are, independently of each other, H or alkyl with 1 to 12 C-atoms,
L$^{01}$ to L$^{03}$ are in each occurrence independently of each other H or F, preferably at least two of them are F and the others are H or F,
X$^0$ is F, OCF$_3$, CF$_3$ or CN, preferably F or CF$_3$,
i is 1, 2 or 3, preferably 1 or 2,
j is 0 or 1, and
i+j is 1, 2 or 3, preferably 1 or 2 and most preferably 2
amongst which chiral compounds are encompassed, too, allow to realize media with an acceptably high clearing point and/or a rather high stability of the voltage holding ratio against temperature and/or UV-load and in particular against the latter.

In a preferred embodiment of the present invention the mesogenic media comprise one more compounds of formula D, preferably selected from the group of compounds of its sub-formulae D-1 to D-4, preferably of formulae D-1 and/or D-2,

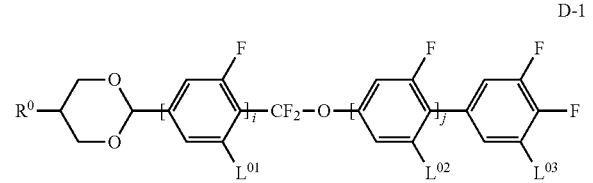

D-1

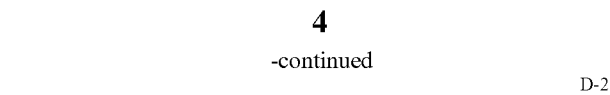

D-2

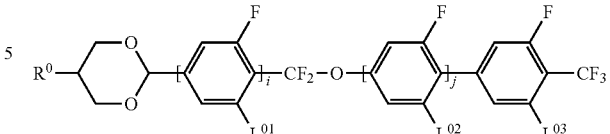

D-3

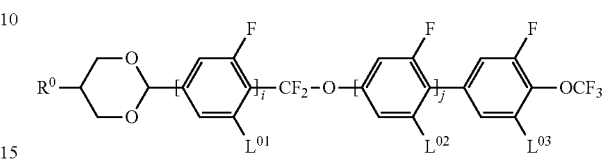

D-4

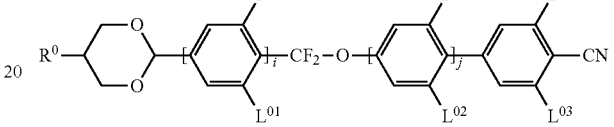

wherein the parameters have the meanings given under formula D above and R$^0$ preferably is n-alkyl, most preferably ethyl, n-propyl, n-butyl, n-pentyl or n-hexyl.

In a preferred embodiment of the present invention the media according to the present invention comprise one more compounds of formula D-1, preferably selected from the group of compounds of formulae D-1a to D-1d, preferably one more compounds each of formula D-1b and/or D-1c and most preferably of formula D-1b, D-1a

D-1b

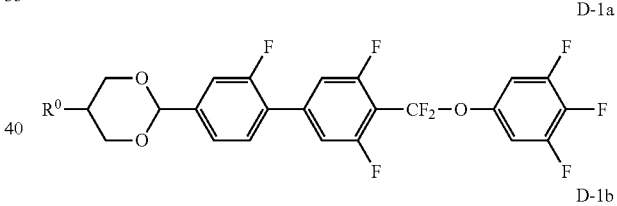

D-1c

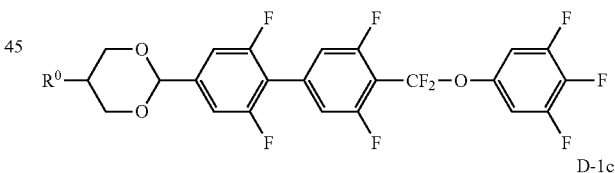

D-1d

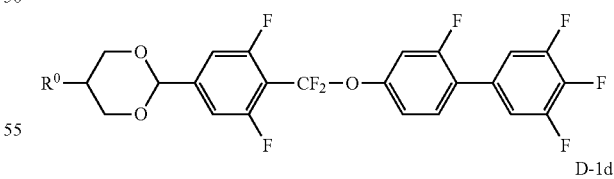

wherein R$^0$ has the meaning given under formula D-1 above and preferably is n-alkyl, most preferably ethyl, n-propyl, n-butyl, n-pentyl or n-hexyl.

In a preferred embodiment of the present invention the media according to the present invention comprise one more compounds of formula D-2, preferably selected from the group of compounds of formulae D-2a to D-2d, preferably one more compounds each of formula D-2b and/or D-2c and most preferably of formula D-2b,

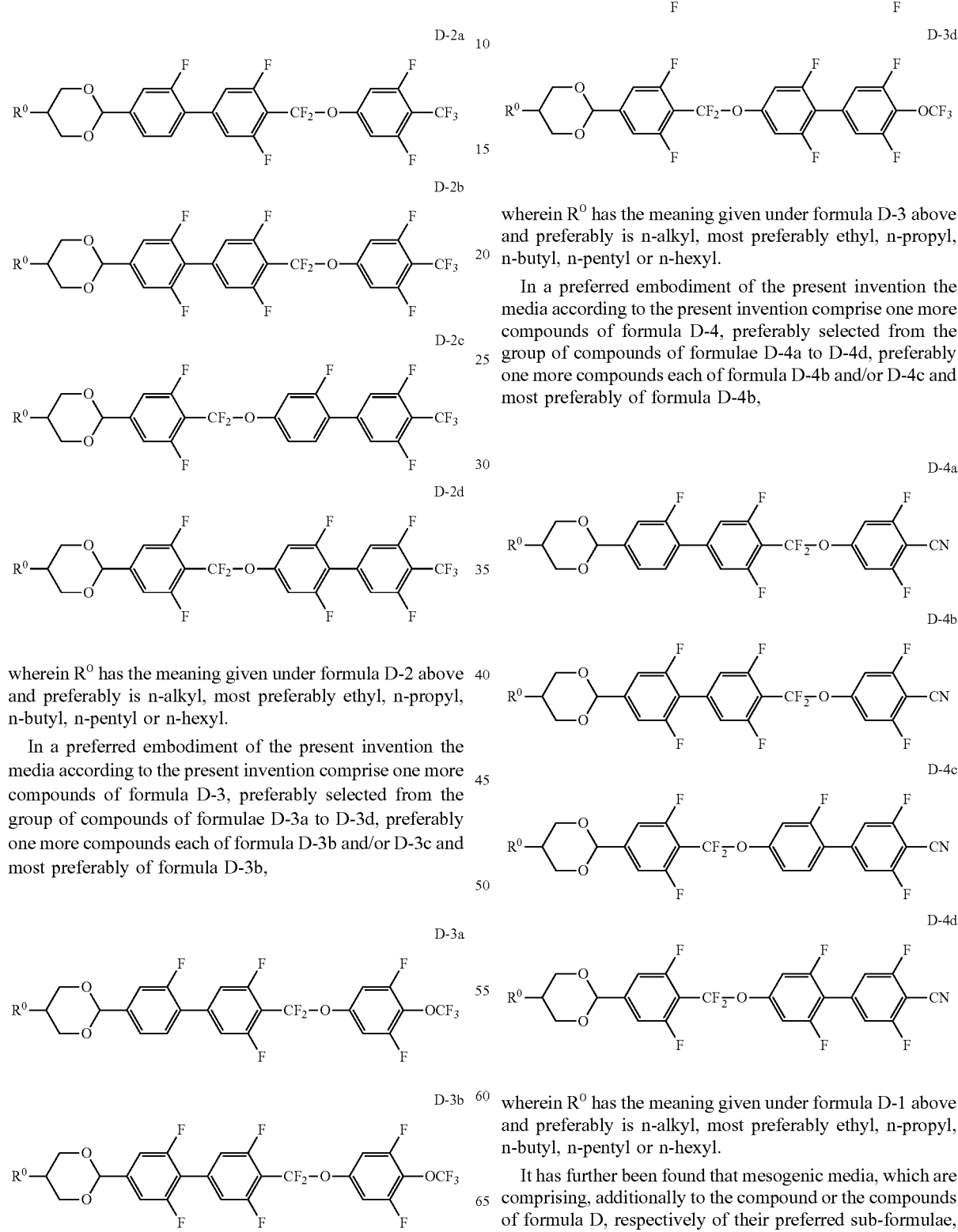

wherein R⁰ has the meaning given under formula D-2 above and preferably is n-alkyl, most preferably ethyl, n-propyl, n-butyl, n-pentyl or n-hexyl.

In a preferred embodiment of the present invention the media according to the present invention comprise one more compounds of formula D-3, preferably selected from the group of compounds of formulae D-3a to D-3d, preferably one more compounds each of formula D-3b and/or D-3c and most preferably of formula D-3b, wherein R⁰ has the meaning given under formula D-3 above and preferably is n-alkyl, most preferably ethyl, n-propyl, n-butyl, n-pentyl or n-hexyl.

In a preferred embodiment of the present invention the media according to the present invention comprise one more compounds of formula D-4, preferably selected from the group of compounds of formulae D-4a to D-4d, preferably one more compounds each of formula D-4b and/or D-4c and most preferably of formula D-4b, wherein R⁰ has the meaning given under formula D-1 above and preferably is n-alkyl, most preferably ethyl, n-propyl, n-butyl, n-pentyl or n-hexyl.

It has further been found that mesogenic media, which are comprising, additionally to the compound or the compounds of formula D, respectively of their preferred sub-formulae, one or more compounds of formula I

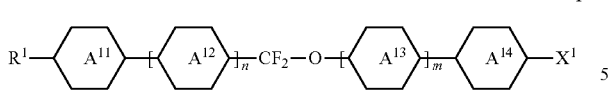
I wherein
R¹ is alkyl, which is straight chain or branched, preferably has 1 to 20 C-atoms, is unsubstituted, mono- or polysubstituted by F, Cl or CN, preferably by F, and in which one or more CH₂ groups are optionally replaced, in each case independently from one another, by —O—, —S—, —NR^{O1}—, —SiR^{O1}R^{O2}—, —CO—, —COO—, —OCO—, —OCO—O—, —S—CO—, —CO—S—, —CY^{O1}=CY^{O2}— or —C≡C— in such a manner that O and/or S atoms are not linked directly to one another, preferably n-alkyl, n-alkoxy with 1 to 9 C-atoms, preferably 2 to 5 C-atoms, alkenyl, alkenyloxy or alkoxyalkyl with 2 to 9 C-atoms, preferably with 2 to 5 C-atoms or halogenated alkyl, halogenated alkenyl or halogenated alkoxy, preferably mono fluorinated, di-fluorinated or oligofluorinated alkyl, alkenyl or alkoxy, most preferably n-alkyl, n-alkoxy, alkenyl, alkenyloxy or alkoxyalkyl,
Y^{O1} and Y^{O2} are, independently of each other, F, Cl or CN, and alternatively one of them may be H,
R^{O1} and R^{O2} are, independently of each other, H or alkyl with 1 to 12 C-atoms,
X¹ is F, Cl, CF₃, OCF₃ or CN, preferably by F, CF₃ or CN,

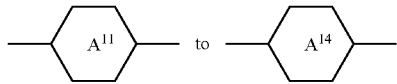

are in each occurrence independently of one another

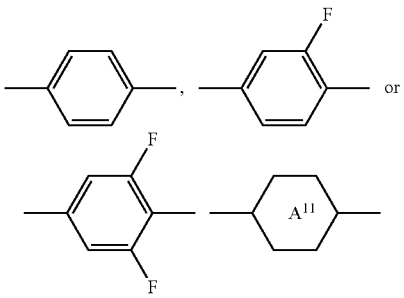

alternatively may be

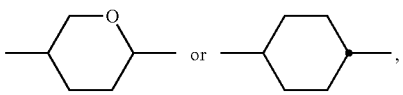

preferably

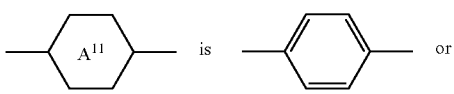

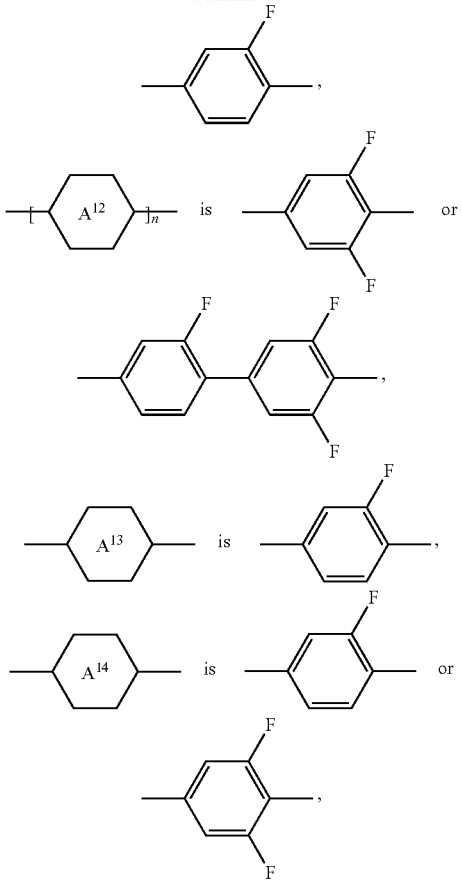

n is 0, 1 or 2, preferably 1 or 2,
m is 0 or 1, and
n+m is 0, 1 or 2, preferably 1 or 2, amongst which chiral compounds are encompassed, too, allow to realize media with an acceptably high clearing point and/or a rather high stability of the voltage holding ratio against temperature and/or UV-load and in particular against the latter.

The media of the present invention preferably comprise one or more compounds of formula I, preferably selected from the group of compounds of formulae I-1 to I-4, preferably selected from group of compounds of formulae I-1, I-2 and I-4, most preferably one or more compounds each of formulae I-1 and/or I-2 and/or I-4,

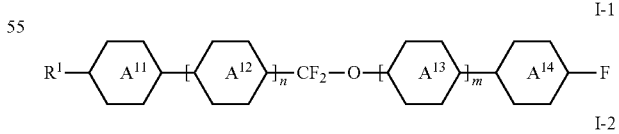
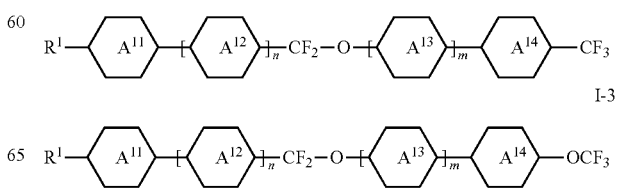

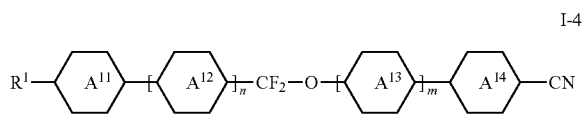

I-4 wherein the parameters have the meanings given under formula I above.

In a preferred embodiment of the present invention the media according to the present invention comprise one more compounds of formula I-1, preferably selected from the group of compounds of formulae I-1a to I-1d, preferably one more compounds each of formula I-1a and/or I-1c, I-1a

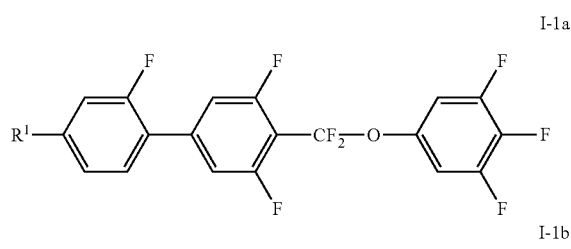

I-1b

I-1c

I-1d

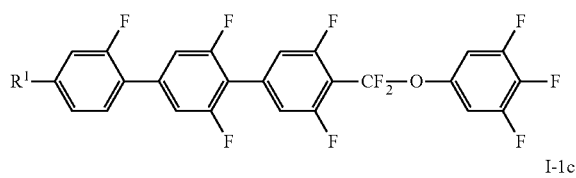

wherein $R^1$ has the meaning given under formula I-1 above and preferably is n-alkyl, most preferably ethyl, n-propyl, n-butyl, n-pentyl or n-hexyl.

In a preferred embodiment of the present invention the media according to the present invention comprise one more compounds of formula I-2, preferably selected from the group of compounds of formulae I-2a to I-2d, preferably one more compounds each of formula I-2c and/or I-2d, I-2a

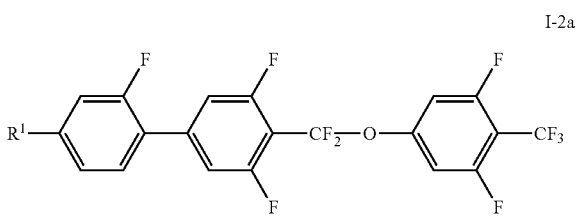

I-2b

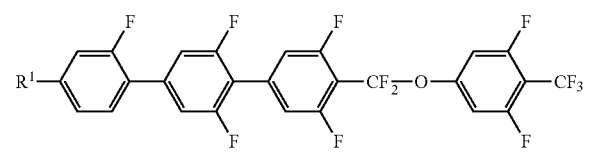

I-2c

I-2d

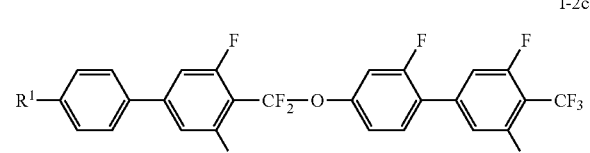

wherein $R^1$ has the meaning given under formula I-2 above and preferably is n-alkyl, most preferably ethyl, n-propyl, n-butyl, n-pentyl or n-hexyl.

In a preferred embodiment of the present invention the media according to the present invention comprise one more compounds of formula I-4, preferably selected from the group of compounds of formulae I-4a to I-4d, preferably one more compounds each of formula I-4a and/or I-4b, I-4a

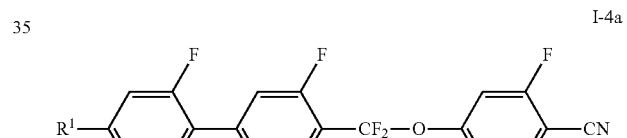

I-4b

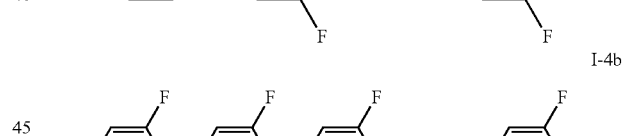

I-4c

I-4d

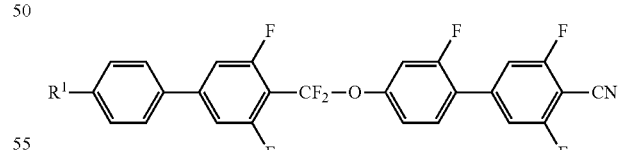

wherein $R^1$ has the meanings given under formula I-4 above and preferably is n-alkyl, most preferably ethyl, n-propyl, n-butyl, n-pentyl or n-hexyl.

In a preferred embodiment of the present invention the media according to the present invention additionally comprise one more compounds selected from the group of compounds of formulae II and III

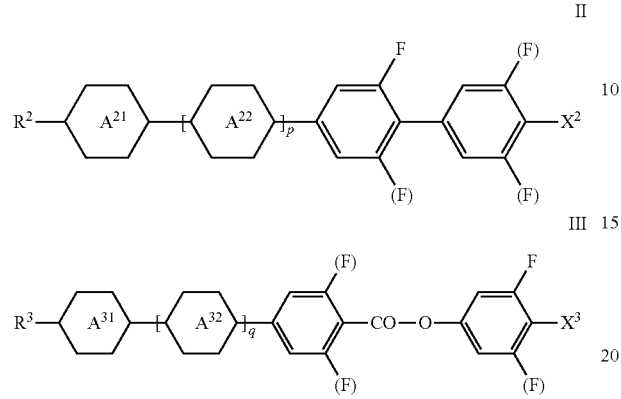

wherein

R² and R³ independently of each other have one of the meanings given for R¹ under formula I above X² and X³ are independently of each other F, Cl, CF₃, OCF₃ or CN, preferably by F, CF₃ or CN,

and, if present,

are independently of one another

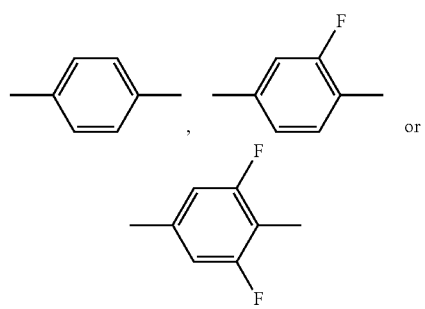

alternatively may be

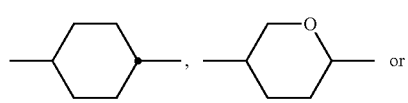

-continued

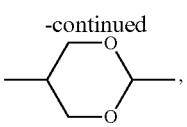

preferably

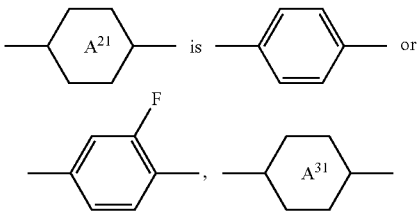

and, if present,

are independently of one another

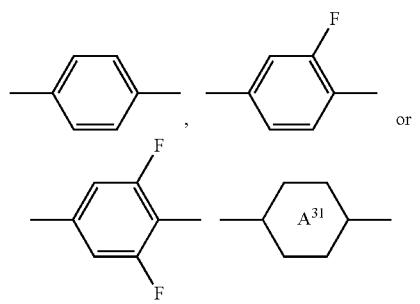

alternatively may be

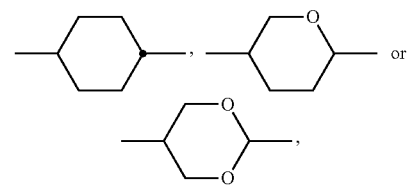

preferably

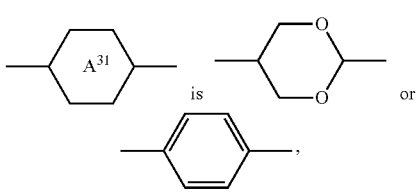

p is 0 or 1, preferably 0, and
q is 0 or 1, preferably 0.

Preferably the media according to the present invention additionally comprise one more compounds selected from the group of compounds of formulae IV and V

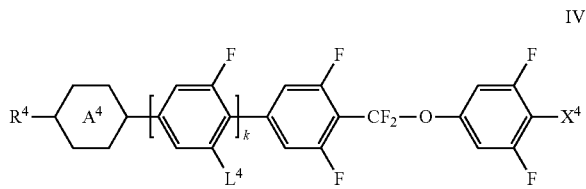

IV wherein
R⁴ is alkyl, which is straight chain or branched, preferably has 1 to 20 C-atoms, is unsubstituted, mono- or poly-substituted by F, Cl or CN, preferably by F, and in which one or more CH$_2$ groups are optionally replaced, in each case independently from one another, by —O—, —S—, —CO—, —COO—, —OCO—, —OCO—O—, —S—CO—, —CO—S— or —C≡C— in such a manner that O and/or S atoms are not linked directly to one another, preferably n-alkyl, n-alkoxy with 1 to 9 C-atoms, preferably 2 to 5 C-atoms, alkenyl, alkenyloxy or alkoxyalkyl with 2 to 9 C-atoms, preferably with 2 to 5 C-atoms, most preferably n-alkyl, n-alkoxy, alkenyl, alkenyloxy or alkoxyalkyl,
L⁴ is H or F, preferably H,

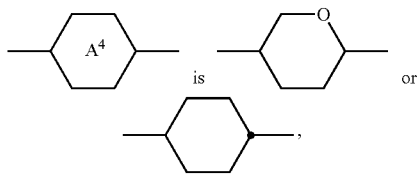

X⁴ is F, CF$_3$, OCF$_3$ or CN, preferably F, CF$_3$ or CN and most preferably F or CF$_3$, and
k is 0 or 1, preferably 1.

In a preferred embodiment of the present invention the mesogenic media comprise one more compounds of formula V

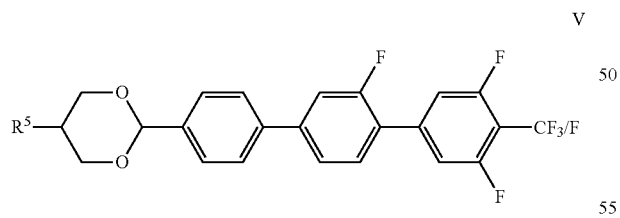

V wherein
R⁵ is alkyl, which is straight chain or branched, preferably has 1 to 20 C-atoms, is unsubstituted, mono- or poly-substituted by F, Cl or CN, preferably by F, and in which one or more CH$_2$ groups are optionally replaced, in each case independently from one another, by —O—, —S—, —CO—, —COO—, —OCO—, —OCO—O—, —S—CO—, —CO—S— or —C≡C— in such a manner that O and/or S atoms are not linked directly to one another, preferably n-alkyl, n-alkoxy with 1 to 9 C-atoms, preferably 2 to 5 C-atoms, alkenyl, alkenyloxy or alkoxyalkyl with 2 to 9 C-atoms, preferably with 2 to 5 C-atoms, more preferably n-alkyl, n-alkoxy, alkenyl, alkenyloxy or alkoxyalkyl, more preferably ethyl, n-propyl, n-butyl, n-pentyl or n-hexyl and most preferably n-butyl, and
X⁵ is F, CF$_3$, OCF$_3$ or CN, preferably F, CF$_3$ or CN and most preferably F or CF$_3$.

In a preferred embodiment of the present invention the mesogenic media comprise one more compounds of formula II, preferably a compound wherein R² has the meaning given under formula II above and more preferably is n-alkyl, more preferably ethyl, n-propyl, n-butyl, n-pentyl or n-hexyl and, most preferably n-butyl.

In a preferred embodiment of the present invention the mesogenic media comprise one more compounds of formula II, preferably selected from the group of compounds of its sub-formulae II-1 to II-8, preferably of formulae II-3 and/or II-7,

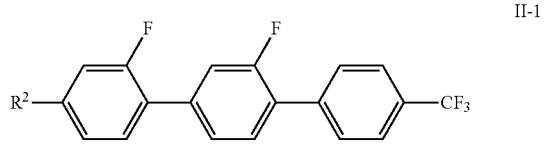

II-1

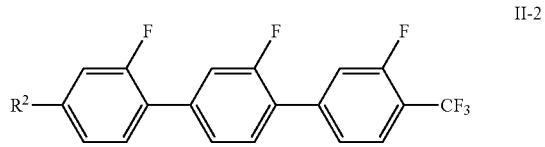

II-2

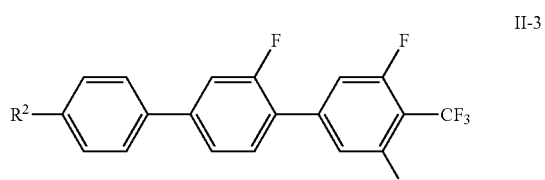

II-3

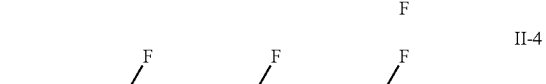

II-4

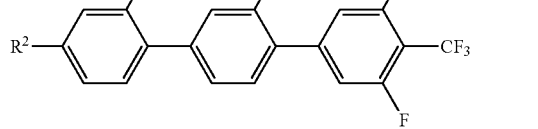

II-5

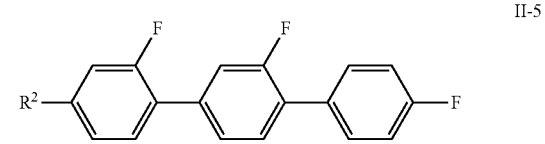

II-6

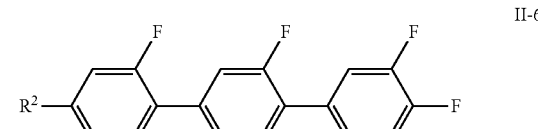

II-7

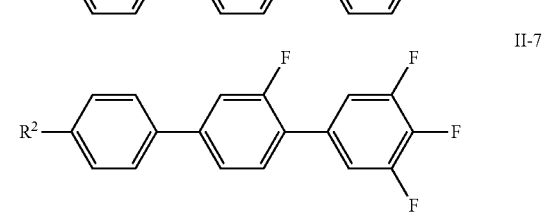

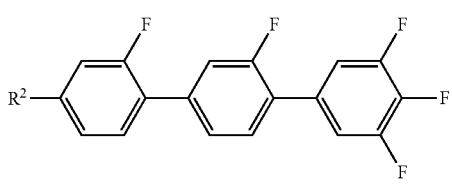

wherein R² has the meaning given under formula II above and preferably is n-butyl or n-pentyl.

In a preferred embodiment of the present invention the mesogenic media comprise one more compounds of formula III, preferably a compound wherein R³ has the meaning given under formula III above and more preferably is n-alkyl, more preferably ethyl, n-propyl, n-butyl, n-pentyl or n-hexyl and, most preferably n-butyl.

In a preferred embodiment of the present invention the mesogenic media comprise one more compounds of formula III, selected from the group of its sub-formulae III-1 to III-3, preferably of formulae III-1 and/or III-3,

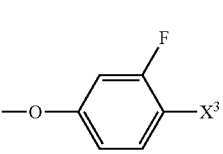

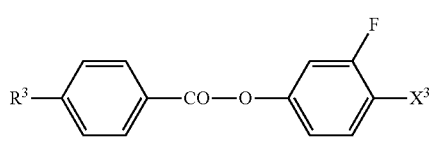

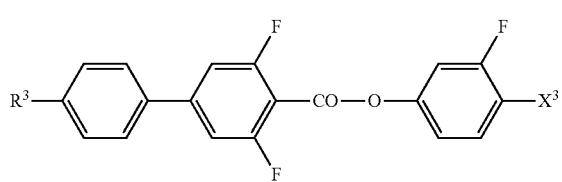

wherein the parameters have the meanings given above and preferably
X³ is F or CN
and in formulae III-1 and III-2 most preferably CN and in formula III-3 most preferably F.

An alkyl or an alkoxy radical, i.e. an alkyl where the terminal CH₂ group is replaced by —O—, in this application may be straight-chain or branched. It is preferably straight-chain, has 1, 2, 3, 4, 5, 6, 7 or 8 carbon atoms and accordingly is preferably methyl, ethyl, propyl, butyl, pentyl, hexyl, heptyl, octyl, ethoxy, propoxy, butoxy, pentoxy, hexoxy, heptoxy, or octoxy, furthermore nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. an alkyl group in which one non-terminal CH₂ group is replaced by —O—, is preferably straight-chain 2-oxapropyl (=methoxy-methyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

An alkenyl group, i.e. an alkyl group wherein one or more CH₂ groups are replaced by —CH=CH—, may be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are C₂-C₇-1E-alkenyl, C₄-C₇-3E-alkenyl, C₅-C₇-4-alkenyl, C₆-C₇-5-alkenyl and C₇-6-alkenyl, in particular C₂-C₇-1E-alkenyl, C₄-C₇-3E-alkenyl and C₅-C₇-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C-atoms are generally preferred.

In an alkyl group, wherein one CH₂ group is replaced by —O— and one by —CO—, these radicals are preferably neighboured. Accordingly these radicals together form a carbonyloxy group —CO—O— or an oxycarbonyl group —O—CO—. Preferably such an alkyl group is straight-chain and has 2 to 6 C atoms.

It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxy-ethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxy-carbonylmethyl, propoxycarbonylmethyl, butoxycarbonylmethyl, 2-(methoxycarbonyl)ethyl, 2-(ethoxycarbonyl)ethyl, 2-(propoxy-carbonyl) ethyl, 3-(methoxycarbonyl)propyl, 3-(ethoxycarbonyl) propyl, 4-(methoxycarbonyl)-butyl.

An alkyl group wherein two or more CH₂ groups are replaced by —O— and/or —COO—, it can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A alkyl or alkenyl group that is monosubstituted by CN or CF₃ is preferably straight-chain. The substitution by CN or CF₃ can be in any desired position.

An alkyl or alkenyl group that is at least monosubstituted by halogen, it is preferably straight-chain. Halogen is preferably F or Cl, in case of multiple substitutions preferably F. The resulting groups include also perfluorinated groups. In case of monosubstitution the F or Cl substituent can be in any desired position, but is preferably in ω-position. Examples for especially preferred straight-chain groups with a terminal F substituent are fluoromethyl, 2-fluoroethyl, 3-fluoropropyl, 4-fluorobutyl, 5-fluoropentyl, 6-fluorohexyl and 7-fluoroheptyl. Other positions of F are, however, not excluded.

Halogen means F, Cl, Br and I and is preferably F or Cl, most preferably F. Each of $R^1$ to $R^5$, R, R' and R" may be a polar or a non-polar group. In case of a polar group, it is preferably selected from CN, $SF_5$, halogen, $OCH_3$, SCN, $COR^5$, $COOR^5$ or a mono-oligo- or polyfluorinated alkyl or alkoxy group with 1 to 4 C atoms. $R^5$ is optionally fluorinated alkyl with 1 to 4, preferably 1 to 3 C atoms. Especially preferred polar groups are selected of F, Cl, CN, $OCH_3$, $COCH_3$, $COC_2H_5$, $COOCH_3$, $COOC_2H_5$, $CF_3$, $CHF_2$, $CH_2F$, $OCF_3$, $OCHF_2$, $OCH_2F$, $C_2F_5$ and $OC_2F_5$, in particular F, Cl, CN, $CF_3$, $OCHF_2$ and $OCF_3$. In case of a non-polar group, it is preferably alkyl with up to 15 C atoms or alkoxy with 2 to 15 C atoms.

Each of $R^1$ to $R^5$, R, R, R' and R" may be an achiral or a chiral group. In case of a chiral group it is preferably of formula I*:

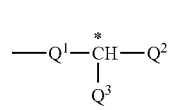

I* wherein
$Q^1$ is an alkylene or alkylene-oxy group with 1 to 9 C atoms or a single bond,
$Q^2$ is an alkyl or alkoxy group with 1 to 10 C atoms which may be unsubstituted, mono- or polysubstituted by F, Cl, Br or CN, it being also possible for one or more non-adjacent $CH_2$ groups to be replaced, in each case independently from one another, by —C≡C—, —O—, —S—, —NH—, —N($CH_3$)—, —CO—, —COO—, —OCO—, —OCO—O—, —S—CO— or —CO—S— in such a manner that oxygen atoms are not linked directly to one another,
$Q^3$ is F, Cl, Br, CN or an alkyl or alkoxy group as defined for $Q^2$ but being different from $Q^2$.

In case $Q^1$ in formula I* is an alkylene-oxy group, the 0 atom is preferably adjacent to the chiral C atom.

Preferred chiral groups of formula I* are 2-alkyl, 2-alkoxy, 2-methylalkyl, 2-methylalkoxy, 2-fluoroalkyl, 2-fluoroalkoxy, 2-(2-ethin)-alkyl, 2-(2-ethin)-alkoxy, 1,1,1-trifluoro-2-alkyl and 1,1,1-trifluoro-2-alkoxy.

Particularly preferred chiral groups I* are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

In addition, compounds containing an achiral branched alkyl group may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl-propoxy and 3-methylbutoxy.

Preferably the liquid crystalline media according to the present invention comprise one or more reactive compounds, respectively polymerisable compounds, each comprising one, two ore more reactive groups, respectively polymerizable groups. This is obvious, as the mesogenic material preferably is stabilized in the blue phase by the formation of a polymer, which may have the form of a matrix or of a network.

For use in a display application, the temperature range of typical materials, which are exhibiting a pure blue phase (BP) on their own, generally is not wide enough. Such materials typically have a blue phase, which extends over a small temperature range of only some degrees, e.g. about 3 to 4°. Thus, an additional stabilisation, extending the temperature range of the blue phase, is needed in order to make such materials suitable for practical applications such as in displays.

In order to stabilise the blue phase by the formation of a polymer, the formulated blue phase host mixture is conveniently combined with an appropriate chiral dopant (one or more suitable chiral compounds) and with one or more reactive compounds, preferably reactive mesogenic compounds (RMs). The resultant mixture is filled into the LC cell, respectively a display panel. The LC cell/panel is then held at a certain temperature at which the mixture is in the blue phase, e.g. it is heated or cooled until blue phase can be observed at a certain temperature. This temperature is maintained during the whole polymerisation process. The polymerisation process is typically controlled by UV irradiation of a typical medium-pressure mercury-vapour lamp. A standard condition is e.g. use of 3 mW/cm$^2$ for 180 sec. at a wavelength of 380 nm. To avoid damage to the LC material appropriate optical filters can be used additionally.

In the following the criteria for stability of the obtained polymer stabilised blue phase (BP) are briefly be explained.

Ensuring an excellent quality of the polymer stabilisation is critical for use of PS-BP in a display application. The quality of polymer stabilization is the judged by several criteria. Optical inspection ensures a good polymerisation. Any defect and/or haziness observed in the test cell/panel is an indication of a suboptimal polymer stabilisation. Electro-optical inspection under various load/stress conditions ensures long-time stability of the PS-BP. A typical display parameter is the so-called memory effect (ME). The memory effect is defined as the ratio of the contrast ratio for switching on and of the contrast ratio for switching off as a normalized measure of the residual transmission after one or more switching cycles have been executed. A value for this memory effect of 1.0 is an indicator of an excellent polymer stabilisation. A value for this memory effect of more than 1.1 indicates insufficient stabilisation of the blue phase.

The present invention further relates to an LC medium comprising one or more compounds selected from the group of the compounds of the formulae I and II and optionally III, a chiral dopant and one or more compounds of the formula P $$P^a\text{-}(Sp^a)_{s1}\text{-}(A^1\text{-}Z^1)_{n1}\text{-}A^2\text{-}Q\text{-}A^3\text{-}(Z^4\text{-}A^4)_{n2}\text{-}(Sp^b)_{s2}\text{-}P^b \qquad P$$

wherein the individual radicals have the following meanings:
$P^a$, $P^b$ each, independently of one another, are a polymerisable group,
$Sp^a$, $Sp^b$ each, independently of one another, denote a spacer group, s1, s2 each, independently of one another, denote 0 or 1,
n1, n2 each, independently of one another, denote 0 or 1, preferably 0, Q denotes —CF$_2$O—, —OCF$_2$—, —CH$_2$O—, —OCH$_2$—, —(CO)O—, —O(CO)—, —(CH$_2$)$_4$—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —(CH$_2$)$_3$O—, —O(CH$_2$)$_3$—, —CH=CF—, —C≡C—, —O—, —CH$_2$—, —(CH$_2$)$_3$—, —CF$_2$—, preferably —CF$_2$O—, Z$^1$, Z$^4$ denote a single bond, —CF$_2$O—, —OCF$_2$—, —CH$_2$O—, —OCH$_2$—, —(CO)O—, —O(CO)—, —(CH$_2$)$_4$—, —CH$_2$CH$_2$—, —CF$_2$—CF$_2$—, —CF$_2$—CH$_2$—, —CH$_2$—CF$_2$—, —CH=CH—, —CF=CF—, —CF=CH—, —(CH$_2$)$_3$O—, —O(CH$_2$)$_3$—, —CH=CF—, —C≡C—, —O—, —CH$_2$—, —(CH$_2$)$_3$—, —CF$_2$—, where Z$^1$ and Q or Z$^4$ and Q do not simultaneously denote a group selected from —CF$_2$O— and —OCF$_2$—, A$^1$, A$^2$, A$^3$, A$^4$
each, independently of one another, denotes a radical selected from the following groups:
a) the group consisting of trans-1,4-cyclohexylene, 1,4-cyclohexenylene and 1,4'-bicyclohexylene, in which, in addition, one or more non-adjacent CH$_2$ groups may be replaced by —O— and/or —S— and in which, in addition, one or more H atoms may be replaced by F,
b) the group consisting of 1,4-phenylene and 1,3-phenylene, in which, in addition, one or two CH groups may be replaced by N and in which, in addition, one or more H atoms may be replaced by L,
c) the group consisting of tetrahydropyran-2,5-diyl, 1,3-dioxane-2,5-diyl, tetrahydrofuran-2,5-diyl, cyclobutane-1,3-diyl, piperidine-1,4-diyl, thiophene-2,5-diyl and selenophene-2,5-diyl, each of which may also be mono- or polysubstituted by L,
d) the group consisting of saturated, partially unsaturated or fully unsaturated, and optionally substituted, polycyclic radicals having 5 to 20 cyclic C atoms, one or more of which may, in addition, be replaced by heteroatoms, preferably selected from the group consisting of bicyclo[1.1.1]pentane-1,3-diyl, bicyclo[2.2.2]octane-1,4-diyl, spiro[3.3]heptane-2,6-diyl,

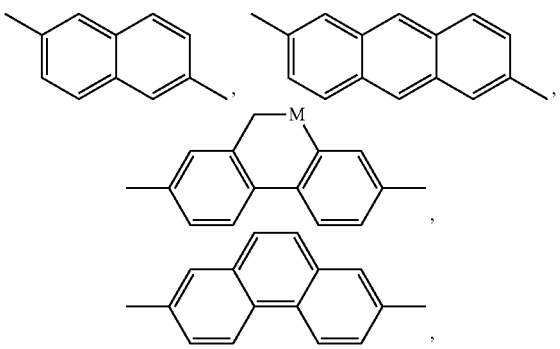

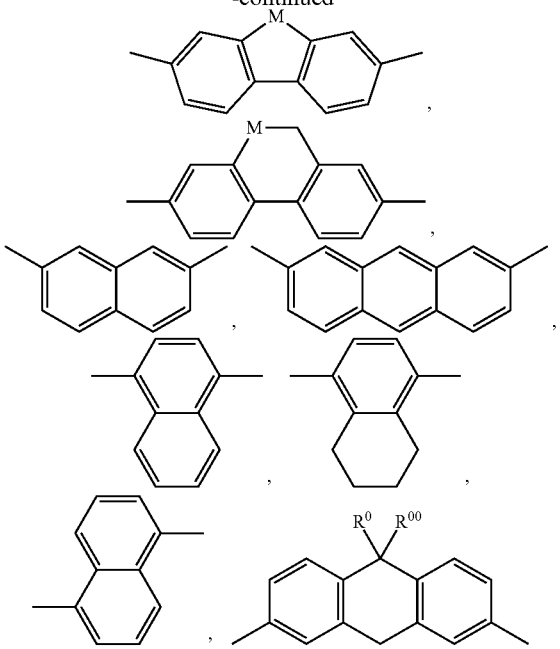

where, in addition, one or more H atoms in these radicals may be replaced by L, and/or one or more double bonds may be replaced by single bonds, and/or one or more CH groups may be replaced by N, L on each occurrence, identically or differently, denotes F, Cl, CN, SCN, SF$_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms, R$^0$, R$^{00}$ each, independently of one another, denote H, F or straight-chain or branched alkyl having 1 to 12 C atoms, in which, in addition, one or more H atoms may be replaced by F, M denotes —O—, —S—, —CH$_2$—, —CHY$^1$— or —CY$^1$Y$^2$—, and Y$^1$ and Y$^2$ each, independently of one another, have one of the meanings indicated above for R$^0$, or denote Cl or CN, and one of the groups Y$^1$ and Y$^2$ alternatively denotes —OCF$_3$, preferably H, F, Cl, CN or CF$_3$, as well as to a polymer stabilized system obtainable by polymerisation of one or more compounds of the formula P alone or in combination with on or more further polymerisable compounds from a respective mixture, and to the use of such a stabilized system in electro-optical displays having a blue phase.

Compounds of the formula P, preferably used according to the present invention, are selected from the group consisting of the following formulae:

P1

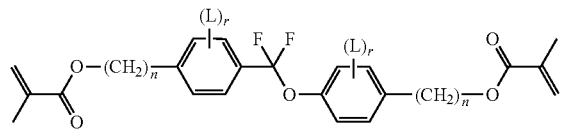

P2

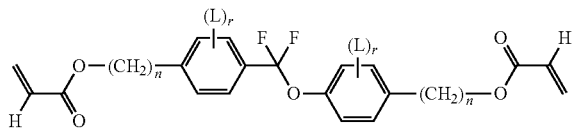

-continued
P3
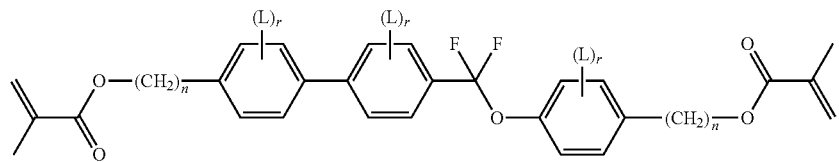
P4
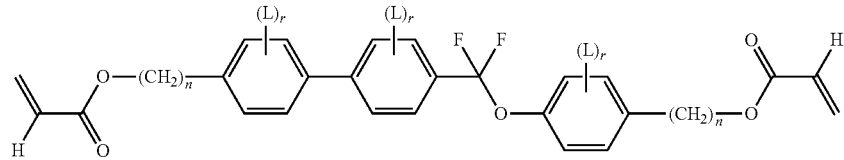
P5
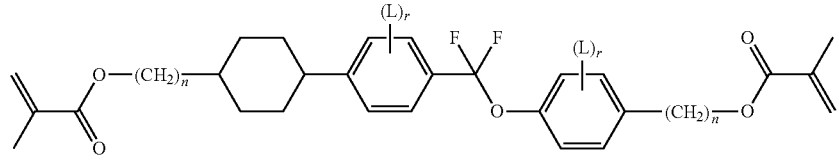
P6
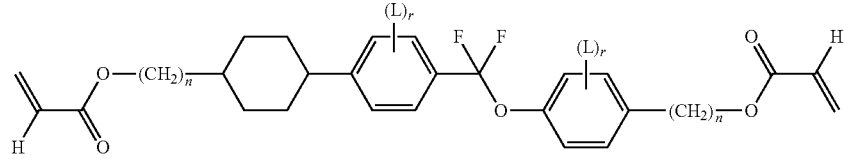
P7  P8
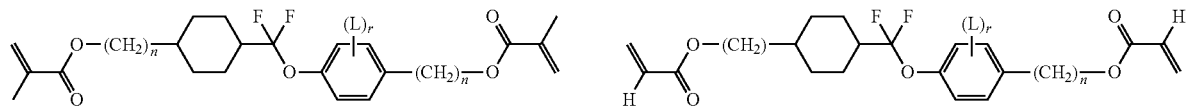
P9
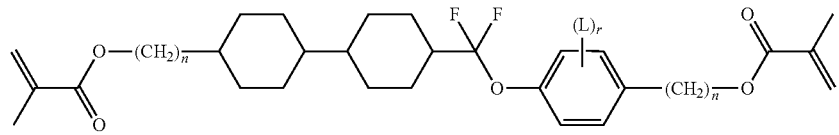
P10
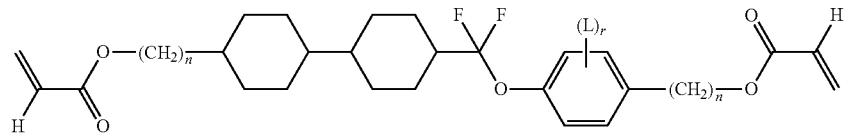
P11
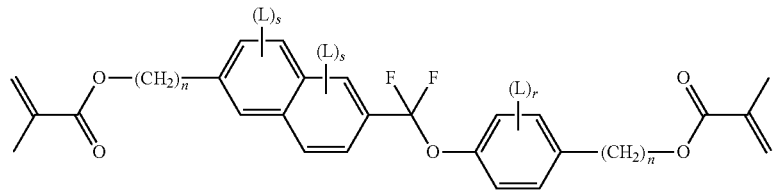
P12
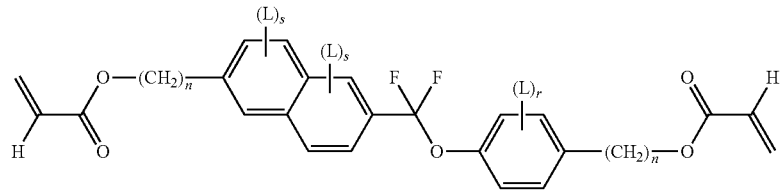

-continued
P13
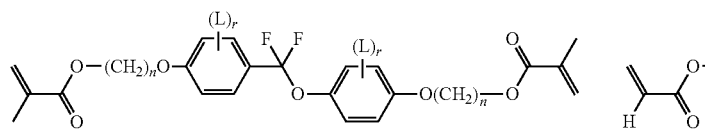
P14
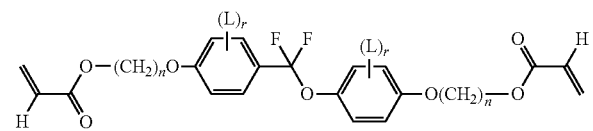
P15
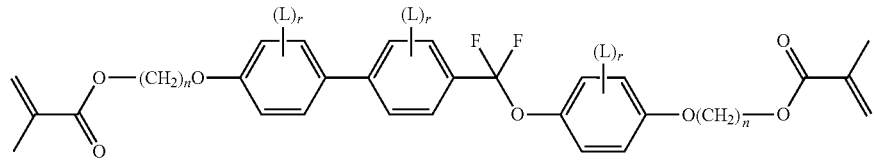
P16
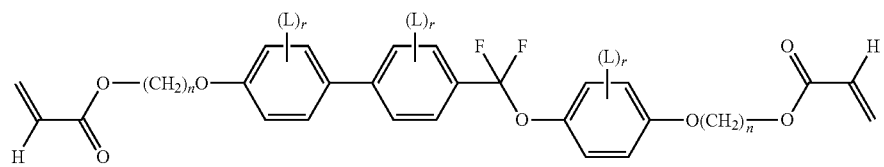
P17
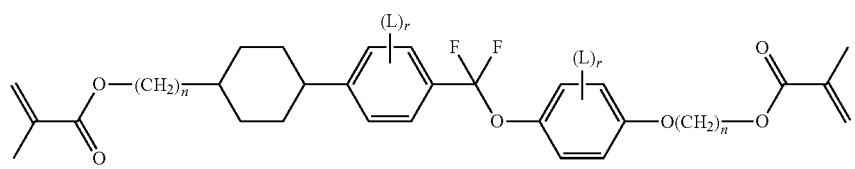
P18
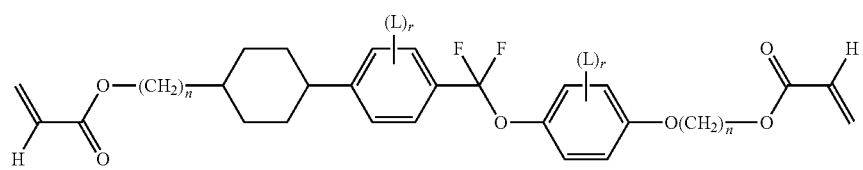
P19 P20
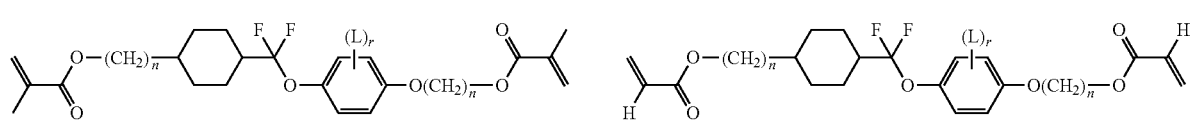
P21
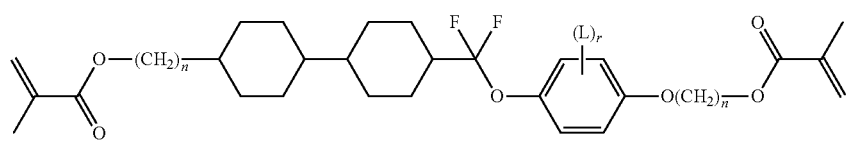
P22
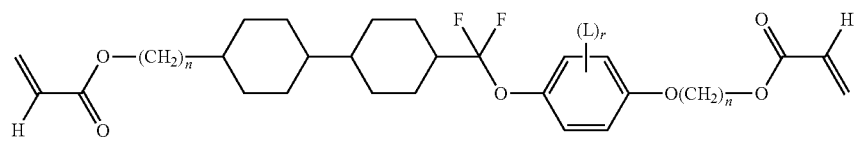
P23
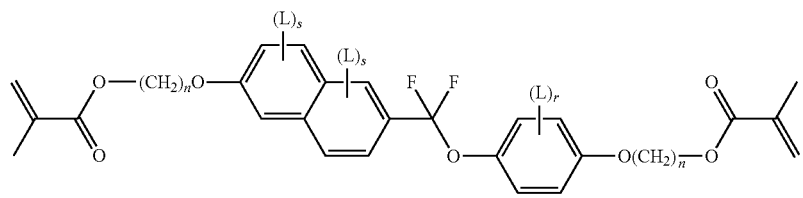

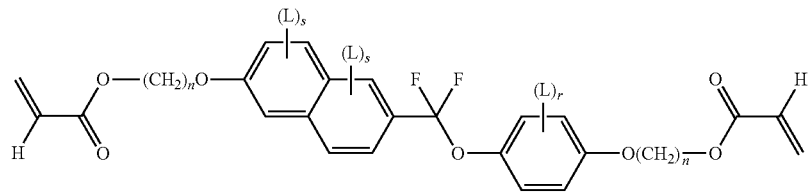

P24 in which L in each occurrence, identically or differently, has one of the meanings indicated above and below, r denotes 0, 1, 2, 3 or 4, s denotes 0, 1, 2 or 3, and n denotes an integer between 1 and 24, preferably between 1 and 12, very particularly preferably between 2 and 8, and in which, if a radical is not indicated at the end of a single or double bond, it is a terminal $CH_3$ or $CH_2$ group.

In the formulae P1 to P24,

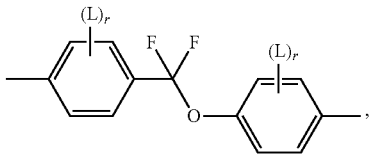

preferably denotes a group selected from the group consisting of the following formulae:

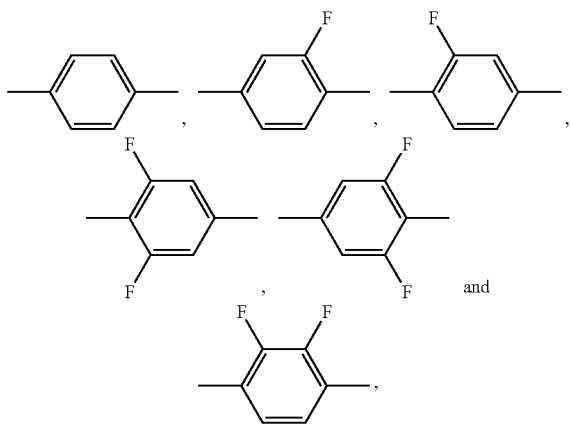

particularly preferably

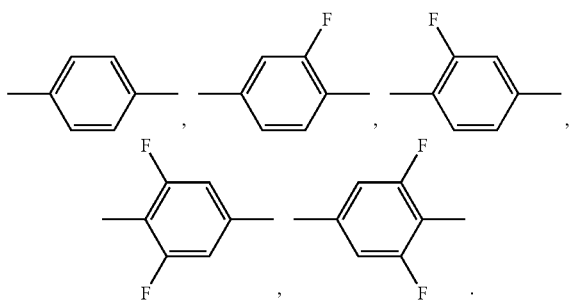

The group $A^2$-Q-$A^3$ preferably denotes a group of the formula

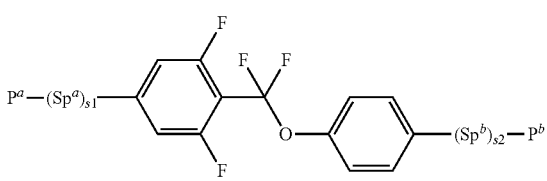

in which at least one of the rings is substituted by at least one group L=F. r here is in each case, independently, preferably 0, 1 or 2.

$P^a$ and $P^b$ in the compounds of the formula P and the sub-formulae thereof preferably denote acrylate or methacrylate, furthermore fluoroacrylate. $Sp^a$ and $Sp^b$ in the compounds of the formula I and the sub-formulae thereof preferably denote a radical selected from the group consisting of —$(CH_2)_{p1}$—, —$(CH_2)_{p1}$—O—, —$(CH_2)_{p1}$—O—CO— and —$(CH_2)_{p1}$—O—CO—O— and mirror images thereof, in which p1 denotes an integer from 1 to 12, preferably from 1 to 6, particularly preferably 1, 2 or 3, where these groups are linked to $P^a$ or $P^b$ in such a way that O atoms are not directly adjacent.

Of the compounds of the formula P, particular preference is given to those in which the radicals $P^a$ and $P^b$ are selected from the group consisting of vinyloxy, acrylate, methacrylate, fluoroacrylate, chloroacrylate, oxetane and epoxide groups, particularly preferably acrylate or methacrylate groups, the radicals $Sp^a$ and $Sp^b$ are selected from the group consisting of —$(CH_2)_{p1}$—, —$(CH_2)_{p1}$—O—, —$(CH_2)_{p1}$—O—CO— and —$(CH_2)_{p1}$—O—CO—O— and mirror images thereof, in which p1 denotes an integer from 1 to 12, preferably from 1 to 6, particularly preferably 1, 2 or 3, and where these radicals are linked to $P^a$ or $P^b$ in such a way that O atoms are not directly adjacent, Compounds of formula P, preferably used according to a preferred embodiment of the instant invention, are those comprising exactly two rings (n1=n2=0), which are preferably 6-membered rings. Especially preferred are compounds selected from the group of compounds of the following formulae:

Pa

Pb
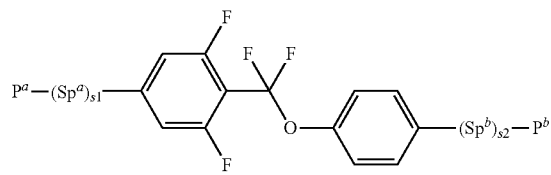
Pc
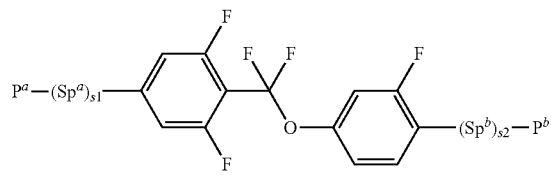
Pd
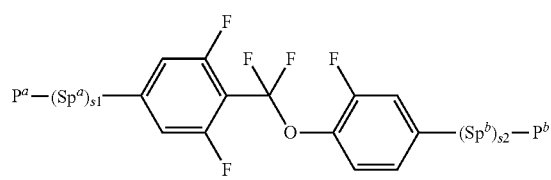
Pe
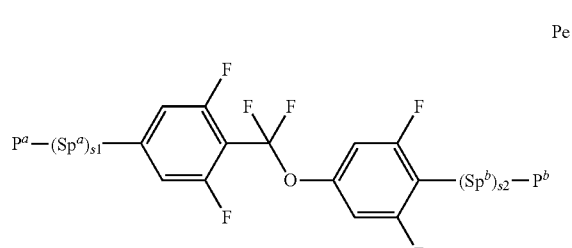
Pf
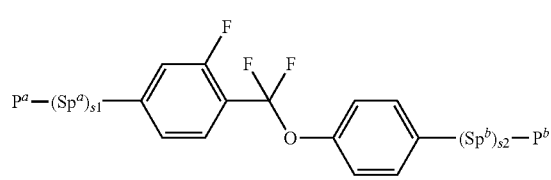
Pg
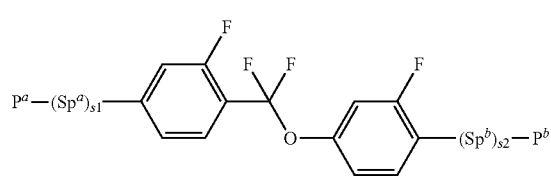
Ph
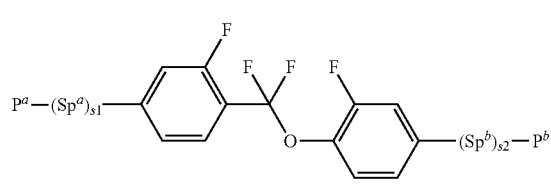
Pi
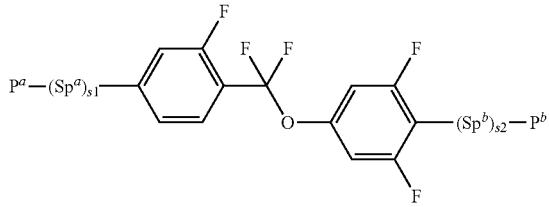
Pk
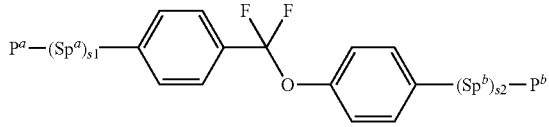
Pl
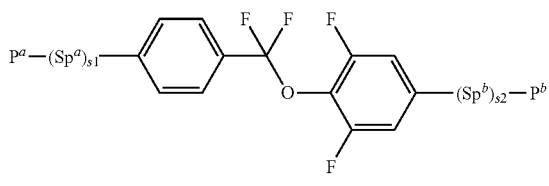
Pm
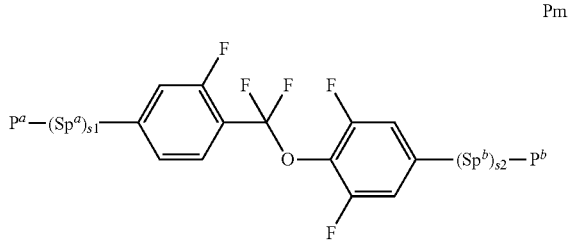
Pn
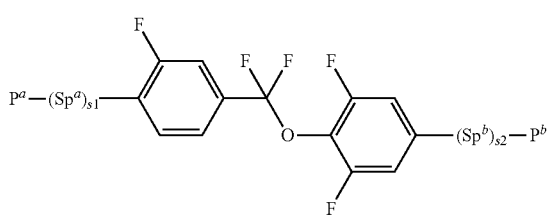
Po
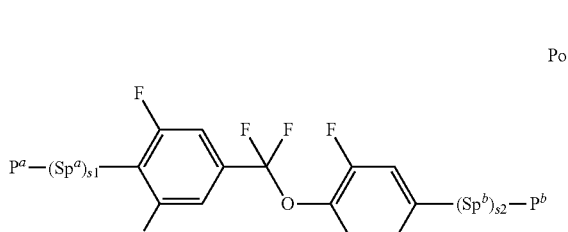
Pp
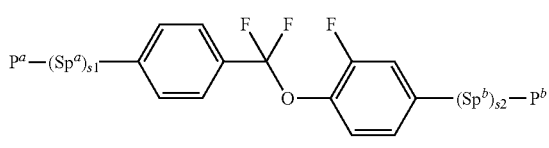

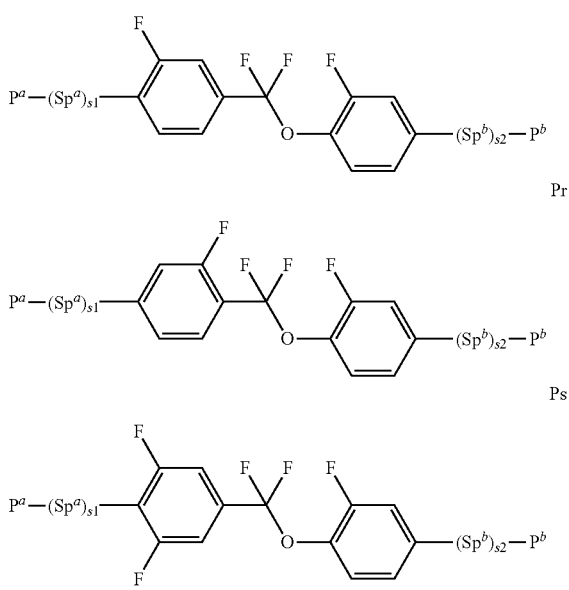

wherein $P^a$, $P^b$, $Sp^a$, $Sp^b$, s1 and s2 are as defined under formula P above, and preferably $Sp^{a/b}$ is alkylene —$(CH_2)_n$— wherein n preferably is 3, 4, 5, 6 or 7 and $P^{a/b}$ a methacrylat- or acrylate moiety. Especially preferred is the use of compounds selected from the group of formulae Pa, Pb, Pc, Pd, Pe, Pf, Pg, Ph and Pi, and in particular the compounds of formula Pa.

The moiety "$A^2$-$Q^1$-$A^3$" preferably is a moiety of formula

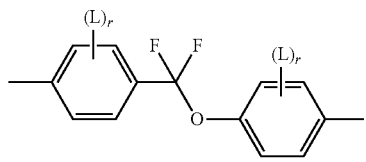

wherein preferably at least one of the two phenylene rings is substituted by at least one L, which is different from H, wherein r is independently for each ring, and preferably it is for each ring 0, 1 or 2.

For the compounds of formula P, as well as for its respective sub-formulae, preferably $P^a$ and $P^b$ are, independently from each other, acrylate or methacrylate, but also fluoroacrylate, $Sp^a$ and $Sp^b$ are, independently from each other, —$(CH_2)_{p1}$—, —$(CH_2)_{p1}$—O—, —O—$(CH_2)_{p1}$—, —$(CH_2)_{p1}$—O—CO—, —CO—O—$(CH_2)_{p1}$—, —$(CH_2)_{p1}$—O—CO—O— or —$(CH_2)_{p1}$—O—CO—O—, wherein p1 is an integer from 1 to 12, preferably from 1 to 6, particularly preferred 1, 2 or 3, and wherein these moieties are liked with $P^a$ or $P^b$ in such a way that no O-atoms are linked directly to on another.

Especially preferred is the use of compounds of formula P, wherein $P^a$ and $P^b$ are vinyleoxy-, acrylate-, methacrylata-, fluoroacrylate-, chloroacrylate-, oxetane- or an epoxy group, particularly preferred acrylate- or methacrylate, $Sp^a$ and $Sp^b$ are —$(CH_2)_{p1}$—, —$(CH_2)_{p1}$—O—, —O—$(CH_2)_{p1}$—, —$(CH_2)_{p1}$—O—CO—, —CO—O—$(CH_2)_{p1}$—, —$(CH_2)_{p1}$—O—CO—O— or —$(CH_2)_{p1}$—O—CO—O—, wherein p1 is an integer from 1 to 12, preferably from 1 to 6, particularly preferred 1, 2 or 3, and wherein these moieties are liked with $P^a$ or $P^b$ in such a way that no O-atoms are linked directly to on another.

For the production of polymer stabilised displays according to the present invention, the polymerisable compounds are polymerised or cross-linked, in case one compound contains or more compounds contain two or more polymerisable groups, by in-situ polymerisation in the LC medium between the substrates of the LC display with application of a voltage. The polymerisation can be carried out in one step. It is also possible firstly to carry out the polymerisation with application of a voltage in a first step in order to generate a pretilt angle, and subsequently, in a second polymerisation step without an applied voltage, to polymerise or crosslink the compounds which have not reacted in the first step ("end curing").

Suitable and preferred polymerisation methods are, for example, thermal or photopolymerisation, preferably photopolymerisation, in particular UV photopolymerisation. One or more initiators can optionally also be added here. Suitable conditions for the polymerisation and suitable types and amounts of initiators are known to the person skilled in the art and are described in the literature. Suitable for free-radical polymerisation are, for example, the commercially available photoinitiators Irgacure651® (short IRG-651®), Irgacure184®, Irgacure907®, Irgacure369® or Darocure1173® (Ciba AG). If an initiator is employed, its proportion is preferably 0.001 to 5% by weight, particularly preferably 0.001 to 1% by weight.

The polymerisable compounds according to the invention are also suitable for polymerisation without an initiator, which is accompanied by considerable advantages, such as, for example, lower material costs and in particular less contamination of the LC medium by possible residual amounts of the initiator or degradation products thereof. The polymerisation can thus also be carried out without the addition of an initiator. In a preferred embodiment, the LC medium thus comprises no polymerisation initiator.

The polymerisable component or the LC medium may also comprise one or more stabilisers in order to prevent undesired spontaneous polymerisation of the RMs, for example during storage or transport. Suitable types and amounts of stabilisers are known to the person skilled in the art and are described in the literature. Particularly suitable are, for example, the commercially available stabilisers from the Irganox® series (Ciba AG), such as, for example, Irganox® 1076. If stabilisers are employed, their proportion, based on the total amount of RMs or the polymerisable component, is preferably in the range from 10 to 10,000 ppm, particularly preferably in the range from 50 to 500 ppm.

The polymerisable compounds of formula P used preferably according to the present invention can be polymerised individually, but it is also possible to polymerise mixtures which comprise two or more polymerisable compounds according to the invention, or mixtures comprising one or more polymerisable compounds according to the invention and one or more further polymerisable compounds (co-monomers), which are preferably mesogenic or liquid-crystalline. In the case of polymerisation of such mixtures, copolymers form. A mixture of two or more compounds according to the invention or a mixture comprising one or more compounds according to the invention with one or more further polymerisable compounds is preferably used. The invention furthermore relates to the polymerisable mixtures mentioned above and below. The polymerisable compounds and co-monomers are mesogenic or non-mesogenic, preferably mesogenic or liquid-crystalline.
Suitable and preferred co-monomers for use in polymer precursors for polymer stabilised displays according to the invention are selected, for example, from the following formulae:
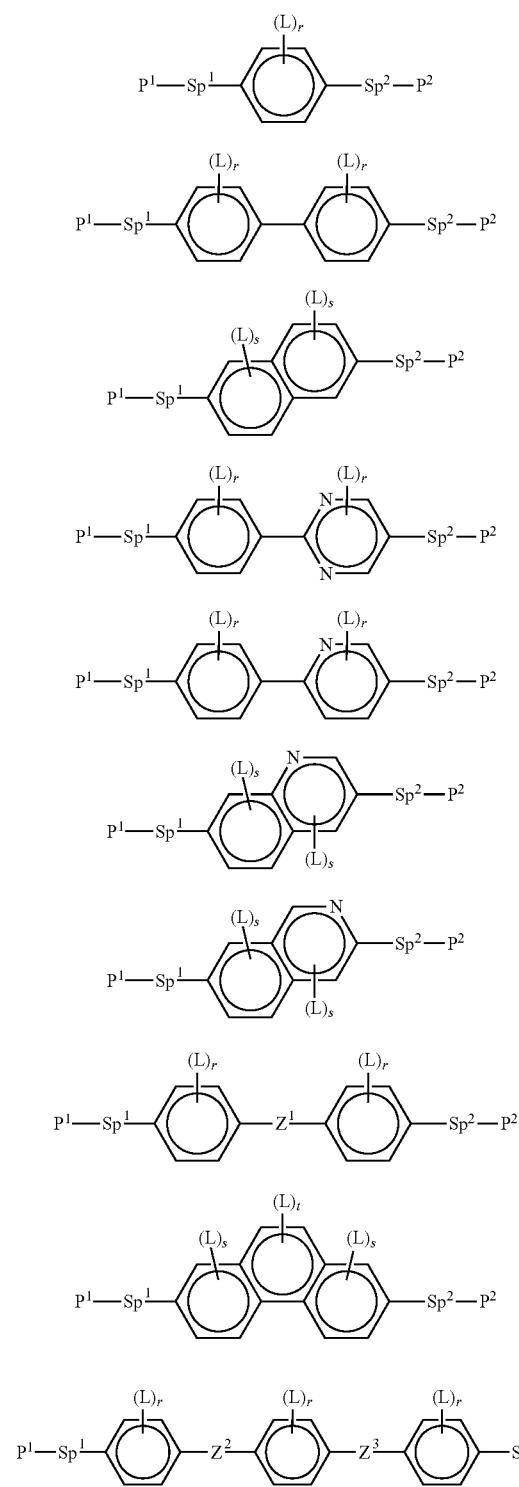
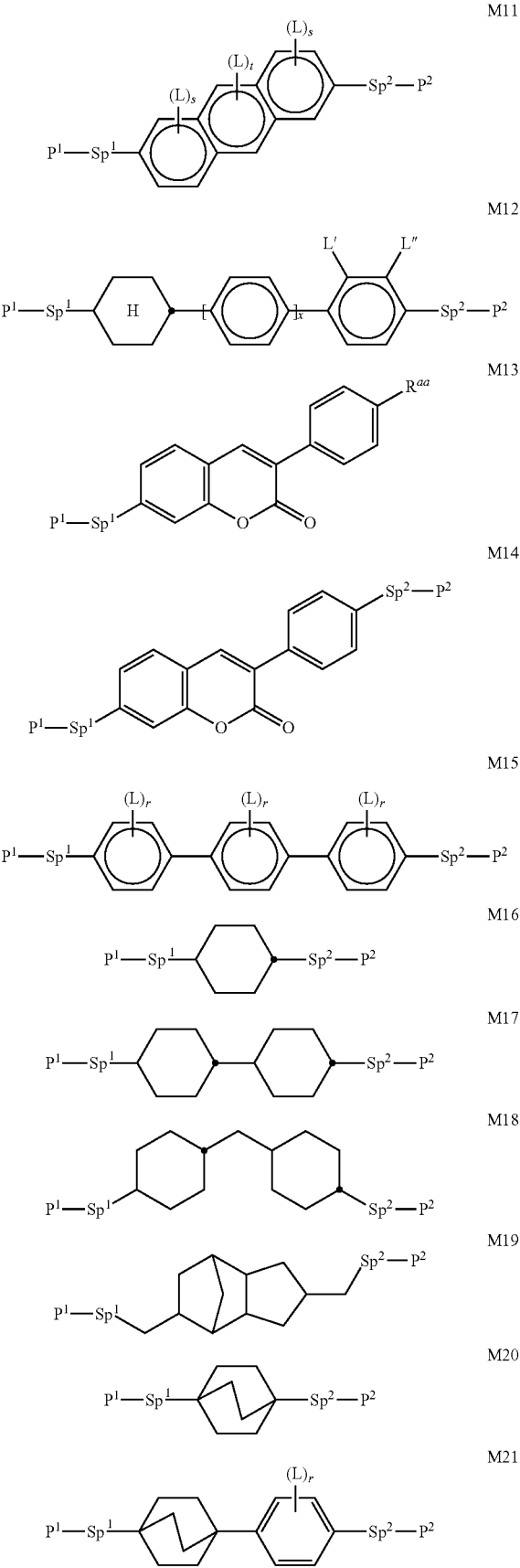

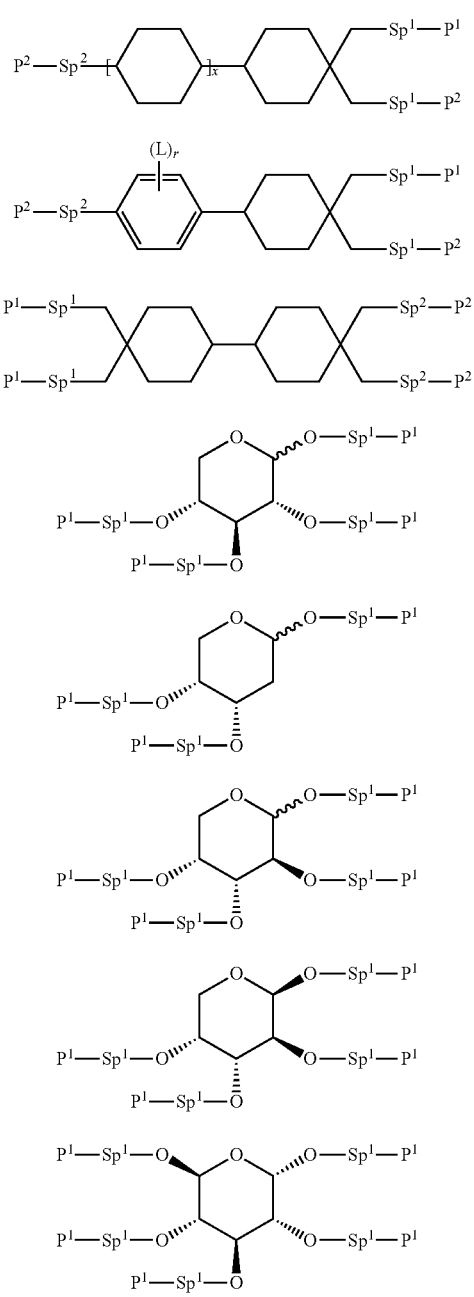

wherein the parameters have the following meanings:

$P^1$ and $P^2$ each, independently of one another, a polymerisable group, preferably having one of the meanings given above or below for $P^a$, particularly preferred an acrylate, methacrylate, fluoroacrylate, oxetane, vinyloxy- or epoxy group, $Sp^1$ and $Sp^2$ each, independently of one another, a single bond or a spacer group, preferably having one of the meanings given above or below for $Sp^a$, particularly preferred an —$(CH_2)_{p1}$—, —$(CH_2)_{p1}$—O—, —$(CH_2)_{p1}$—CO—O— or —$(CH_2)_{p1}$—O—CO—O—, wherein p1 is an integer from 1 to 12, and wherein the groups mentioned last are linked to the adjacent ring via the O-atom, and, wherein alternatively also one or more of $P^1$-$Sp^1$- and $P^2$-$Sp^2$- may be $R^{aa}$, provided that at least one of $P^1$-$Sp^1$- and $P^2$-$Sp^2$- present in the compound is not $R^{aa}$, $R^{aa}$ H, F, Cl, CN or linear or branched alkyl having 1 to 25 C-atoms, wherein one or more non-adjacent —$CH_2$— groups, independently of each another, may be replaced by —C($R^0$)=C($R^{00}$)—, —C≡C—, —N($R^0$)—, —O—, —S—, —CO—, —CO—O—, —O—CO—, —O—CO—O— in such a way that neither O- nor S-atoms are directly linked to one another, and wherein also one or more H-atoms may be replaced by F, Cl, CN or $P^1$-$Sp^1$-, particularly preferred linear or branched, optionally single- or polyfluorinated, alkyl, alkoxy, alkenyl, alkinyl, alkylcarbonyl, alkoxycarbonyl, or alkylcarbonyloxy having 1 to 12 C-atoms, wherein the alkenyl- and alkinyl groups have at least two and the branched groups have at least three C-atoms, $R^0$, $R^{00}$ each, at each occurrence independently of one another, H or alkyl having 1 to 12 C-atoms, $R^y$ and $R^z$ each, independently of one another, H, F, $CH_3$ or $CF_3$, $Z^1$ —O—, —CO—, —C($R^y R^z$)—, or —$CF_2 CF_2$—, $Z^2$ and $Z^3$ each, independently of one another, —CO—O—, —O—CO—, —$CH_2$O—, —$OCH_2$—, —$CF_2$O—, —$OCF_2$—, or —$(CH_2)_n$—, wherein n is 2, 3 or 4, L at each occurrence independently of one another, F, Cl, CN, SCN, $SF_5$ or linear or branched, optionally mono- or poly-fluorinated, alkyl, alkoxy, alkenyl, alkinyl, alkylcarbonyl, alkoxycarbonyl, alkylcarbonyloxy or alkoxycarbonyloxy having 1 to 12 C-atoms, preferably F, L' and L" each, independently of one another, H, F or Cl, r 0, 1, 2, 3 or 4, s 0, 1, 2 or 3, t 0, 1 or 2, and x 0 or 1.

Suitable and preferred co-monomers for use in displays according to the present application operable and/or operating at a temperature where the mesogenic medium is in the blue are for example selected from the group of mono-reactive compounds, which are present in the precursor of the polymer stabilised systems in a concentration in the range from 1 to 9 wt.-%, particularly preferred from 4 to 7 wt.-%. Preferred mono-reactive compounds are the compounds of formulae M1 to M29, wherein one or more of $P^1$-$Sp^1$- and $P^2$-$Sp^2$- are $R^{aa}$, such that the compounds have a single reactive group only.

Particularly preferred mono-reactive compounds are the compounds of the following formulae

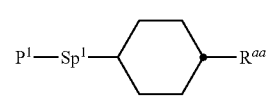

M16-A

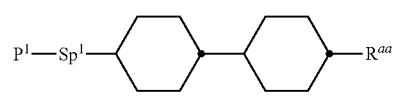

M17-A wherein $P^1$, $Sp^1$ and $R^{aa}$ have the respective meanings given above.

Amongst these the compounds of the formula

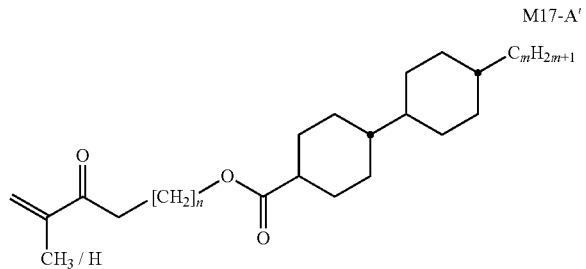

M17-A' wherein
n is an integer, preferably an even integer, in the range from 1 to 16, preferably from 2 to 8,
m is an integer in the range from 1 to 15, preferably from 2 to 7, are especially preferred.

Particular preference is given to an LC medium, an LC display, a process or the use as described above and below, in which the LC medium or the polymerisable or polymerised component present therein comprises one or more compounds of the following formula:

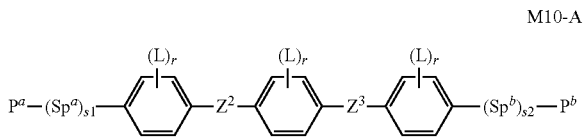

M10-A in which $P^a$, $P^b$, $Sp^a$, $Sp^b$, s1, s2 and L have the meanings indicated above and below, r denotes 0, 1, 2, 3 or 4, and $Z^2$ and $Z^3$ each, independently of one another, denote —$CF_2$—O— or —O—$CF_2$—, preferably $Z^2$ is —$CF_2$—O— and $Z^3$ is —O—$CF_2$— or vice versa, and, most preferably, $Z^2$ is —$CF_2$—O— and $Z^3$ is —O—$CF_2$—.

The compounds of formula I are accessible by the usual methods known to the expert. Starting materials may be, e.g., compounds of the following types, which are either commercially available or accessible by published methods:

Preferably the liquid crystalline media according to the instant invention contain a component A comprising, preferably predominantly consisting of and most preferably entirely consisting of compounds of formula I.

Comprising in this application means in the context of compositions that the entity referred to, e.g. the medium or the component, contains the compound or compounds in question, preferably in a total concentration of 10% or more and most preferably of 20% or more.

Predominantly consisting, in this context, means that the entity referred to contains 80% or more, preferably 90% or more and most preferably 95% or more of the compound or compounds in question.

Entirely consisting, in this context, means that the entity referred to contains 98% or more, preferably 99% or more and most preferably 100.0% of the compound or compounds in question.

The concentration of the compounds according to the present application are contained in the media according to the present application preferably is in the range from 0.5% or more to 70% or less, more preferably in the range from 1% or more to 60% or less and most preferably in the range from 5% or more to 50% or less.

In a preferred embodiment the mesogenic modulation media according to the instant invention comprise
one compound or more compounds selected from the group of compounds of formulae M-I and M-II, preferably in a total concentration of 1% to 25% by weight, more preferably in a concentration of 1% to 20% by weight, and most preferably in a concentration of 1% to 10% by weight for each single compound present, and/or
one compound or more compounds selected from the group of compounds of formulae I and II, preferably in a concentration of 1% to 25% by weight, and/or
optionally, preferably obligatorily, one or more compounds selected from the group of compounds of formulae IV and V and/or
one or more chiral compounds with an absolute value of the HTP of ≥20 µm$^{-1}$, preferably in a concentration of 1% to 20% by weight, and
optionally, preferably obligatorily, a polymer precursor, comprising reactive compounds, preferably comprising reactive mesogens, which, upon polymerisation, are able to, and preferably do stabilize the phase range of the blue phase and/or decrease the temperature dependence of the electro-optical effect.

The inventive mixtures preferably comprise one or more compounds selected from the group of compounds of formulae I and II and optionally III, preferably in a total concentration in the range from 40% or more to 80% or less, preferably from 45% or more to 75% or less and most preferably from 50% or more to 70% or less.

In particular, the inventive mixtures preferably comprise one or more compounds of formula I in a total concentration in the range from 40% or more to 80% or less, preferably from 45% or more to 75% or less and most preferably from 50% or more to 70% or less.

In case the inventive mixtures comprise one or more compounds formula II, the total concentration of these compounds preferably is in the range from 1% or more to 15% or less, preferably from 2% or more to 10% or less and most preferably from 4% or more to 8% or less.

In case the inventive mixtures comprise one or more compounds formula III, the total concentration of these compounds preferably is in the range from 1% or more to 20% or less, preferably from 2% or more to 15% or less and most preferably from 3% or more to 10% or less.

In case the inventive mixtures comprise one or more compounds formula IV the total concentration of these compounds preferably is in the range from 1% or more to 15% or less, preferably from 2% or more to 10% or less and, most preferably, from 4% or more to 8% or less.

In case the inventive mixtures comprise one or more compounds formula V the total concentration of these compounds preferably is in the range from 5% or more to 45% or less, preferably from 15% or more to 40% or less and most preferably from 25% or more to 35% or less.

Suitable chiral compounds are those, which have an absolute value of the helical twisting power of 20 µm$^{-1}$ or more, preferably of 40 µm$^{-1}$ or more and most preferably of 60 µm$^{-1}$ or more. The HTP is measured in the liquid crystalline medium MLC-6260 at a temperature of 20° C.

The mesogenic media according to the present invention comprise preferably one or more chiral compounds, which have a mesogenic structure and exhibit preferably one or more meso-phases themselves, particularly at least one cholesteric phase. Preferred chiral compounds being comprised in the mesogenic media are, amongst others, well known chiral dopants like cholesteryl-nonanoate (CN), R/S-

811, R/S-1011, R/S-2011, R/S-3011, R/S-4011, R/S-5011, CB-15 (Merck KGaA, Darmstadt, Germany). Preferred are chiral dopants having one or more chiral moieties and one or more mesogenic groups or having one or more aromatic or alicyclic moieties forming, together with the chiral moiety, a mesogenic group. More preferred are chiral moieties and mesogenic chiral compounds disclosed in DE 34 25 503, DE 35 34 777, DE 35 34 778, DE 35 34 779, DE 35 34 780, DE 43 42 280, EP 01 038 941 and DE 195 41 820 that disclosure is incorporated within this application by way of reference. Particular preference is given to chiral binaphthyl derivatives as disclosed in EP 01 111 954.2, chiral binaphthol derivatives as disclosed in WO 02/34739, chiral TADDOL derivatives as disclosed in WO 02/06265 as well as chiral dopants having at least one fluorinated linker and one end chiral moiety or one central chiral moiety as disclosed in WO 02/06196 and WO 02/06195.

The mesogenic media of the present invention have a characteristic temperature, preferably a clearing point, in the range from about −30° C. to about 90° C., especially of 60° C. or more, preferably of 70° C. or more and most preferably of 80° C. or more.

The inventive mixtures preferably contain one ore more (two, three, four or more) chiral compounds in the range of 1-25 wt. %, preferably 2-20 wt. %, each. Especially preferred are mixtures containing 3-15 wt.-% total of one or more chiral compounds.

Preferred embodiments are indicated below:

The medium comprises one, two, three, four or more compounds of formula D, preferably one, two, three, four or more compounds each of formulae D-1 and/or D-2, and/or the medium comprises one, two, three, four or more compounds of formula I, preferably one, two, three, four or more compounds each of formulae I-1 and/or I-2 and/or I-4, in particular of formulae I-4a and/or I-4b and/or the medium comprises one, two or more compounds of formula II, preferably of formula II-3 and/or II-4 and/or II-7 and/or the medium comprises one or more compounds of formula III and/or the medium comprises one, two or more compounds of formula IV and/or the medium comprises one, two or more compounds of formula V and/or the medium comprises one, two, three or more chiral compounds, preferably having a helical twisting power of 20 µm$^{-1}$ or more, and/or the medium comprises one, two or more reactive compounds, preferably one two or more reactive mesogenic compounds, preferably of formulae P, preferably of one or more of its sub-formulae, and/or one or more reactive mesogenic compounds selected from the group of formulae M1 to M29, preferably of formulae M16-A and/or M17-A, more preferably of formula M17-A'.

The optimum mixing ratio of the compounds of the formulae D and I and II and III depends substantially on the desired properties, on the choice of the components of the formulae D, I and/or II and/or III, and on the choice of any other components that may be present. Suitable mixing ratios within the range given above can easily be determined from case to case.

The total amount of compounds of the formulae D and I and II and optionally III in the mixtures according to the invention is in many cases not crucial. The mixtures can therefore comprise one or more further components for the purposes of optimisation of various properties. However, the observed effect on the operating voltage and the operating temperature range is generally greater, the higher the total concentration of compounds of the formulae D and I and optionally III and/or III.

In case the medium comprises one compound of formula D, the concentration of that compound in the medium preferably is in the range from 1 to 25%, preferably from 2 to 20% and most preferably from 3 to 15%.

In case the medium comprises two or more compounds of formula D, the total concentration of these compounds in the medium preferably is in the range from 3 to 55%, preferably from 10 to 50% and most preferably from 12 to 35%.

The concentration of the compounds of formula I-1 (in the medium preferably is in the range from 10 to 40%, more preferably from 15 to 35% and most preferably from 20 to 30%.

The concentration of the compounds of formula I-2 in the medium preferably is in the range from 10 to 60%, more preferably from 15 to 55% and most preferably from 20 to 50%.

The concentration of the compounds of formula I-3 in the medium preferably is in the range from 10 to 60%, more preferably from 15 to 50% and most preferably from 20 to 45%.

The concentration of the compounds of formula I-4 in the medium preferably is in the range from 10 to 50%, more preferably from 20 to 45% and most preferably from 25 to 40%.

The concentration of all compounds present in the medium is 100%.

It has been found that even a relatively small proportion of compounds of the formula D mixed with other known liquid-crystal materials, but in particular with one or more compounds of the formula I and optionally of formulae II and III, leads to a lower operating voltage and a broader operating temperature range. Preference is given, in particular, to mixtures which, besides one or more compounds of the formula D, comprise one or more compounds of the formula I, in particular compounds of the formula I-1 and/or I-2 and/or I-4.

The compounds of the formulae D and I to V are colourless, stable and readily miscible with one another and with other liquid-crystalline materials.

In a particularly preferred embodiment, the media according to the invention comprise one or more compounds each of the formulae D-1 and/or D-2 and formula I and/or II and optionally III. A favourable synergistic effect with the compounds of the formula D and I results in particularly advantageous properties. In particular, mixtures comprising compounds of formula D and formula I and optionally of formula II and/or of formula III are distinguished by their low operating voltages.

The individual compounds of the formulae D, I, II to III and/or IV and/or V, which can be used in the media according to the invention, are either known or can be prepared analogously to the known compounds.

The construction of the MLC display according to the invention from polarisers, electrode base plates and surface-treated electrodes corresponds to the conventional construction for displays of this type. The term conventional construction is broadly drawn here and also covers all derivatives and modifications of the MLC display, in particular including matrix display elements based on poly-Si TFT or MIM, however, particularly preferred are displays, which have electrodes on just one of the substrates, i.e. so called inter-digital electrodes, as those used in IPS displays, preferably in one of the established structures.

A significant difference between the displays according to the invention and the conventional displays based on the twisted nematic cell consists, however, in the choice of the liquid-crystal parameters of the liquid-crystal layer.

The media according to the invention are prepared in a manner conventional per se. In general, the components are dissolved in one another, advantageously at elevated temperature. By means of suitable additives, the liquid-crystalline phases in accordance with the invention can be modified in such a way that they can be used in all types of liquid crystal display elements that have been disclosed hitherto. Additives of this type are known to the person skilled in the art and are described in detail in the literature (H. Kelker and R. Hatz, Handbook of Liquid Crystals, Verlag Chemie, Weinheim, 1980). For example, pleochroic dyes can be added for the preparation of coloured guest-host systems or substances can be added in order to modify the dielectric anisotropy, the viscosity and/or the alignment of the nematic phases. Furthermore, stabilisers and antioxidants can be added.

The mixtures according to the invention are suitable for TN, STN, ECB and IPS applications and isotropic switching mode (ISM) applications. Hence, there use in an electro-optical device and an electro-optical device containing liquid crystal media comprising at least one compound according to the invention are subject matters of the present invention.

The inventive mixtures are highly suitable for devices, which operate in an optically isotropic state. The mixtures of the invention are surprisingly found to be highly suitable for the respective use.

Electro-optical devices that are operated or operable in an optically isotropic state recently have become of interest with respect to video, TV, and multi-media applications. This is, because conventional liquid crystal displays utilizing electro-optical effects based on the physical properties of liquid crystals exhibit a rather high switching time, which is undesired for said applications. Furthermore most of the conventional displays show a significant viewing angle dependence of contrast that in turn makes necessary measures to compensate this undesired property.

With regard to devices utilizing electro-optical effects in an isotropic state the German Patent Application DE 102 17 273 A1 for example discloses light-controlling (light modulation) elements in which the mesogenic controlling medium for modulation is in the isotropic phase at the operating temperature. These light controlling elements have a very short switching time and a good viewing angle dependence of contrast. However, the driving or operating voltages of said elements are very often unsuitably high for some applications.

German Patent Application DE 102 41 301 yet unpublished describes specific structures of electrodes allowing a significant reduction of the driving voltages. However, these electrodes make the process of manufacturing the light controlling elements more complicated.

Furthermore, the light controlling elements, for example, disclosed in both DE 102 17 273 A1 and DE 102 41 301 show significant temperature dependence. The electro-optical effect that can be induced by the electrical field in the controlling medium being in an optical isotropic state is most pronounced at temperatures close to the clearing point of the controlling medium. In this range the light controlling elements have the lowest values of their characteristic voltages and, thus, require the lowest operating voltages. As temperature increases, the characteristic voltages and hence the operating voltages increase remarkably. Typical values of the temperature dependence are in the range from about a few volts per centigrade up to about ten or more volts per centigrade. While DE 102 41 301 describes various structures of electrodes for devices operable or operated in the isotropic state, DE 102 17 273 A1 discloses isotropic media of varying composition that are useful in light controlling elements operable or operated in the isotropic state. The relative temperature dependence of the threshold voltage in these light controlling elements is at a temperature of 1 centigrade above the clearing point in the range of about 50%/centigrade. That temperature dependence decreases with increasing temperature so that it is at a temperature of 5 centigrade above the clearing point of about 10%/centigrade. However, for many practical applications of displays utilizing said light controlling elements the temperature dependence of the electro-optical effect is too high. To the contrary, for practical uses it is desired that the operating voltages are independent from the operating temperature over a temperature range of at least some centigrade, preferably of about 5 centigrade or more, even more preferably of about 10 centigrade or more and especially of about 20 centigrade or more.

Now it has been found that the use of the inventive mixtures are highly suitable as controlling media in the light controlling elements as described above and in DE 102 17 273 A1, DE 102 41 301 and DE 102 536 06 and broaden the temperature range in which the operating voltages of said electro-optical operates. In this case the optical isotropic state or the blue phase is almost completely or completely independent from the operating temperature.

This effect is even more distinct if the mesogenic controlling media exhibit at least one so-called "blue phase" as described in WO 2004/046 805. Liquid crystals having an extremely high chiral twist may have one or more optically isotropic phases. If they have a respective cholesteric pitch, these phases might appear bluish in a cell having a sufficiently large cell gap. Those phases are therefore also called "blue phases" (Gray and Goodby, "Smectic Liquid Crystals, Textures and Structures", Leonhard Hill, USA, Canada (1984)). Effects of electrical fields on liquid crystals existing in a blue phase are described for instance in H. S. Kitzerow, "The Effect of Electric Fields on Blue Phases", Mol. Cryst. Liq. Cryst. (1991), Vol. 202, p. 51-83, as well as the three types of blue phases identified so far, namely BP I, BP II, and BP III, that may be observed in field-free liquid crystals. It is noteworthy, that if the liquid crystal exhibiting a blue phase or blue phases is subjected to an electrical field, further blue phases or other phases different from the blue phases I, II and III might appear.

The inventive mixtures can be used in an electro-optical light-controlling element which comprises
 one or more, especially two substrates;
 an assembly of electrodes;
 one or more elements for polarizing the light; and
 said controlling medium;
 whereby said light-controlling element is operated (or operable) at a temperature at which the controlling medium is in an optically isotropic phase when it is in a non-driven state.

The controlling medium of the present invention has a characteristic temperature, preferably a clearing point, in the range from about −30° C. to about 90° C., especially up to about 70° C. to 80° C.

The operating temperature of the light controlling elements is preferably above the characteristic temperature of the controlling medium said temperature being usually the transition temperature of the controlling medium to the blue phase; generally the operating temperature is in the range of about 0.1° to about 50°, preferably in the range of about 0.1° to about 10° above said characteristic temperature. It is highly preferred that the operating temperature is in the range from the transition temperature of the controlling medium to the blue phase up to the transition temperature of the controlling medium to the isotropic phase, which is the clearing point. The light controlling elements, however, may also be operated at temperatures at which the controlling medium is in the isotropic phase.

For the purposes of the present invention the term "characteristic temperature" is defined as follows:

If the characteristic voltage as a function of temperature has a minimum, the temperature at this minimum is denoted as characteristic temperature.

If the characteristic voltage as a function of temperature has no minimum and if the controlling medium has one or more blue phases, the transition temperature to the blue phase is denoted as characteristic temperature; in case there are more than one blue phase, the lowest transition temperature to a blue phase is denoted as characteristic temperature.

If the characteristic voltage as a function of temperature has no minimum, and if the controlling medium has no blue phase, the transition temperature to the isotropic phase is denoted as characteristic temperature.

In the context of the present invention the term "alkyl" means, as long as it is not defined in a different manner elsewhere in this description or in the claims, straight-chain and branched hydrocarbon (aliphatic) radicals with 1 to 15 carbon atoms. The hydrocarbon radicals may be unsubstituted or substituted with one or more substituents being independently selected from the group consisting of F, Cl, Br, I or CN.

The dielectrics may also comprise further additives known to the person skilled in the art and described in the literature. For example, 0 to 5% of pleochroic dyes, antioxidants or stabilizers can be added.

C denotes a crystalline phase, S a smectic phase, $S_C$ a smectic C phase, N a nematic phase, I the isotropic phase and BP the blue phase. $V_X$ denotes the voltage for X % transmission. Thus e.g. $V_{10}$ denotes the voltage for 10% transmission and $V_{100}$ denotes the voltage for 100% transmission (viewing angle perpendicular to the plate surface). $t_{on}$ (respectively $\tau_{on}$) denotes the switch-on time and $t_{off}$ (respectively $\tau_{off}$) the switch-off time at an operating voltage corresponding the value of $V_{100}$, respectively of $V_{max}$. $t_{on}$ is the time for the change of the relative transmission from 10% to 90% and $t_{off}$ is the time for the change of the relative transmission from 90% to 10%. The response times are determined with the measurement instrument DMS from Autronic Melchers, Germany, just as the electro-optical characteristics. $\Delta n$ denotes the optical anisotropy. $\Delta \epsilon$ denotes the dielectric anisotropy ($\Delta \epsilon = \epsilon_\parallel - \epsilon_\perp$, where $\epsilon_\parallel$ denotes the dielectric constant parallel to the longitudinal molecular axes and $\epsilon_\parallel$ denotes the dielectric constant perpendicular thereto). The electro-optical data are measured in a TN cell at the $1^{st}$ minimum of transmission (i.e. at a (d·$\Delta n$) value of 0.5 µm) at 20° C., unless expressly stated otherwise. The optical data are measured at 20° C., unless expressly stated otherwise.

Optionally, the light modulation media according to the present invention can comprise further liquid crystal compounds in order to adjust the physical properties. Such compounds are known to the expert. Their concentration in the media according to the instant invention is preferably 0% to 30%, more preferably 0% to 20% and most preferably 5% to 15%.

Preferably, inventive media have a range of the blue phase or, in case of the occurrence of more than one blue phase, a combined range of the blue phases, with a width of 20° or more, preferably of 40° or more, more preferably of 50° or more and most preferably of 60° or more.

In a preferred embodiment this phase range at least from 10° C. to 30° C., most preferably at least from 10° C. to 40° C. and most preferably at least from 0° C. to 50° C., wherein at least means, that preferably the phase extends to temperatures below the lower limit and at the same time, that it extends to temperatures above the upper limit.

In another preferred embodiment this phase range at least from 20° C. to 40° C., most preferably at least from 30° C. to 80° C. and most preferably at least from 30° C. to 90° C. This embodiment is particularly suited for displays with a strong backlight, dissipating energy and thus heating the display.

Preferably the inventive media have a dielectric anisotropy of 150 or more, more preferably of 200 or more, even more preferably of 250 or more and most preferably of 300 or more. In particular, the value of dielectric anisotropy of the inventive media is preferably 600 or less, more preferably 550 or less.

In the present application the term dielectrically positive compounds describes compounds with $\Delta\epsilon > 1.5$, dielectrically neutral compounds are compounds with $-1.5 \leq \Delta\epsilon \leq 1.5$ and dielectrically negative compounds are compounds with $\Delta\epsilon < -1.5$. The same holds for components. $\Delta\epsilon$ is determined at 1 kHz and 20° C. The dielectric anisotropies of the compounds is determined from the results of a solution of 10% of the individual compounds in a nematic host mixture. The capacities of these test mixtures are determined both in a cell with homeotropic and with homogeneous alignment. The cell gap of both types of cells is approximately 20 µm. The voltage applied is a rectangular wave with a frequency of 1 kHz and a root mean square value typically of 0.5 V to 1.0 V, however, it is always selected to be below the capacitive threshold of the respective test mixture.

For dielectrically positive compounds the mixture ZLI-4792 and for dielectrically neutral, as well as for dielectrically negative compounds, the mixture ZLI-3086, both of Merck KGaA, Germany are used as host mixture, respectively. The dielectric permittivities of the compounds are determined from the change of the respective values of the host mixture upon addition of the compounds of interest and are extrapolated to a concentration of the compounds of interest of 100%.

Components having a nematic phase at the measurement temperature of 20° C. are measured as such, all others are treated like compounds.

The term threshold voltage refers in the instant application to the optical threshold and is given for 10% relative contrast ($V_{10}$) and the term saturation voltage refers to the optical saturation and is given for 90% relative contrast ($V_{90}$) both, if not explicitly stated otherwise. The capacitive threshold voltage ($V_0$, also called Freedericksz-threshold $V_{Fr}$) is only used if explicitly mentioned.

The ranges of parameters given in this application are all including the limiting values, unless explicitly stated otherwise.

Throughout this application, unless explicitly stated otherwise, all concentrations are given in mass percent and relate to the respective complete mixture, all temperatures are given in degrees centigrade (Celsius) and all differences of temperatures in degrees centigrade. All physical properties have been and are determined according to "Merck Liquid Crystals, Physical Properties of Liquid Crystals", Status November 1997, Merck KGaA, Germany and are given for a temperature of 20° C., unless explicitly stated otherwise. The optical anisotropy ($\Delta n$) is determined at a wavelength of 589.3 nm. The dielectric anisotropy ($\Delta \epsilon$) is determined at a frequency of 1 kHz. The threshold voltages, as well as all other electro-optical properties have been determined with test cells prepared at Merck KGaA, Germany. The test cells for the determination of $\Delta \epsilon$ had a cell gap of 22 µm. The electrode was a circular ITO electrode with an area of 1.13 cm$^2$ and a guard ring. The orientation layers were lecithin for homeotropic orientation ($\epsilon_\parallel$) and polyimide AL-1054 from Japan Synthetic Rubber for homogenous orientation ($\epsilon_\perp$). The capacities were determined with a frequency response analyser Solatron 1260 using a sine wave with a voltage of 0.3 or 0.1 $V_{rms}$. The light used in the electro-optical measurements was white light. The set up used was a commercially available equipment of Otsuka, Japan. The characteristic voltages have been determined under perpendicular observation. The threshold voltage ($V_{10}$), mid-grey voltage ($V_{50}$) and saturation voltage ($V_{90}$) have been determined for 10%, 50% and 90% relative contrast, respectively.

The mesogenic modulation material has been filled into an electro optical test cell prepared at the respective facility of Merck KGaA. The test cells had inter-digital electrodes on one substrate side. The electrode width was 10 µm, the distance between adjacent electrodes was 10 µm and the cell gap was also 10 µm. This test cell has been evaluated electro-optically between crossed polarisers.

At low temperatures, the filled cells showed the typical texture of a chiral nematic mixture, with an optical transmission between crossed polarisers without applied voltage. Upon heating, at a first temperature ($T_1$) the mixtures turned optically isotropic, being dark between the crossed polarisers. This indicated the transition from the chiral nematic phase to the blue phase at that temperature. Up to a second temperature ($T_2$) the cell showed an electro-optical effect under applied voltage, typically of some tens of volts, a certain voltage in that range leading to a maximum of the optical transmission. Typically at a higher temperature the voltage needed for a visible electro-optical effect increased strongly, indicating the transition from the blue phase to the isotropic phase at this second temperature ($T_2$).

The temperature range ($\Delta T(BP)$), where the mixture can be used electro-optically in the blue phase most beneficially has been identified as ranging from $T_1$ to $T_2$. This temperature range ($\Delta T(BP)$) is the temperature range given in the examples of this application. The electro-optical displays can also be operated at temperatures beyond this range, i.e. at temperatures above $T_2$, albeit only at significantly increased operation voltages.

The liquid crystal media according to the present invention can contain further additives and chiral dopants in usual concentrations. The total concentration of these further constituents is in the range of 0% to 10%, preferably 0.1% to 6%, based in the total mixture. The concentrations of the individual compounds used each are preferably in the range of 0.1 to 3%. The concentration of these and of similar additives is not taken into consideration for the values and ranges of the concentrations of the liquid crystal components and compounds of the liquid crystal media in this application.

The inventive liquid crystal media according to the present invention consist of several compounds, preferably of 3 to 30, more preferably of 5 to 20 and most preferably of 6 to 14 compounds. These compounds are mixed in conventional way. As a rule, the required amount of the compound used in the smaller amount is dissolved in the compound used in the greater amount. In case the temperature is above the clearing point of the compound used in the higher concentration, it is particularly easy to observe completion of the process of dissolution. It is, however, also possible to prepare the media by other conventional ways, e.g. using so called pre-mixtures, which can be e. g. homologous or eutectic mixtures of compounds or using so called multi-bottle-systems, the constituents of which are ready to use mixtures themselves.

By addition of suitable additives, the liquid crystal media according to the instant invention can be modified in such a way, that they are usable in all known types of liquid crystal displays, either using the liquid crystal media as such, like TN-, TN-AMD, ECB-, VAN-AMD and in particular in composite systems, like PDLD-, NCAP- and PN-LCDs and especially in HPDLCs.

The melting point: T(K,N), T(K,S) or T(K,I), respectively, the transition temperature from one smectic phase ($S_x$) to another smectic phase ($S_Y$): T($S_x$,$S_Y$), the transition temperature from the smectic (S) to the nematic (N) phase: T(S,N), the clearing point: T (N,I), and the glass transition temperature: $T_g$ of the liquid crystals, as applicable, as well as any other temperature throughout this application, are given in degrees centigrade (i.e. Celsius).

The compounds of the formula P and the sub-formulae thereof can be prepared analogously to the process known to the person skilled in the art and described in standard works of organic chemistry, such as, for example, in Houben-Weyl, Methoden der organischen Chemie [Methods of Organic Chemistry], Thieme-Verlag, Stuttgart.

Particularly suitable and preferred processes for the preparation of compounds of the formula P and the sub-formulae thereof are shown by way of example in the following schemes and preferably comprise one or more of the steps described below.

The person skilled in the art will be able to modify the synthesis in a suitable manner and thus obtain further compounds according to the invention. The particularly preferred compounds containing an alkoxy spacer or acrylates bonded directly to the ring are obtained, for example, by reaction of phenol derivatives, such as, for example, compound 12, with the dithianylium salts 13. The compounds 14 formed initially here are converted into the compounds 15. The hydroxyl group can subsequently be functionalised in a suitable manner, for example by esterification using methacrylic acid (cf. Scheme 1).

The compounds of formula P wherein the rings are linked by an —$CF_2$—O— group and the reactive groups are attached to the rings via an alkylene spacer group, which are used according to the present invention in a particularly preferred embodiment, can be prepared according to the following scheme.

Scheme 1: Exemplary synthesis of compounds of formula P with spacers linked by C—C-single bonds

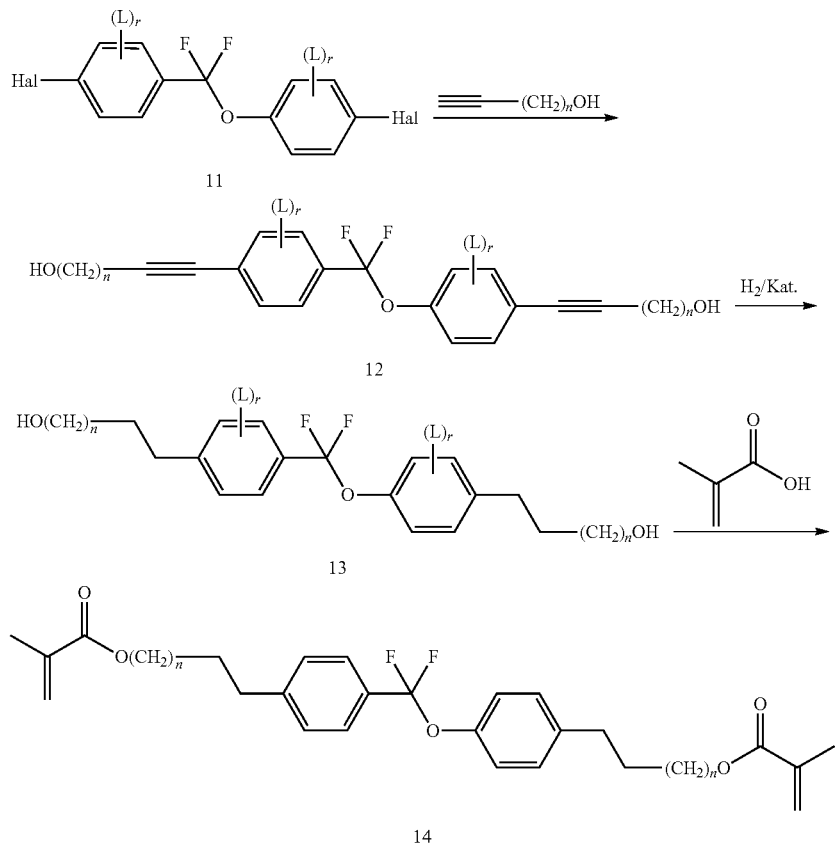

In the present invention and especially in the following examples, the structures of the mesogenic compounds are indicated by means of abbreviations, also called acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1E-alkenyl, each having n, m and l C atoms respectively. Table A lists the codes used for the ring elements of the core structures of the compounds, while Table B shows the linking groups. Table C gives the meanings of the codes for the left-hand or right-hand end groups. The acronyms are composed of the codes for the ring elements with optional linking groups, followed by a first hyphen and the codes for the left-hand end group, and a second hyphen and the codes for the right-hand end group. Table D shows illustrative structures of compounds together with their respective abbreviations.

TABLE A

| Ring elements | |
|---|---|
| C | ![cyclohexane] |
| P | ![phenylene] |

TABLE A-continued

| Ring elements | |
|---|---|
| D | ![dioxane] |
| DI | ![dioxane isomer] |
| A | ![tetrahydropyran] |
| AI | ![tetrahydropyran isomer] |
| G | ![fluorophenyl] |

TABLE A-continued
| | Ring elements | |
|---|---|---|
| Gl | 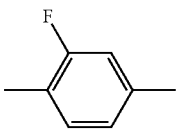 | |
| U | 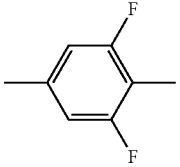 | |
| Ul | 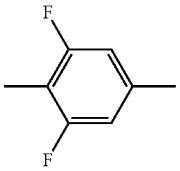 | |
| Y | 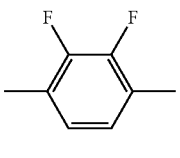 | |
| M | 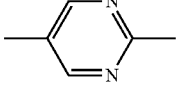 | |
| Ml | 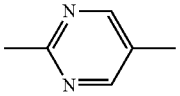 | |
| N | 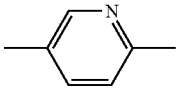 | |
| Nl | 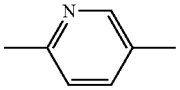 | |
| Np | 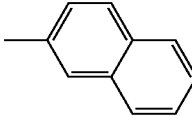 | |
| dH | 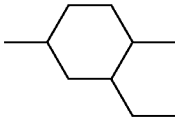 | |
| N3f | 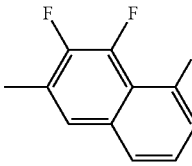 | |
| N3fl | 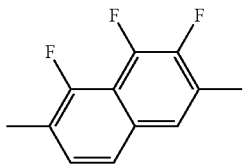 | |
| tH | 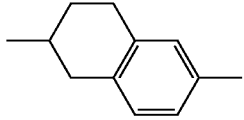 | |
| tHl | 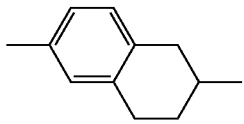 | |
| tH2f | 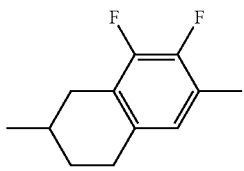 | |
| tH2fl | 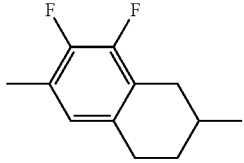 | |
| K |  | |
| Kl | 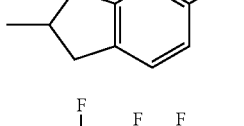 | |
| L | 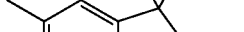 | |
| Ll | 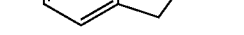 | |
| F |  | |
| Fl |  | |

TABLE B

| | Linking groups | | |
|---|---|---|---|
| E | —CH$_2$CH$_2$— | Z | —CO—O— |
| V | —CH=CH— | ZI | —O—CO— |
| X | —CF=CH— | O | —CH$_2$—O— |
| XI | —CH=CF— | OI | —O—CH$_2$— |

TABLE B-continued

| | Linking groups | | |
|---|---|---|---|
| B | —CF=CF— | Q | —CF$_2$—O— |
| T | —C≡C— | QI | —O—CF$_2$— |
| W | —CF$_2$CF$_2$— | T | —C≡C— |

TABLE C

| End groups | | | |
|---|---|---|---|
| Left-hand side | | Right-hand side | |
| Used alone | | | |
| -n- | C$_n$H$_{2n+1}$— | -n | —C$_n$H$_{2n+1}$ |
| -nO- | C$_n$H$_{2n+1}$—O— | -nO | —O—C$_n$H$_{2n+1}$ |
| -V- | CH$_2$=CH— | -V | —CH=CH$_2$ |
| -nV- | C$_n$H$_{2n+1}$—CH=CH— | -nV | —C$_n$H$_{2n}$—CH=CH$_2$ |
| -Vn- | CH$_2$=CH—C$_n$H$_{2n+1}$— | -Vn | —CH=CH—C$_n$H$_{2n+1}$ |
| -nVm- | C$_n$H$_{2n+1}$—CH=CH—C$_m$H$_{2m}$— | -nVm | —C$_n$H$_{2n}$—CH=CH—C$_m$H$_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | CFH$_2$— | -M | —CFH$_2$ |
| -D- | CF$_2$H— | -D | —CF$_2$H |
| -T- | CF$_3$— | -T | —CF$_3$ |
| -MO- | CFH$_2$O— | -OM | —OCFH$_2$ |
| -DO- | CF$_2$HO— | -OD | —OCF$_2$H |
| -TO- | CF$_3$O— | -OT | —OCF$_3$ |
| -OXF- | CF$_2$=CH—O— | -OXF | —O—CH=CF$_2$ |
| -A- | H—C≡C— | -A | —C≡C—H |
| -nA- | C$_n$H$_{2n+1}$—C≡C— | -An | —C≡C—C$_n$H$_{2n+1}$ |
| -NA- | N≡C—C≡C— | -AN | —C≡C—C≡N |
| Used together with one another and/or with others | | | |
| -...A...- | —C≡C— | -...A... | —C≡C— |
| -...V...- | CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m each denote integers, and the three dots " . . . " are placeholders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures

MGQU-n-F

MGQU-n-T

TABLE D-continued
Illustrative structures
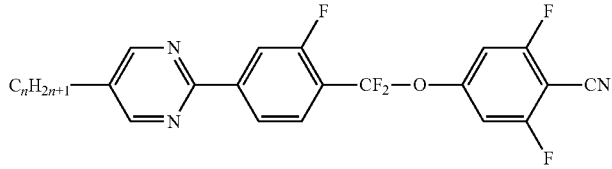
MGQU-n-N
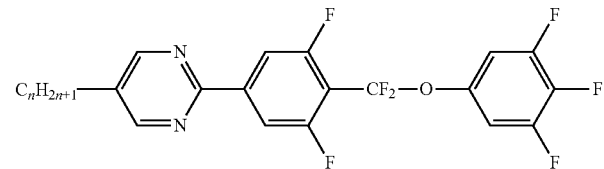
MUQU-n-F
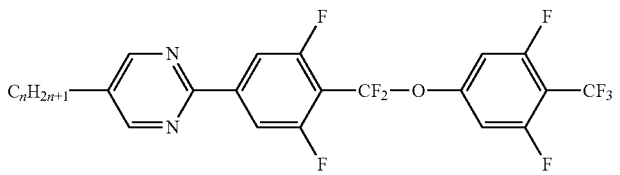
MUQU-n-T
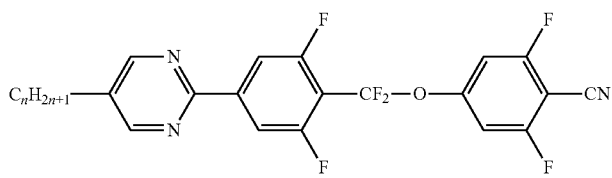
MUQU-n-N
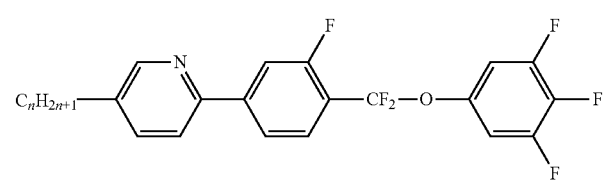
NGQU-n-F
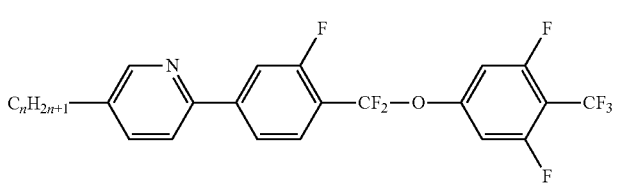
NGQU-n-T
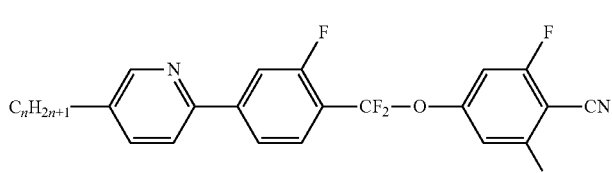
NGQU-n-N TABLE D-continued
Illustrative structures
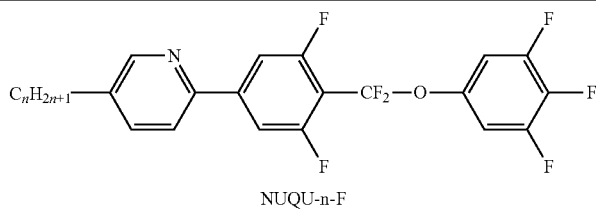
NUQU-n-F
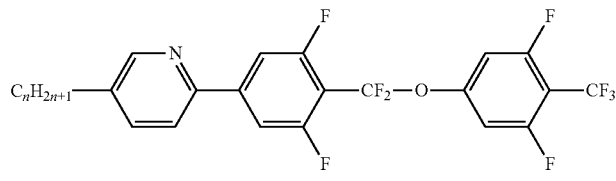
NUQU-n-T
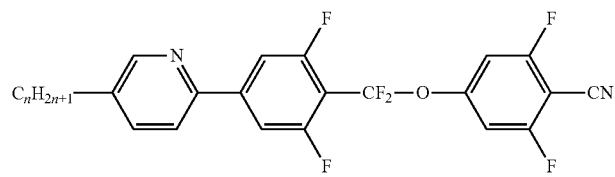
NUQU-n-N
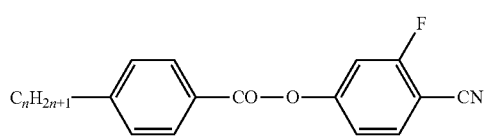
PZG-n-N
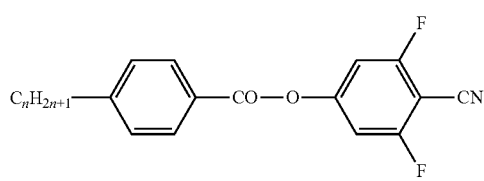
PZU-n-N
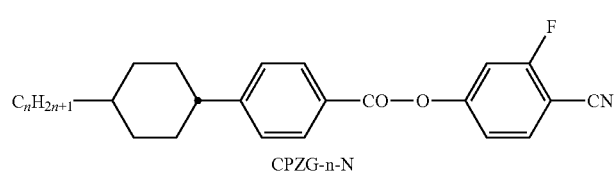
CPZG-n-N
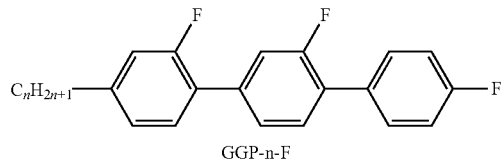
GGP-n-F
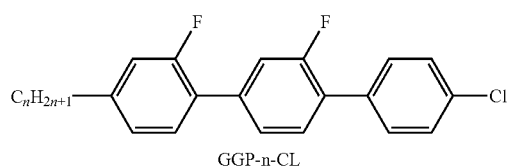
GGP-n-CL TABLE D-continued
Illustrative structures
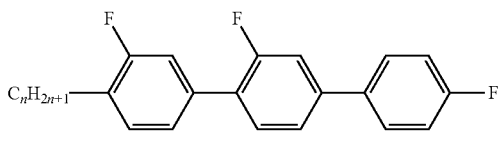
PGIGI-n-F
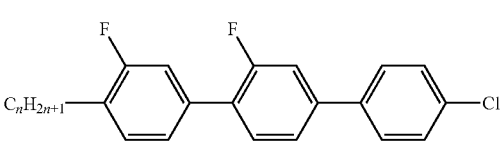
PGIGI-n-CL
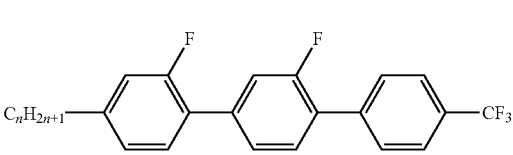
GGP-n-T
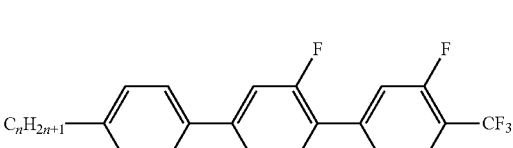
PGU-n-T
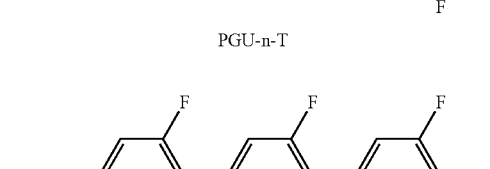
GGU-n-T
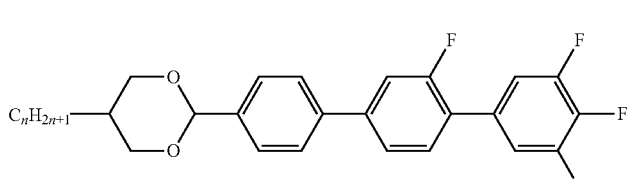
DPGU-n-F
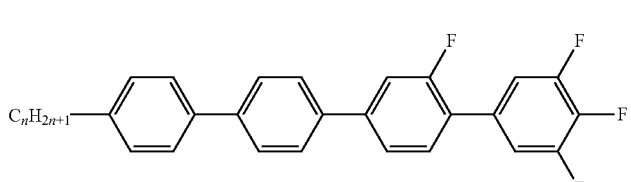
PPGU-n-F TABLE D-continued
Illustrative structures
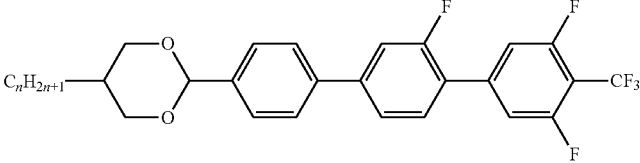
DPGU-n-T
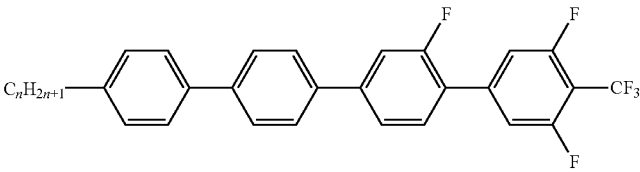
PPGU-n-T
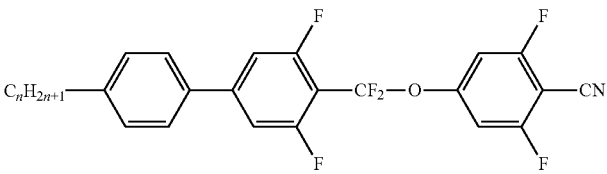
PUQU-n-N
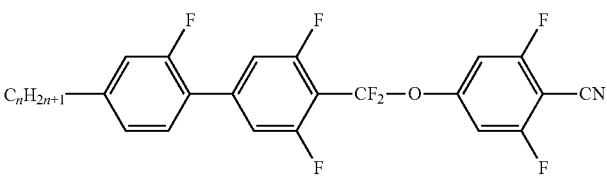
GUQU-n-N
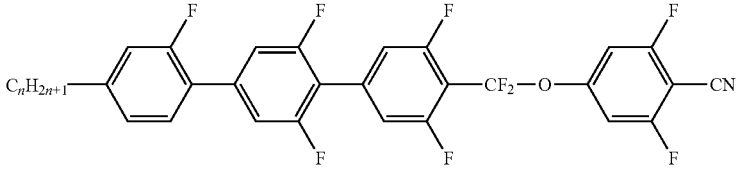
GUUQU-n-N
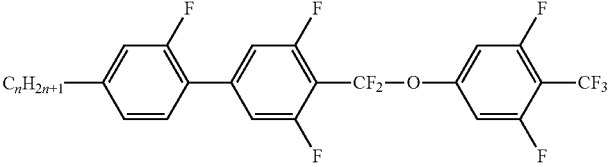
GUQU-n-F
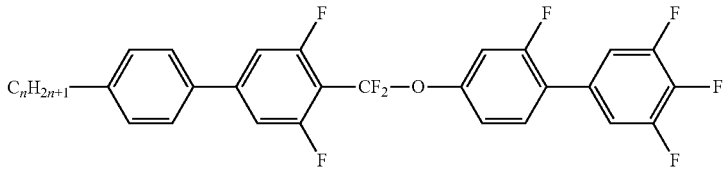
PUQGU-n-F TABLE D-continued Illustrative structures GUQGU-n-F PUQGU-n-T GUQGU-n-T DGUQU-n-F DUUQU-n-F DGUQU-n-T DUUQU-n-T

TABLE D-continued

Illustrative structures

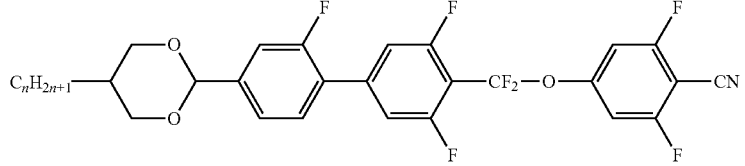

DGUQU-n-N

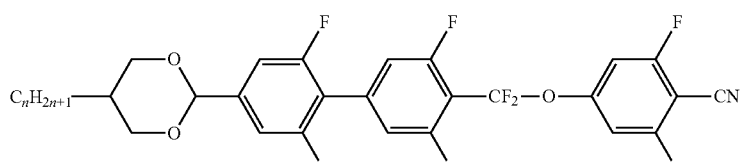

DUUQU-n-N

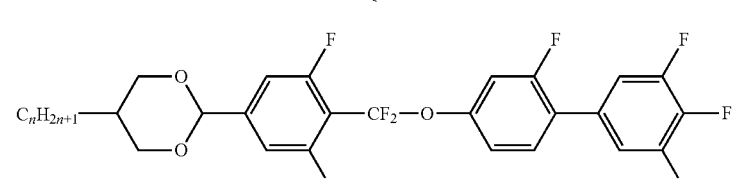

DUQGU-n-F

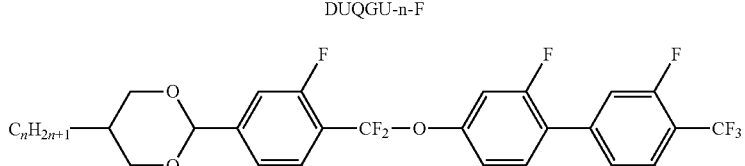

DUQGU-n-T

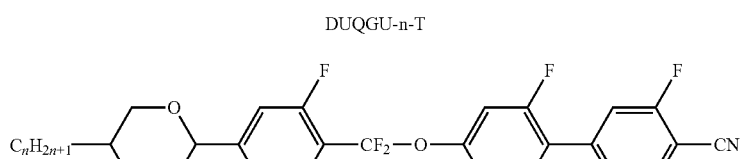

DUQGU-n-N in which n (m and l) preferably, independently of one another, denote(s) an integer from 1 to 7, preferably from 2 to 6.

The following table, Table E, shows illustrative compounds which can be used as stabiliser in the mesogenic media according to the present invention.

TABLE E

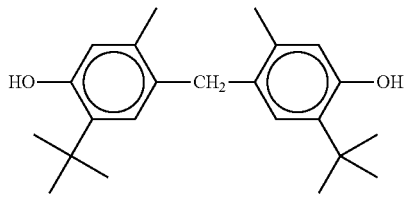

TABLE E-continued

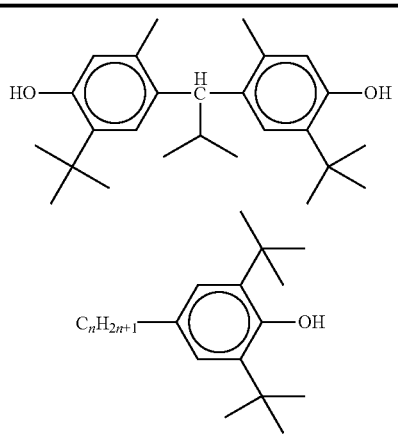

TABLE E-continued
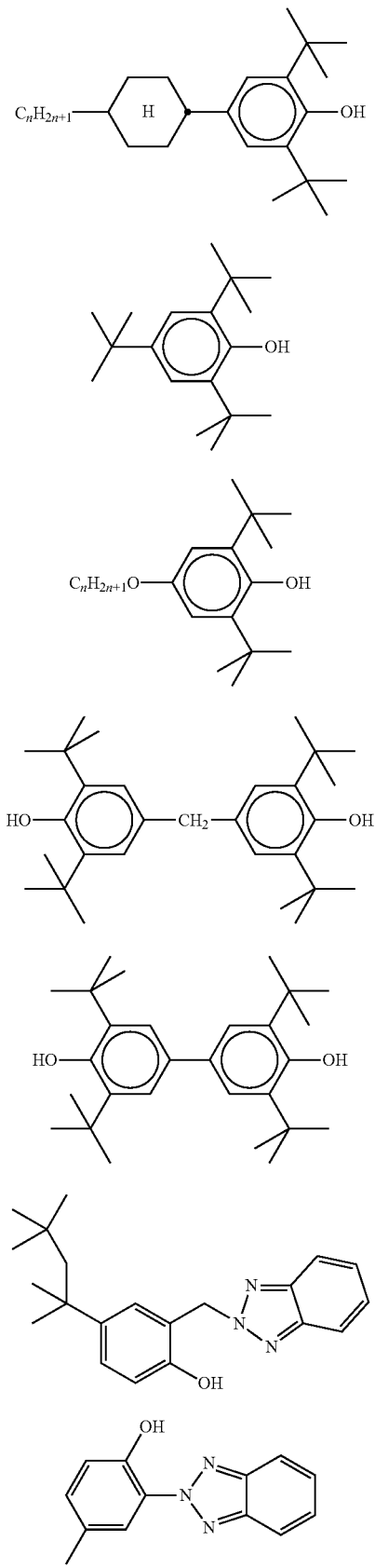
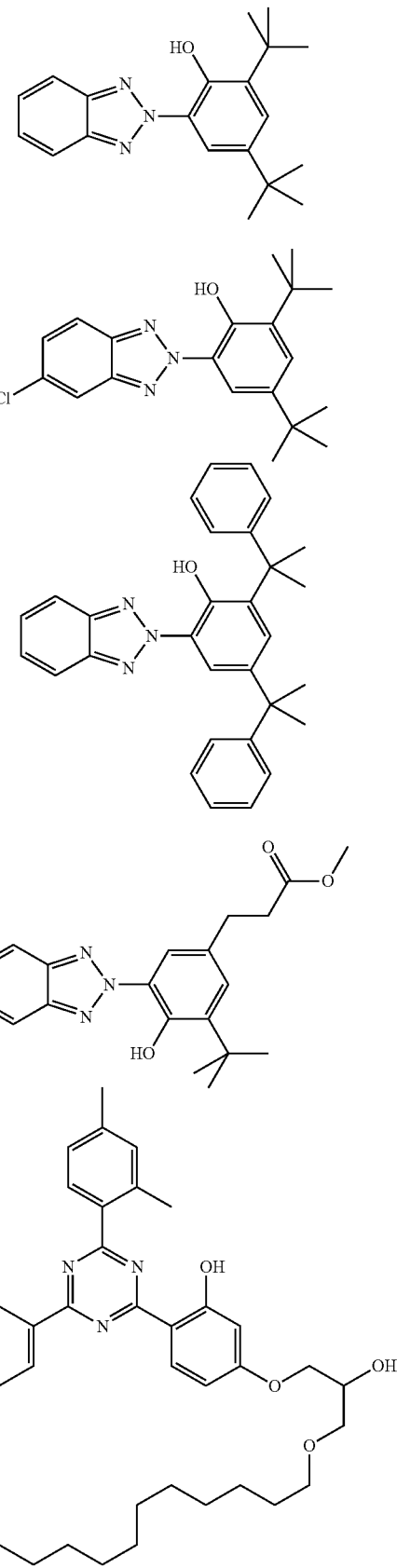

TABLE E-continued
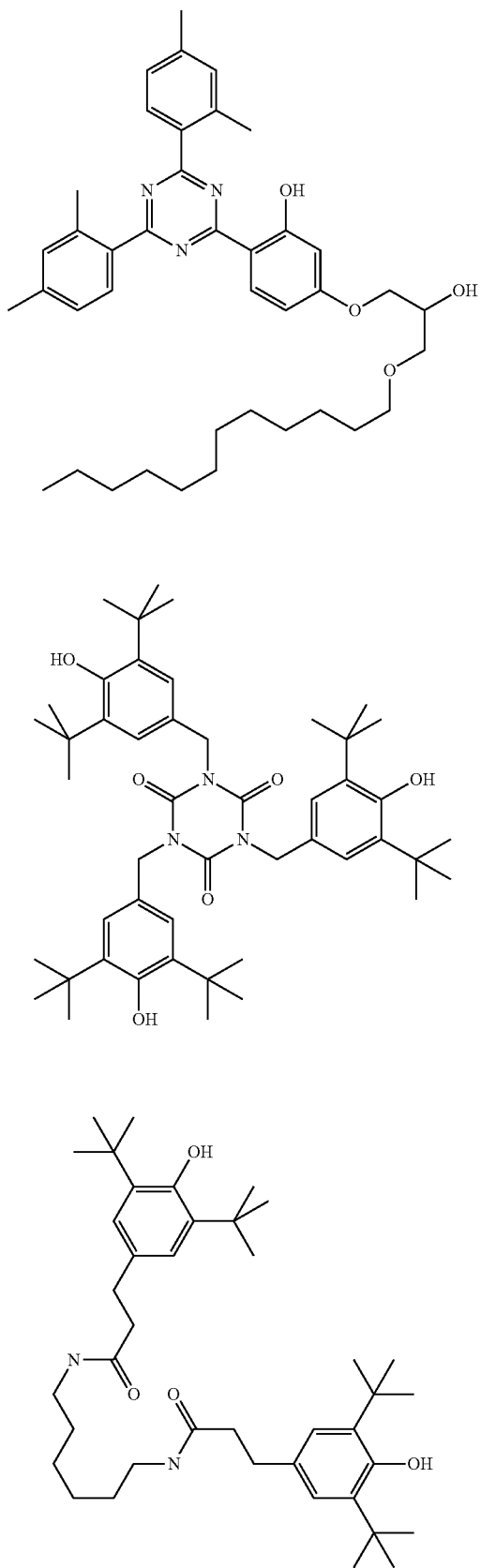
TABLE E-continued
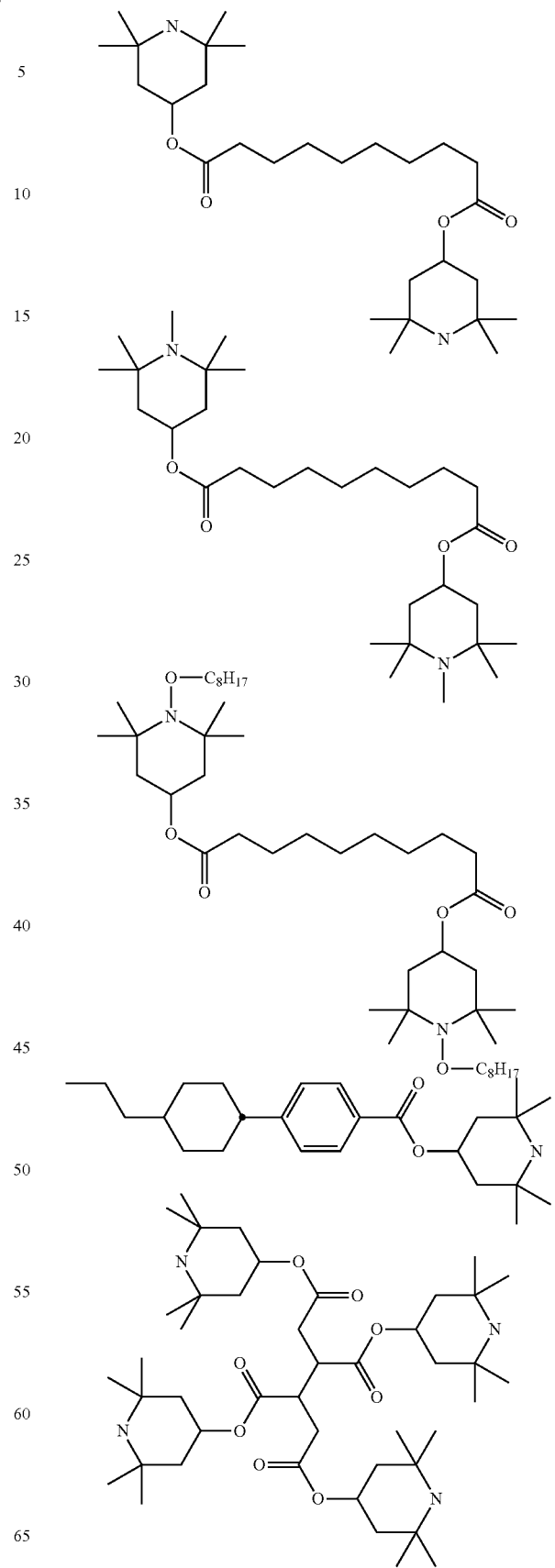

TABLE E-continued

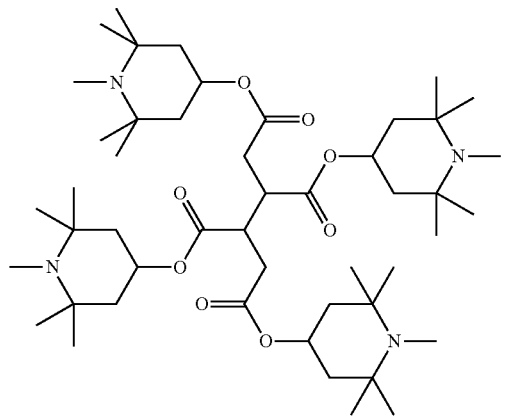

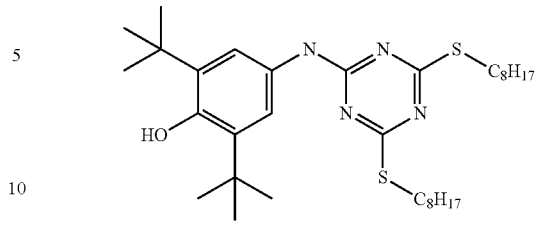

In a preferred embodiment of the present invention, the mesogenic media comprise one or more compounds selected from the group of the compounds from Table E.

The following table, Table F, shows illustrative compounds which can preferably be used as chiral dopants in the mesogenic media according to the present invention.

TABLE F

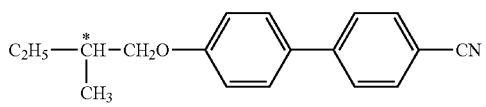
C15

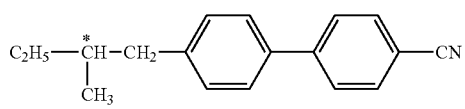
CB 15

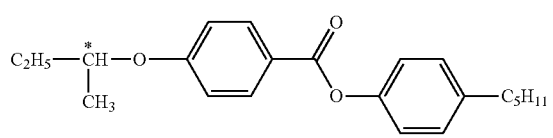
CM 21

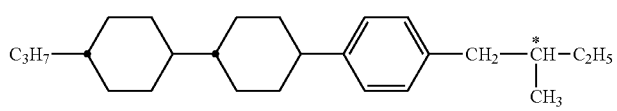
CM 44

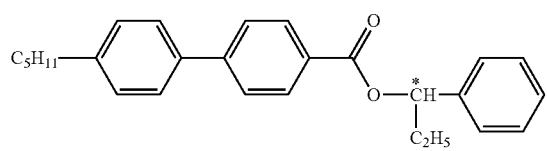
CM 45

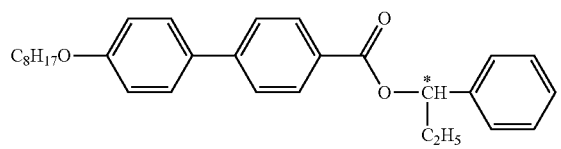
CM 47

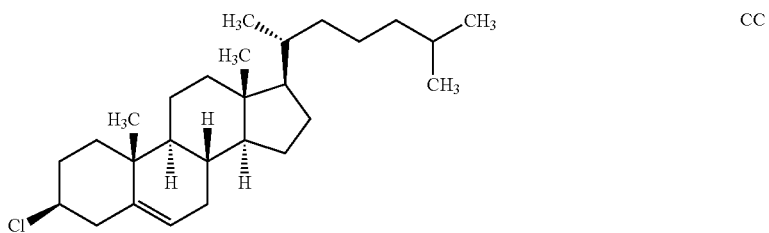
CC

TABLE F-continued

| Structure | Label |
|---|---|
| (cholesterol octanoate structure) | CN |
| (chiral biphenyl diester) | R/S-811 |
| (chiral dicyclohexyl phenyl ester) | R/S-1011 |
| (chiral difluorophenyl compound) | R/S-2011 |
| (chiral alkynyl ether compound) | R/S-3011 |
| (chiral adamantyl compound) | R/S-4011 |
| (binaphthyl dioxepine compound) | R/S-5011 |

In a preferred embodiment of the present invention, the mesogenic media comprise one or more compounds selected from the group of the compounds from Table F.

The mesogenic media according to the present application preferably comprise two or more, preferably four or more, compounds selected from the group consisting of the compounds from the above tables.

The liquid-crystal media according to the present invention preferably comprise seven or more, preferably eight or more, compounds, preferably compounds having three or more, preferably four or more, different formulae, selected from the group of the compounds from Table D.

EXAMPLES

The examples below illustrate the present invention without limiting it in any way.

However, the physical properties show the person skilled in the art what properties can be achieved and in what ranges they can be modified. In particular, the combination of the various properties which can preferably be achieved is thus well defined for the person skilled in the art.

Liquid-crystal mixtures having the composition and properties as indicated in the following tables are prepared and investigated.

The so-called "HTP" denotes the helical twisting power of an optically active or chiral substance in an LC medium (in μm$^{-1}$). Unless indicated otherwise, the HTP is measured in the commercially available nematic LC host mixture MLD-6260 (Merck KGaA) at a temperature of 20° C.

Synthesis Example 1

6-(4-{[4-(6-Acryloyloxyhexyl)phenoxy]-difluoromethyl}-3,5-difluorophenyl)hexyl acrylate 1.1: 5-Bromo-2[(4-bromophenoxy)difluoromethyl]-1,3-difluorobenzene

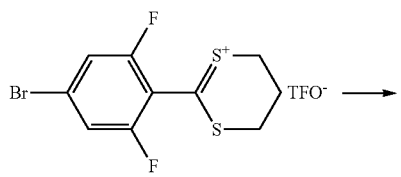

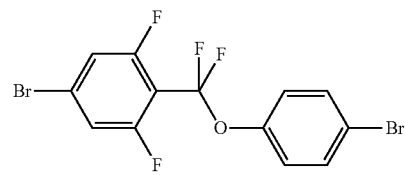

92.0 g (0.200 mol) of 2-(4-bromo-2,6-difluorophenyl)-5,6-dihydro-4H-1,3-dithiyn-1-ylium triflate are initially introduced in 600 ml of dichloromethane, and a solution of 52.0 g (0.300 mol) of 4-bromophenol in 200 ml of dichloromethane and 45 ml of triethylamine is added at −70° C. When the addition is complete, the mixture is stirred at −70° C. for a further 1 h, 160 ml (1.00 mol) of triethylamine trishydrofluoride are added, and a solution of 51.0 ml (0.996 mol) of bromine in 200 ml of dichloromethane is subsequently added dropwise. After 1 h, the cooling is removed, and, after warming to −10° C., the batch is added to a solution of 310 ml of 32 per cent sodium hydroxide solution in 2 l of ice-water. The org. phase is separated off and washed with water. The aqueous phase is extracted with dichloromethane, and the combined org. phases are dried over sodium sulfate. The solvent is removed in vacuo, and the residue is filtered through silica gel with heptane, giving 5-bromo-2-[(4-bromophenoxy)difluoromethyl]-1,3-difluorobenzene as a yellow oil.

$^{19}$F-NMR (CDCl$_3$, 235 MHz)

δ=−63.1 ppm (t, J=26.7 Hz, 2 F, —CF$_2$O—), −112 (dt, J=9.7 Hz, J=26.7 Hz, 2 F, Ar—F).

1.2: 6-(4-{Difluoro[4-(6-hydroxyhex-1-ynyl)phenoxy]methyl}-3,5-difluorophenyl)hex-5-yn-1-ol

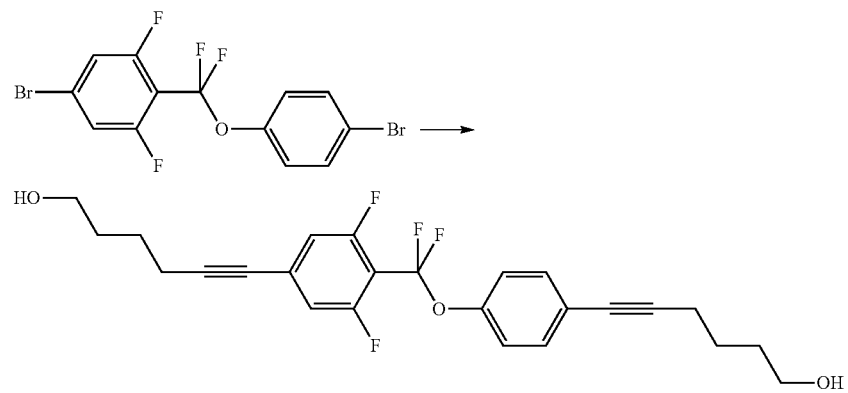

10.7 g (25.8 mmol) of 5-bromo-2-[(4-bromophenoxy)difluoromethyl]-1,3-difluorobenzene and 8.00 g (81.5 mmol) of hex-5-yn-1-ol are initially introduced in 11.3 ml of triethylamine and 500 ml of toluene, 1.50 g (2 mmol) of bis(triphenylphosphine)palladium(II) chloride and 0.700 g (3.68 mmol) of copper(I) iodide are added, and the mixture is heated under reflux overnight. The batch is subsequently added to water, neutralised using 2 N hydrochloric acid and extracted three times with toluene. The combined org. phases are dried over sodium sulfate, the solvent is removed in vacuo, and the residue is chromatographed on silica gel firstly with toluene and then with toluene/ethyl acetate (4:1), giving 6-(4-{difluoro[4-(6-hydroxyhex-1-ynyl)phenoxy]methyl}-3,5-difluorophenyl)hex-5-yn-1-ol as a colourless solid.

6-(4-{Difluoro[4-(6-hydroxyhex-1-ynyl)phenoxy]methyl}-3,5-difluorophenyl)hex-5-yn-1-ol is hydrogenated to completion on palladium/active carbon catalyst in THF. The catalyst is filtered off, the solvent is removed in vacuo, and the crude product is chromatographed on silica gel with toluene/ethyl acetate (1:2), giving 6-(4-{difluoro[4-(6-hydroxyhexyl)phenoxy]methyl}-3,5-difluorophenyl)hexan-1-ol as a colourless solid.

$^{19}$F-NMR (CDCl$_3$, 235 MHz)

δ=−60.8 ppm (t, J=26.3 Hz, 2 F, —CF$_2$O—), −112 (dt, J=10.0 Hz, J=26.3 Hz, 2 F, Ar—F).

1.3: 6-(4-{Difluoro[4-(6-hydroxyhexyl)phenoxy]methyl}-3,5-difluorophenyl)hexan-1-ol

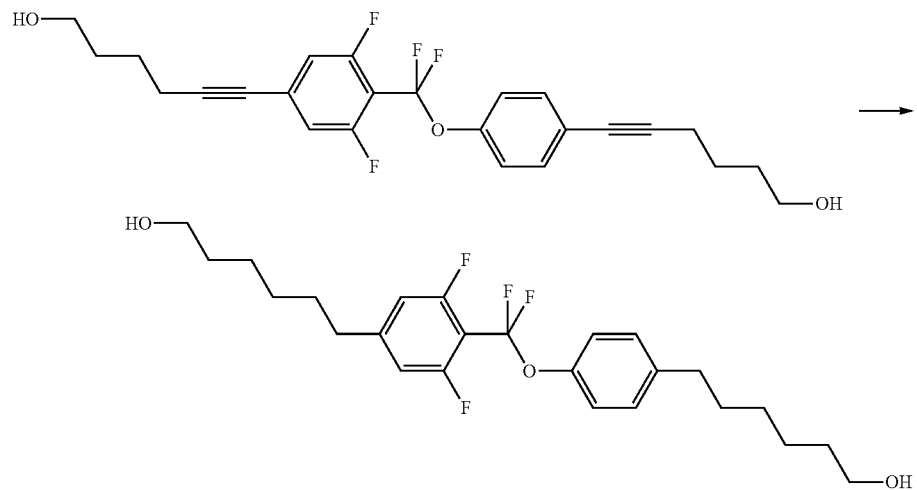

1.4: 6-(4-{[4-(6-Acryloyloxyhexyl)phenoxy]difluoromethyl}-3,5-difluoro-phenyl)hexyl acrylate

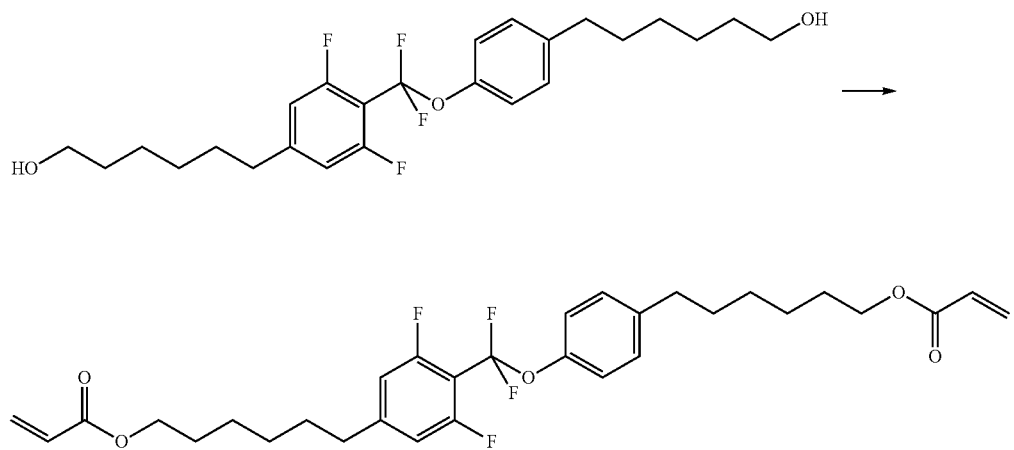

17.0 g (37.2 mmol) of 6-(4-{difluoro[4-(6-hydroxyhexyl)phenoxy]methyl}-3,5-difluorophenyl)hexan-1-ol, 8.05 g (112 mmol) of acrylic acid and 0.5 g of DMAP are initially introduced in 300 ml of dichloromethane, and a solution of 17.3 g (112 mmol) of EDC in 75 ml of dichloromethane is added dropwise with ice cooling. After 1 h, the cooling is removed, and the batch is left to stir overnight at ambient temperature. The vast majority of the solvent is removed in vacuo, and the residue is chromatographed on silica gel with dichloromethane, giving 6-(4-{[4-(6-acryloyloxyhexyl)phenoxy]-difluoromethyl}-3,5-difluorophenyl)hexyl acrylate as a colourless oil. Phase behaviour: $T_g$ −71° C. 13 l.

$^1$H-NMR (CDCl$_3$, 250 MHz)
δ=1.25-1.48 ppm (m, 8 H, CH$_2$), 1.50-1.74 ppm (m, 8 H, CH$_2$), 2.60 (m, 4 H, 2 —Ar—CH$_2$—), 4.13 (t, J=6.7 Hz, 2 H, —CH$_2$O—), 4.15 (t, J=6.7 Hz, 2 H, —CH$_2$O—), 5.81 (dt, J=10.4 Hz, J=1.8 Hz, 2 H, 2 CHH=CH—COO—), 6.11 (m$_c$, 2 H, 2 CH$_2$=CH—OCO—), 6.39 (2 CHH=CH—OCO—), 6.78 (d, J=10.0 Hz, 2 H, Ar—H), 7.15 (m$_e$, 4 H, Ar—H).

$^{19}$F-NMR (CDCl$_3$, 235 MHz)
δ=−60.9 ppm (t, J=26.4 Hz, 2 F, —CF$_2$O—), −112.0 (dt, J=26.4, J=10.0 Hz, 2 F, Ar—F).

Analogously the following reactive compounds are obtained

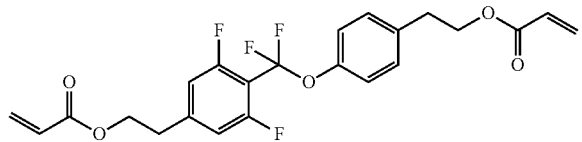 [SMILES: C=CC(=O)OCCc1ccc(OC(F)(F)c2c(F)cc(CCOC(=O)C=C)cc2F)cc1]

Phase behaviour: to be determined.

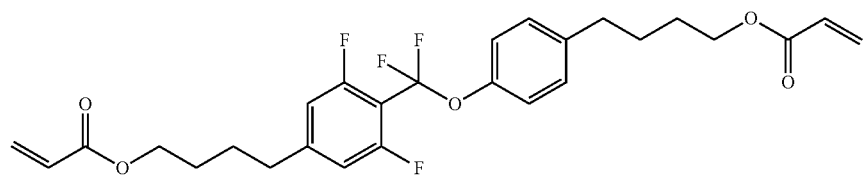 [SMILES: C=CC(=O)OCCCCc1ccc(OC(F)(F)c2c(F)cc(CCCCOC(=O)C=C)cc2F)cc1]

Phase behaviour: $T_g$ −66° C. I.

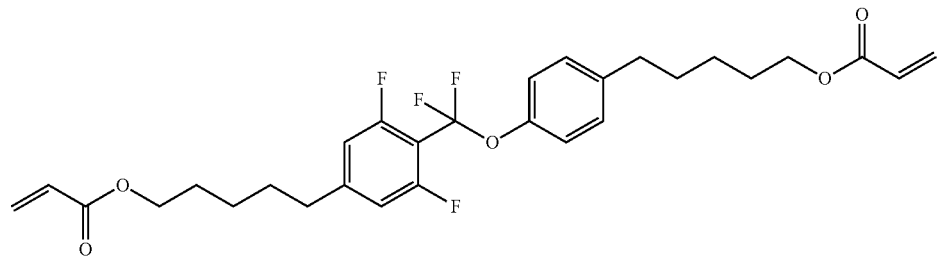 [SMILES: C=CC(=O)OCCCCCc1ccc(OC(F)(F)c2c(F)cc(CCCCCOC(=O)C=C)cc2F)cc1]

Phase behaviour: $T_g$ −69° C. I.

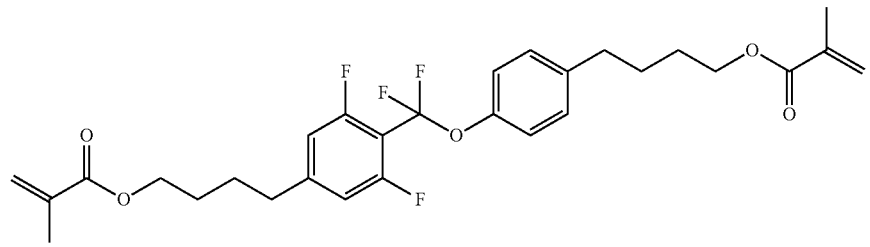 [SMILES: C=C(C)C(=O)OCCCCc1ccc(OC(F)(F)c2c(F)cc(CCCCOC(=O)C(=C)C)cc2F)cc1]

Phase behaviour: to be determined.

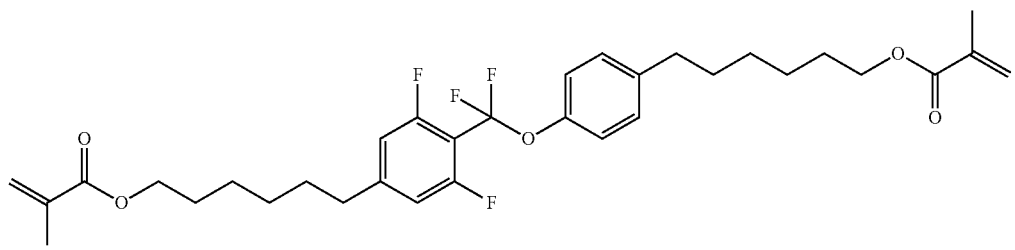 [SMILES: C=C(C)C(=O)OCCCCCCc1ccc(OC(F)(F)c2c(F)cc(CCCCCCOC(=O)C(=C)C)cc2F)cc1]

Phase behaviour: to be determined.
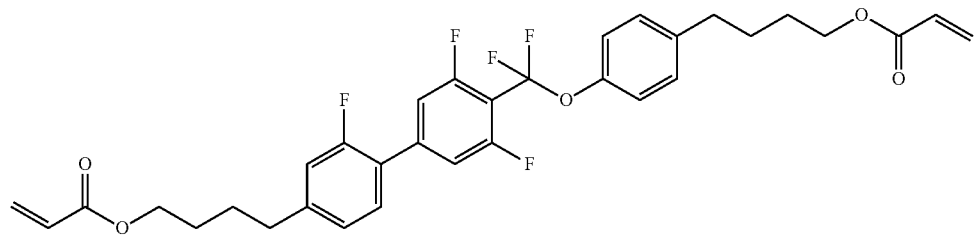 [SMILES: C=CC(=O)OCCCCc1ccc(OC(F)(F)c2c(F)cc(-c3ccc(CCCCOC(=O)C=C)cc3F)cc2F)cc1]
Phase behaviour: to be determined.
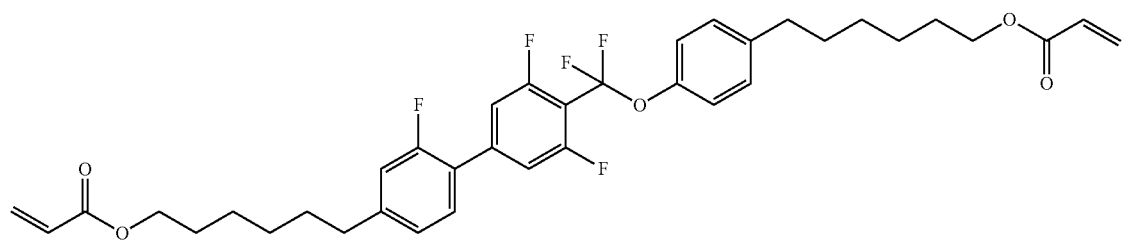 [SMILES: C=CC(=O)OCCCCCCc1ccc(OC(F)(F)c2c(F)cc(-c3ccc(CCCCCCOC(=O)C=C)cc3F)cc2F)cc1]
Phase behaviour: to be determined.
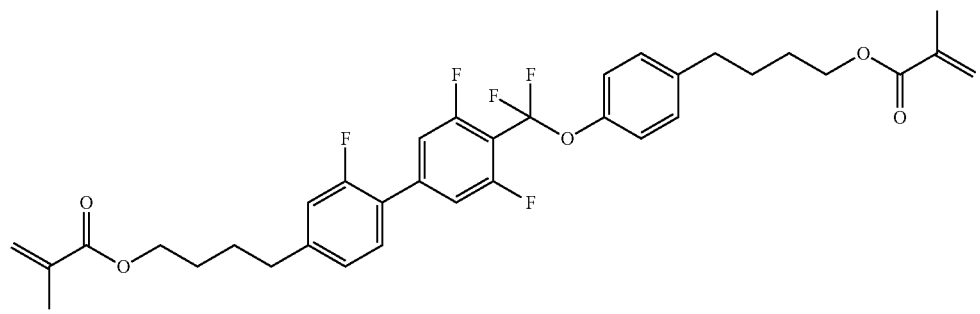 [SMILES: C=C(C)C(=O)OCCCCc1ccc(OC(F)(F)c2c(F)cc(-c3ccc(CCCCOC(=O)C(=C)C)cc3F)cc2F)cc1]
Phase behaviour: C 128° C. I.
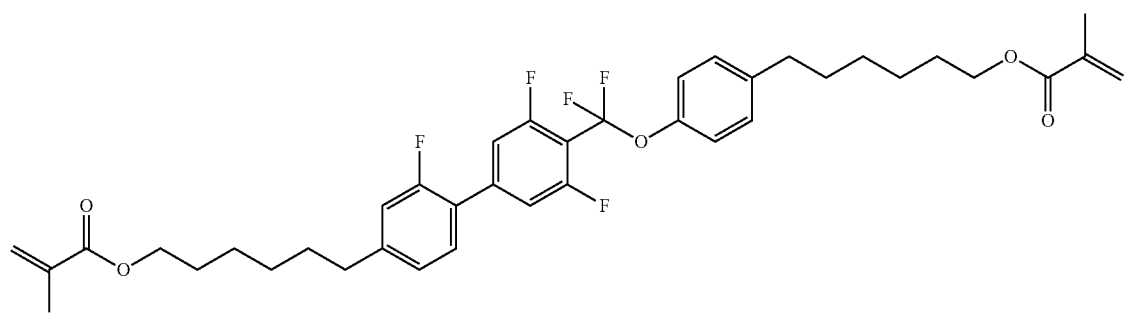 [SMILES: C=C(C)C(=O)OCCCCCCc1ccc(OC(F)(F)c2c(F)cc(-c3ccc(CCCCCCOC(=O)C(=C)C)cc3F)cc2F)cc1]
Phase behaviour: $T_g$ −59° C. N −28.5° C. I.

Example 1

The following liquid crystalline mixture M-1 is prepared and investigated with respect to its general physical properties. The composition and properties are given in the following table.

| Composition and properties liquid crystal mixture M-1 | | |
|---|---|---|
| Composition | | |
| Compound | | Conc./ |
| No. | Abbreviation | mass-% |
| 1 | DGUQU-3-F | 11.0 |
| 2 | GUQU-2-N | 15.0 |
| 3 | GUQU-3-N | 15.0 |
| 4 | GUUQU-5-N | 8.0 |
| 5 | GUQU-3-F | 5.0 |
| 6 | PUQGU-2-F | 11.0 |
| 7 | PUQGU-3-F | 11.0 |
| 8 | GUQGU-2-T | 12.0 |
| 9 | GUQGU-3-T | 12.0 |
| Σ | | 100.0 |

| Composition and properties liquid crystal mixture M-1 | |
|---|---|
| Physical Properties | |
| T(N, I) = | 64° C. |
| $n_e$(20° C., 589 nm) = | 1.6774 |
| Δn(20° C., 589 nm) = | 0.1878 |
| $\epsilon_\perp$(20°, 1 kHz) = | t.b.d. |
| Δε(20°, 1 kHz) = | t.b.d. |

Remarks: t.b.d.: to be determined 3.8% of the chiral agent R-5011 are solved in the achiral liquid crystal mixture and the electro-optical response of resultant mixture in an IPS-type cell is investigated. The mixture is filled into an electro optical test cell with interdigital electrodes on one substrate side. The electrode width is 10 µm, the distance between adjacent electrodes is 10 µm and the cell gap is also 10 µm. This test cell is evaluated electro-optically between crossed polarisers.

Appropriate Concentrations a) of the chiral dopant R-5011 (Merck KGaA, Germany), b) of the reactive mesogen of the formula RM-C

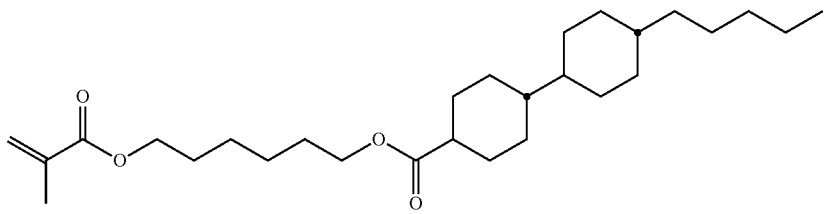

and c) alternatively of one of the two reactive mesogenic compounds of the formulae RM-1

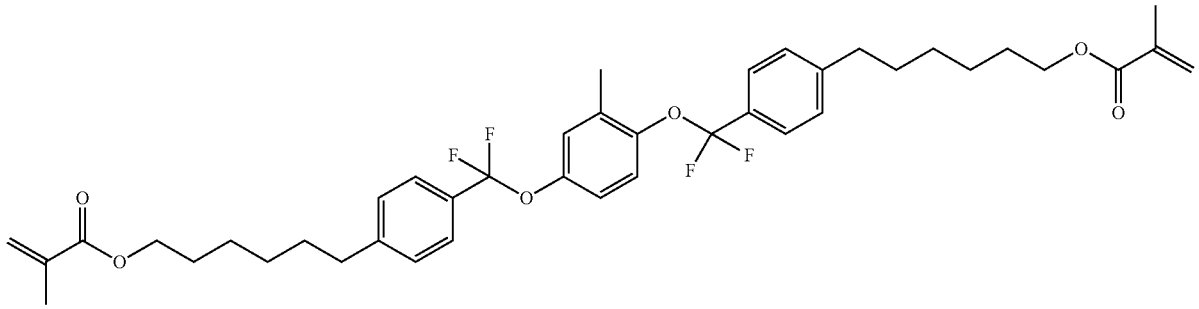 [SMILES: C=C(C)C(=O)OCCCCCCc1ccc(C(F)(F)Oc2ccc(OC(F)(F)c3ccc(CCCCCCOC(=O)C(=C)C)cc3)c(C)c2)cc1]

and RM-2

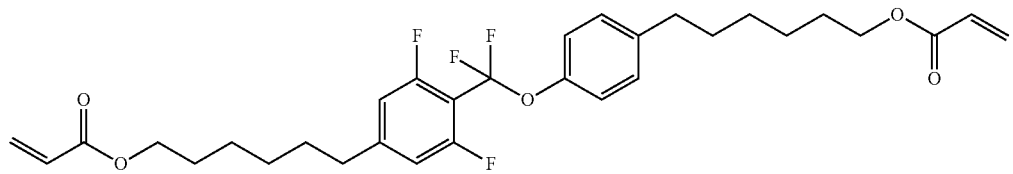 [SMILES: C=CC(=O)OCCCCCCc1ccc(OC(F)(F)c2c(F)cc(CCCCCCOC(=O)C=C)cc2F)cc1]

respectively, are added to the mixture of interest, here mixture M-1. The resultant mixture is introduced into test cells and heated to an appropriate temperature, at which the mixture is in the blue phase. Then it is exposed to UV.

The mixtures are characterised as described below before the polymerisation. The reactive components are then polymerised in the blue phase by irradiation once (180 s), and the resultant media are recharacterised.

Detailed Description of the Polymerisation

Before the polymerisation of a sample, the phase properties of the medium are established in a test cell having a thickness of about 10 microns and an area of 2×2.5 cm². The filling is carried out by capillary action at a temperature of 75° C. The measurement is carried out under a polarising microscope with heating stage with a temperature change of 1° C./min.

The polymerisation of the media is carried out by irradiation with a UV lamp (Dymax, Bluewave 200, 365 nm interference filter) having an effective power of about 3.0 mW/cm² for 180 seconds. The polymerisation is carried out directly in the electro-optical test cell.

The polymerisation is carried out initially at a temperature at which the medium is in the blue phase I (BP-I). The polymerisation is carried out in a plurality of part-steps, which gradually result in complete polymerisation. The temperature range of the blue phase generally changes during the polymerisation. The temperature is therefore adapted between each part-step so that the medium is still in the blue phase. In practice, this can be carried out by observing the sample under the polarising microscope after each irradiation operation of about 5 s or longer. If the sample becomes darker, this indicates a transition into the isotropic phase. The temperature for the next part-step is reduced correspondingly.

The entire irradiation time which results in maximum stabilisation is typically 180 s at the irradiation power indicated. Further polymerisations can be carried out in accordance with an optimised irradiation/temperature programme.

Alternatively, the polymerisation can also be carried out in a single irradiation step, in particular if a broad blue phase is already present before the polymerisation.

Electro-optical Characterisation

After the above-described polymerisation and stabilisation of the blue phase, the phase width of the blue phase is determined. The electro-optical characterisation is carried out subsequently at various temperatures within and if desired also outside this range.

The test cells used are fitted on one side with interdigital electrodes on the cell surface. The cell gap, the electrode separation and the electrode width are typically each 10 microns. This uniform dimension is referred to below as the gap width. The area covered by electrodes is about 0.4 cm². The test cells do not have an alignment layer.

For the electro-optical characterisation, the cell is located between crossed polarising filters, where the longitudinal direction of the electrodes adopts an angle of 45° to the axes of the polarising filter. The measurement is carried out using a DMS301 (Autronic-Melchers, Germany) at a right angle to the cell plane, or by means of a highly sensitive camera on the polarising microscope. In the voltage-free state, the arrangement described gives an essentially dark image (definition 0% transmission).

Firstly, the characteristic operating voltages and then the response times are measured on the test cell. The operating voltage is applied to the cell electrodes in the form of rectangular voltage having an alternating sign (frequency 100 Hz) and variable amplitude, as described below.

The transmission is measured while the operating voltage is increased. The attainment of the maximum value of the transmission defines the characteristic quantity of the operating voltage $V_{100}$. Equally, the characteristic voltage $V_{10}$ is determined at 10% of the maximum transmission. These values are measured at various temperatures in the range of the blue phase.

Relatively high characteristic operating voltages $V_{100}$ are observed at the upper and lower end of the temperature range of the blue phase. In the region of the minimum operating voltage, $V_{100}$ generally only increases slightly with increasing temperature. This temperature range, limited by $T_1$ and $T_2$, is referred to as the usable, flat temperature range (FR). The width of this "flat range" (FR) is $(T_2-T_1)$ and is known as the width of the flat range (WFR). The precise values of $T_1$ and $T_2$ are determined by the intersections of tangents on the flat curve section FR and the adjacent steep curve sections in the $V_{100}$/temperature diagram.

In the second part of the measurement, the response times during switching on and off ($\tau_{on}$, $\tau_{off}$) are determined. The response time $\tau_{on}$ is defined by the time to achievement of 90% intensity after application of a voltage at the level of $V_{100}$ at the selected temperature. The response time $\tau_{off}$ is defined by the time until the decrease by 90% starting from maximum intensity at $V_{100}$ after reduction of the voltage to 0 V. The response time is also determined at various temperatures in the range of the blue phase.

As further characterisation, the transmission at continuously increasing and falling operating voltage between 0 V and $V_{100}$ is measured at a temperature within the FR. The difference between the two curves is known as hysteresis. The difference in the transmissions at $0.5 \cdot V_{100}$ and the difference in the voltages at 50% transmission are, for example, characteristic hysteresis values and are known as $\Delta T_{50}$ and $\Delta V_{50}$ respectively.

As a further characteristic quantity, the ratio of the transmission in the voltage-free state before and after passing through a switching cycle can be measured. This transmission ratio is referred to as the "memory effect". The value of the memory effect is 1.0 in the ideal state. Values above 1 mean that a certain memory effect is present in the form of excessively high residual transmission after the cell has been switched on and off. This value is also determined in the working range of the blue phase (FR). Typical concentrations of the polymer precursors are as follows.

| | Sample | | |
| Constituent | 1 | 2 | 3 |
| | Concentration/% | | |
| --- | --- | --- | --- |
| M-1 | 87.0 | 89.0 | 87.4 |
| R-5011 | 3.8 | 3.8 | 3.4 |
| RM-C | 5.0 | 4.0 | 5.0 |
| RM-2 | 4.0 | 3.0 | 4.0 |
| IRG-651 ® | 0.2 | 0.2 | 0.2 |
| Σ | 100.0 | 100.0 | 100.0 |

The polymerisable mixture is polymerised in a single irradiation step at a temperature of about 30-50° C. at the lower end of the temperature range of the blue phase. The polymer-stabilised liquid-crystalline media exhibit a blue phase over a broad temperature range.

The polymer-stabilised medium M-1, prepared using the monomer (1) according to the invention, exhibits a reduction in hysteresis ($\Delta V_{50}$) and good contrast on switching on and on switching off compared with conventional media from the prior art. In particular, the contrast on switching on and the contrast on switching off are close together in the medium M1 according to the invention, which means very good stabilisation of the blue phase.

It can be seen from this that the monomers according to the invention are particularly suitable for the stabilisation of blue phases, in particular in the case of media having a high concentration of chiral dopant.

Comparative Examples 1-1 and 1-2

The following liquid crystalline mixture (C-1) is prepared and investigated with respect to its general physical properties. The composition and properties are given in the following table.

| Composition and properties liquid crystal mixture C-1 | | |
| --- | --- | --- |
| Composition | | |
| Compound | | Conc./ |
| No. | Abbreviation | mass-% |
| 1 | AUUQU-2-F | 10.0 |
| 2 | AUUQU-3-F | 11.0 |
| 3 | AUUQU-4-F | 7.0 |
| 4 | AUUQU-5-F | 6.0 |
| 5 | AUUQU-7-F | 7.0 |
| 6 | AUUQU-3-T | 10.0 |
| 7 | AUUQU-3-OT | 11.0 |
| 8 | AGUQU-3-F | 4.0 |
| 9 | AUUQU-3-N | 5.0 |
| 10 | PUZU-2-F | 7.0 |
| 11 | PUZU-3-F | 11.0 |
| 12 | PUZU-5-F | 11.0 |
| Σ | | 100.0 |
| Physical Properties | | |
| T(N, I) = | | 71° C. |
| $n_e$(20° C., 589 nm) = | | t.b.d. |
| $\Delta n$(20° C., 589 nm) = | | 0.1515 |
| $\epsilon_\perp$(20°, 1 kHz) = | | t.b.d. |
| $\Delta\epsilon$(20°, 1 kHz) = | | 224 |
| $\gamma_1$(30° C.) = | | 763 mPa · s |

This mixture is treated and investigated as described in detail under example 1 above. The results are compiled in the following table.

| Mixture | C-1-1 | C-1-2 |
| --- | --- | --- |
| Host | C-1 | |
| Reactive mesogen | RM-1 | RM-2 |
| Measurement values (20° C.) | | |
| Transition point before the polymerisation | t.b.d. | t.b.d. |
| Polymerisation temperature/° C. | t.b.d. | t.b.d. |
| $V_{10}$ (20° C.)/V | 29.8 | 20.8 |
| $V_{90}$ (20° C.)/V | 58.6 | 42.0 |
| $V_{100}$ (20° C.)/V | 67.0 | 47.9 |
| $\Delta V_{50}$ (20° C.)/V | 4.73 | 1.90 |
| Contrast, switching on | 285 | 206 |
| Contrast, switching off | 276 | 208 |
| Memory effect | 1.04 | 0.99 |

Remarks: t.b.d.: to be determined

Comparative Example 2

The following liquid crystalline mixture (C-2) is prepared and investigated with respect to its general physical properties. The composition and properties are given in the following table.

| Composition and properties liquid crystal mixture C-2 | | |
| --- | --- | --- |
| Composition | | |
| Compound | | Conc./ |
| No. | Abbreviation | mass-% |
| 1 | GUQU-3-F | 5.0 |
| 2 | GUQU-4-F | 6.0 |
| 3 | GUQU-5-F | 6.0 |
| 4 | PUQGU-3-T | 8.0 |
| 5 | PUQGU-5-T | 8.0 |
| 6 | GUQGU-2-T | 12.0 |
| 7 | GUQGU-3-T | 12.0 |
| 8 | GUQGU-4-T | 14.0 |
| 9 | GUQGU-5-T | 14.0 |
| 10 | GUQU-3-N | 5.0 |
| 11 | GUUQU-3-N | 10.0 |
| Σ | | 100.0 |
| Physical Properties | | |
| T(N, I) = | | 65° C. |
| $n_e$(20° C., 589 nm) = | | 1.6690 |
| $\Delta n$(20° C., 589 nm) = | | 0.1859 |
| $\epsilon_\perp$(20°, 1 kHz) = | | 12.9 |
| $\Delta\epsilon$(20°, 1 kHz) = | | 277.8 |

Example 2

The following liquid crystalline mixture M-2 is prepared and investigated with respect to its general physical properties. The composition and properties are given in the following table.

| Composition and properties liquid crystal mixture M-2 | | |
| --- | --- | --- |
| Composition | | |
| Compound | | Conc./ |
| No. | Abbreviation | mass-% |
| 1 | DGUQU-3-F | 5.5 |
| 2 | GUQU-2-N | 7.5 |
| 3 | GUQU-3-N | 10.0 |
| 4 | GUUQU-3-N | 5.0 |
| 5 | GUUQU-5-N | 4.0 |
| 6 | GUQU-3-F | 5.0 |
| 7 | GUQU-4-F | 3.0 |
| 8 | GUQU-5-F | 3.0 |
| 9 | PUQGU-2-F | 5.5 |
| 10 | PUQGU-3-F | 5.5 |
| 11 | PUQGU-3-T | 4.0 |
| 12 | PUQGU-5-T | 4.0 |
| 13 | GUQGU-2-T | 12.0 |
| 14 | GUQGU-3-T | 12.0 |
| 15 | GUQGU-4-T | 7.0 |
| 16 | GUQGU-5-T | 7.0 |
| Σ | | 100.0 |

-continued

| Composition and properties liquid crystal mixture M-2 | |
|---|---|
| Physical Properties | |
| T(N, I) = | 64° C. |
| $n_e$(20° C., 589 nm) = | 1.6763 |
| $\Delta n$(20° C., 589 nm) = | 0.1893 |
| $\epsilon_\perp$(20°, 1 kHz) = | t.b.d. |
| $\Delta\epsilon$(20°, 1 kHz) = | 394 |
| $\tau_{off,\ norm.}$ = | 6.42 ms |

Remarks: t.b.d.: to be determined

Typical concentrations of the polymer precursors are as follows.

| Constituent | Sample 1 Concentration % |
|---|---|
| M-2 | 88 |
| R-5011 | 3.8 |
| RM-C | 5.0 |
| RM-1 | 0.0 |
| RM-2 | 3.0 |
| IRG-651 ® | 0.2 |
| Σ | 100.0 |

The results are comparable to those of the preceding examples.

Example 3

The following liquid crystalline mixture M-3 is prepared and investigated with respect to its general physical properties. The composition and properties are given in the following table.

| Composition and properties liquid crystal mixture M-3 | | |
|---|---|---|
| Composition | | |
| Compound | | Conc./ |
| No. | Abbreviation | mass-% |
| 1 | DGUQU-3-F | 8.5 |
| 2 | GUQU-2-N | 11.0 |
| 3 | GUQU-3-N | 12.5 |
| 4 | GUUQU-3-N | 8.5 |
| 5 | GUQU-3-F | 5.0 |
| 6 | GUQU-4-F | 2.0 |
| 7 | PUQGU-2-F | 8.0 |
| 8 | PUQGU-3-F | 8.5 |
| 9 | PUQGU-3-T | 4.0 |
| 10 | GUQGU-2-T | 12.0 |
| 11 | GUQGU-3-T | 12.0 |
| 12 | GUQGU-4-T | 8.0 |
| Σ | | 100.0 |
| Physical Properties | | |
| T(N, I) = | | t.b.d. ° C. |
| $n_e$(20° C., 589 nm) = | | t.b.d. |
| $\Delta n$(20° C., 589 nm) = | | t.b.d. |
| $\epsilon_\perp$(20°, 1 kHz) = | | t.b.d. |
| $\Delta\epsilon$(20°, 1 kHz) = | | t.b.d. |

Remarks: t.b.d.: to be determined

| Constituent | Sample 1 Concentration % |
|---|---|
| M-2 | 88 |
| R-5011 | 3.8 |
| RM-C | 5.0 |
| RM-1 | 0.0 |
| RM-2 | 3.0 |
| IRG-651 ® | 0.2 |
| Σ | 100.0 |

The results are comparable to those of the preceding examples.

Example 4

The following liquid crystalline mixture M-4 is prepared and investigated with respect to its general physical properties. The composition and properties are given in the following table.

| Composition and properties liquid crystal mixture M-4 | | |
|---|---|---|
| Composition | | |
| Compound | | Conc./ |
| No. | Abbreviation | mass-% |
| 1 | DGUQU-3-T | 11.0 |
| 2 | GUQU-2-N | 15.0 |
| 3 | GUQU-3-N | 15.0 |
| 4 | GUUQU-5-N | 8.0 |
| 5 | GUQU-3-F | 5.0 |
| 6 | PUQGU-2-F | 11.0 |
| 7 | PUQGU-3-F | 11.0 |
| 8 | GUQGU-2-T | 12.0 |
| 9 | GUQGU-3-T | 12.0 |
| Σ | | 100.0 |
| Physical Properties | | |
| T(N, I) = | | 63° C. |
| $n_e$(20° C., 589 nm) = | | 1.6752 |
| $\Delta n$(20° C., 589 nm) = | | 0.1871 |
| $\epsilon_\perp$(20°, 1 kHz) = | | t.b.d. |
| $\Delta\epsilon$(20°, 1 kHz) = | | 511 |

Remarks: t.b.d.: to be determined

Typical concentrations of the polymer precursors are as follows.

| Constituent | Sample 1 Concentration/% |
|---|---|
| M-4 | 88.0 |
| R-5011 | 3.8 |
| RM-C | 5.0 |
| RM-1 | 0.0 |
| RM-2 | 3.0 |
| IRG-651 ® | 0.2 |
| Σ | 100.0 |

The results are comparable to those of the preceding examples.

Example 5

The following liquid crystalline mixture M-5 is prepared and investigated with respect to its general physical properties. The composition and properties are given in the following table.

Composition and properties liquid crystal mixture M-5

Composition

| No. | Compound Abbreviation | Conc./ mass-% |
|---|---|---|
| 1 | DUUQU-3-F | 5.0 |
| 2 | DUUQU-4-F | 4.0 |
| 3 | DUUQU-5-F | 4.0 |
| 4 | GUQU-2-N | 8.0 |
| 5 | GUQU-3-N | 7.0 |
| 6 | GUUQU-3-N | 10.0 |
| 7 | PUQGU-3-T | 8.0 |
| 8 | PUQGU-5-T | 8.0 |
| 9 | GUQGU-3-T | 10.0 |
| 10 | GUQGU-5-T | 10.0 |
| 12 | PZG-2-N | 10.0 |
| 13 | PZG-3-N | 5.0 |
| 14 | PPGU-3-F | 4.0 |
| Σ | | 100.0 |

Physical Properties

| | |
|---|---|
| T(N, I) = | 68.5° C. |
| $n_e$(20° C., 589 nm) = | t.b.d. |
| $\Delta n$(20° C., 589 nm) = | t.b.d. |
| $\epsilon_\perp$(20°, 1 kHz) = | t.b.d. |
| $\Delta\epsilon$(20°, 1 kHz) = | t.b.d. |

Remarks: t.b.d.: to be determined

Typical concentrations of the polymer precursors are as follows.

| Constituent | Sample 1 Concentration/% |
|---|---|
| M-5 | 83.6 |
| R-5011 | 4.2 |
| RM-C | 7.0 |
| RM-1 | 5.0 |
| RM-2 | 0.0 |
| IRG-651 ® | 0.2 |
| Σ | 100.0 |

The results are summarised in the following table.

| Mixture | M-5-1 |
|---|---|
| Host | M-5 |
| Reactive mesogen | RM-1 |
| Transition point before the polymerisation | 32.7 |
| Polymerisation temp./° C. | 32.2 |

| Measurement values | Temperature/° C. | | |
|---|---|---|---|
| | 20 | 25 | 30 |
| $V_{100}$ (T)/V | 40.0 | 44.0 | 50.0 |
| $\Delta V_{50}$ (T)/V | 0.9 | 1.1 | 1.0 |
| Memory effect | 0.97 | 1.02 | 1.00 |
| $t_{on}$ (T)/ms | 3.94 | 2.78 | 0.98 |
| $t_{off}$ (T)/ms | 4.12 | 1.57 | 0.92 |
| Contrast, switching on | t.b.d. | t.b.d. | t.b.d. |
| Contrast, switching off | t.b.d. | t.b.d. | t.b.d. |

Remarks: t.b.d.: to be determined

Example 6

The following liquid crystalline mixture M-6 is prepared and investigated with respect to its general physical properties. The composition and properties are given in the following table.

Composition and properties liquid crystal mixture M-6

Composition

| No. | Compound Abbreviation | Conc./ mass-% |
|---|---|---|
| 1 | DUUQU-3-F | 7.0 |
| 2 | DUUQU-4-F | 8.0 |
| 3 | DUUQU-5-F | 8.0 |
| 4 | GUQU-2-N | 8.0 |
| 5 | GUQU-3-N | 8.0 |
| 6 | GUUQU-3-N | 10.0 |
| 7 | PUQGU-3-T | 8.0 |
| 8 | PUQGU-4-T | 8.0 |
| 9 | PUQGU-5-T | 8.0 |
| 10 | PZG-2-N | 10.0 |
| 12 | PZG-3-N | 10.0 |
| 13 | PPGU-3-F | 7.0 |
| Σ | | 100.0 |

Physical Properties

| | |
|---|---|
| T(N, I) = | 68° C. |
| $n_e$(20° C., 589 nm) = | t.b.d. |
| $\Delta n$(20° C., 589 nm) = | t.b.d. |
| $\epsilon_\perp$(20°, 1 kHz) = | t.b.d. |
| $\Delta\epsilon$(20°, 1 kHz) = | t.b.d. |

Remarks: t.b.d.: to be determined

Typical concentrations of the polymer precursors are as follows.

| Constituent | Sample 1 Concentration/% |
|---|---|
| M-6 | 83.6 |
| R-5011 | 4.2 |
| RM-C | 7.0 |
| RM-1 | 5.0 |
| RM-2 | 0.0 |
| IRG-651 ® | 0.2 |
| Σ | 100.0 |

The results are summarised in the following table.

| Mixture | M-6-1 |
|---|---|
| Host | M-6 |
| Reactive mesogen | RM-1 |
| Transition point before the polymerisation | 33.7 |
| Polymerisation temp./° C. | 33.2 |

-continued

| Measurement values | Temperature/° C. | | |
|---|---|---|---|
| | 20 | 25 | 30 |
| $V_{100}$ (T)/V | 46.0 | 50.0 | 55.0 |
| $\Delta V_{50}$ (T)/V | 1.0 | 0.8 | 1.0 |
| Memory effect | 0.99 | 0.98 | 1.00 |
| $t_{on}$ (T)/ms | 3.74 | 2.13 | 0.86 |
| $t_{off}$ (T)/ms | 2.87 | 1.29 | 0.79 |
| Contrast, switching on | t.b.d. | t.b.d. | t.b.d. |
| Contrast, switching off | t.b.d. | t.b.d. | t.b.d. |

Remarks: t.b.d.: to be determined

Example 7

The following liquid crystalline mixture M-7 is prepared and investigated with respect to its general physical properties. The composition and properties are given in the following table.

| Composition and properties liquid crystal mixture M-7 | | |
|---|---|---|
| Composition | | |
| No. | Compound Abbreviation | Conc./ mass-% |
| 1 | DUUQU-3-F | 7.0 |
| 2 | DUUQU-4-F | 8.0 |
| 3 | DUUQU-5-F | 8.0 |
| 4 | GUQU-2-N | 8.0 |
| 5 | GUQU-3-N | 8.0 |
| 6 | GUUQU-3-N | 10.0 |
| 7 | PUQGU-3-T | 7.0 |
| 8 | PUQGU-4-T | 8.0 |
| 9 | PUQGU-5-T | 7.0 |
| 10 | PZG-2-N | 10.0 |
| 12 | PZG-3-N | 10.0 |
| 13 | DPGU-4-F | 5.0 |
| 14 | PPGU-3-F | 4.0 |
| Σ | | 100.0 |
| Physical Properties | | |
| T(N, I) = | 70° C. | |
| $n_e$(20° C., 589 nm) = | t.b.d. | |
| $\Delta n$(20° C.,589 nm) = | t.b.d. | |
| $\epsilon_\perp$(20°, 1 kHz) = | t.b.d. | |
| $\Delta\epsilon$(20°, 1 kHz) = | t.b.d. | |

Remarks: t.b.d.: to be determined

Typical concentrations of the polymer precursors are as follows.

| Constituent | Sample 1 Concentration/% |
|---|---|
| M-5 | 84.6 |
| R-5011 | 4.2 |
| RM-C | 7.0 |
| RM-1 | 4.0 |
| RM-2 | 0.0 |
| IRG-651 ® | 0.2 |
| Σ | 100.0 |

The results are summarised in the following table.

| Mixture | M-7-1 |
|---|---|
| Host | M-7 |
| Reactive mesogen | RM-1 |
| Transition point before the polymerisation | t.b.d. |
| Polymerisation temp./° C. | t.b.d. |

| Measurement values | Temperature/° C. | | |
|---|---|---|---|
| | 20 | 25 | 30 |
| $V_{100}$ (T)/V | t.b.d. | t.b.d. | t.b.d. |
| $\Delta V_{50}$ (T)/V | t.b.d. | t.b.d. | t.b.d. |
| Memory effect | t.b.d. | t.b.d. | t.b.d. |
| $t_{on}$ (T)/ms | t.b.d. | t.b.d. | t.b.d. |
| $t_{off}$ (T)/ms | t.b.d. | t.b.d. | t.b.d. |
| Contrast, switching on | t.b.d. | t.b.d. | t.b.d. |
| Contrast, switching off | t.b.d. | t.b.d. | t.b.d. |

Remarks: t.b.d.: to be determined

The invention claimed is:

1. A mesogenic medium exhibiting a blue phase, comprising
one or more chiral compounds,
and
one or more compounds of formula D

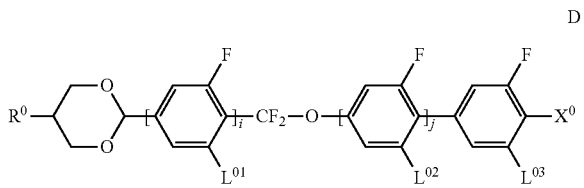

wherein
$R^0$ is alkyl with 1 to 12 C-atoms, which is straight chain or branched, is unsubstituted, mono- or poly-substituted by F, Cl or CN, and in which one or more $CH_2$ groups are optionally replaced, in each case independently from one another, by —O—, —S—, —$NR^{01}$—, —$SiR^{01}R^{02}$—, —CO—, —COO—, —OCO—, —OCO—O—, —S—CO—, —CO—S—, —$CY^{01}$=$CY^{02}$— or —C≡C— in such a manner that O and/or S atoms are not linked directly to one another,
$Y^{01}$ and $Y^{02}$ are, independently of each other, F, Cl or CN, and alternatively one of them may be H,
$R^{01}$ and $R^{02}$ are, independently of each other, H or alkyl with 1 to 12 C-atoms,
$L^{01}$ to $L^{03}$ are in each occurrence independently of each other H or F,
$X^0$ is F or $OCF_3$,
i is 1, 2 or 3,
j is 0,
and
one or more compounds of formula I

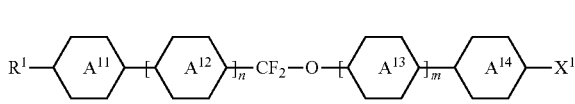

wherein
$R^1$ is alkyl, which is straight chain or branched, is unsubstituted, mono- or poly-substituted by F, Cl or CN, and in which one or more CH$_2$ groups are optionally replaced, in each case independently from one another, by —O—, —S—, —NR$^{01}$—, —SiR$^{01}$R$^{02}$—, —CO—, —COO—, —OCO—, OCO—O—, S—CO—, —CO—S—, —CY$^{01}$=CY$^{02}$— or —C≡C —in such a manner that O and/or S atoms are not linked directly to one another, Y$^{01}$ and Y$^{02}$ are, independently of each other, F, Cl or CN, and alternatively one of them may be H, R$^{01}$ and R$^{02}$ are, independently of each other, H or alkyl with 1 to 12 C-atoms, X$^1$ is F,Cl,CF$_3$, OCF$_3$ or CN,

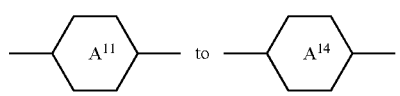

are in each occurrence independently of one another

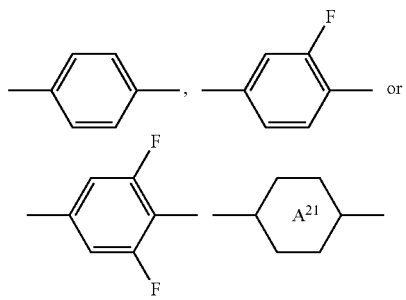

alternatively may be

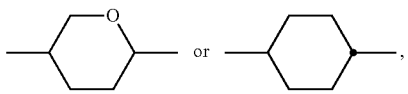

n is 0 or 1, and
m is 1,
and wherein the medium exhibits a blue phase.

2. The mesogenic medium according to claim 1, wherein, in a compound of formula I, n is 0.

3. The mesogenic medium according to claim 1, which comprises one or more compounds of formulae D-1 or D-3

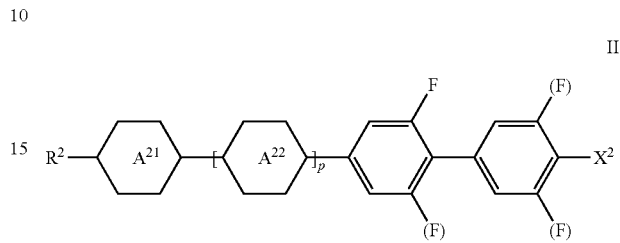

wherein R$^0$, L$^{01}$ to L$^{03}$, i and j have the meanings given for the compound of formula D.

4. The mesogenic medium according to claim 3, which comprises one or more compounds of formula D-1.

5. The mesogenic medium according to claim 1, which further comprises one or more compounds of formulae II to III

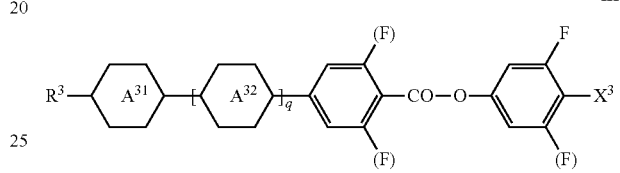

wherein

R$^2$ and R$^3$ each, independently of each other, is alkyl, which is straight chain or branched, is unsubstituted, mono- or poly-substituted by F, Cl or CN, and in which one or more CH$_2$ groups are optionally replaced, in each case independently from one another, by —O—, —S—, —NR$^{01}$—, —SiR$^{01}$R$^{02}$—, —CO—, —COO—, —OCO—, —OCO—O—, —S—CO—, —CO—S—, —CY$^{01}$=CY$^{02}$—or —C≡C— in such a manner that O and/or S atoms are not linked directly to one another, X$^2$ and X$^3$ are independently of each other F, Cl, CF$_3$, OCF$_3$ or CN, and, if present, are independently of one another -continued

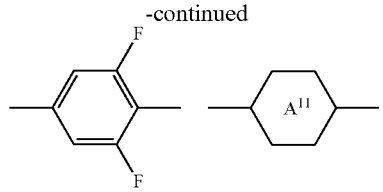

alternatively may be

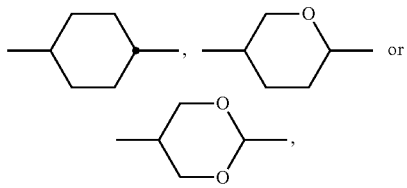

and, if present,

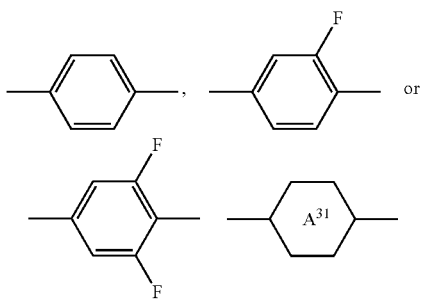

are independently of one another p is 0 or 1 and
q is 0 or 1.

6. The mesogenic medium according to claim 1, which further comprises one or more polymerisable compounds.

7. A method for stabilizing the medium according to claim 6, comprising polymerizing said one or more polymerisable compounds.

8. The mesogenic medium according to claim 1, which further comprises one or more polymerisable compounds, which medium has been stabilised by the polymerisation of said one or more polymerisable compounds.

9. A light modulation element, comprising the medium according to claim 1.

10. An electro-optical display, comprising the medium according to claim 1.

11. The mesogenic medium according to claim 1, wherein $R^0$ is alkyl with 1 to 12 C-atoms, which is straight chain or branched, is unsubstituted, mono- or poly-substituted by F, and in which one or more $CH_2$ groups are optionally replaced, in each case independently from one another, by —O—, —S—, —NR$^{01}$—, —SiR$^{01}$R$^{02}$—, —CO—, —COO—, —OCO—, —OCO—O—, —S—CO—, —CO—S—, —CY$^{01}$=CY$^{02}$— or —C≡C— in such a manner that O and/or S atoms are not linked directly to one another.

12. The mesogenic medium according to claim 1, wherein at least one of the one or more chiral compounds has at least one cholesteric phase.

13. An electro-optical display in a blue phase, comprising the medium according to claim 1.

14. An electro-optical display in a blue phase, comprising the medium according to claim 1 and one or more polymerisable compounds, which medium has been stabilised by the polymerisation of said one or more polymerisable compounds.

15. The mesogenic medium according to claim 1, wherein $X^0$ is F.

16. The mesogenic medium according to claim 1, wherein i is 3.

* * * * *